US009617157B2

(12) United States Patent
Bangera et al.

(10) Patent No.: US 9,617,157 B2
(45) Date of Patent: *Apr. 11, 2017

(54) TUBULAR NANOSTRUCTURE TARGETED TO CELL MEMBRANE

(75) Inventors: Mahalaxmi Gita Bangera, Renton, WA (US); Ed Harlow, Boston, MA (US); Roderick A. Hyde, Redmond, WA (US); Muriel Y. Ishikawa, Livermore, CA (US); Edward K. Y. Jung, Bellevue, WA (US); Eric C. Leuthardt, St. Louis, MO (US); Nathan P. Myhrvold, Medina, WA (US); Dennis J. Rivet, Portsmouth, VA (US); Elizabeth A. Sweeney, Seattle, WA (US); Clarence T. Tegreene, Bellevue, WA (US); Lowell L. Wood, Jr., Bellevue, WA (US); Victoria Y. H. Wood, Livermore, CA (US)

(73) Assignee: Deep Science, LLC, Bellevue, WA (US)

( * ) Notice: Subject to any disclaimer, the term of this patent is extended or adjusted under 35 U.S.C. 154(b) by 2290 days.

This patent is subject to a terminal disclaimer.

(21) Appl. No.: 12/322,367

(22) Filed: Jan. 30, 2009

(65) Prior Publication Data

US 2010/0068808 A1    Mar. 18, 2010

Related U.S. Application Data

(63) Continuation of application No. 12/283,907, filed on Sep. 15, 2008, and a continuation-in-part of application No. 12/283,908, filed on Sep. 15, 2008.

(51) Int. Cl.
*B82Y 40/00* (2011.01)
*C01B 31/02* (2006.01)
*B82Y 30/00* (2011.01)

(52) U.S. Cl.
CPC .......... *C01B 31/0273* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| | | |
|---|---|---|
| 4,496,539 A | 1/1985 | Plotkin et al. |
| 4,877,501 A | 10/1989 | Schnur et al. |
| 4,911,981 A | 3/1990 | Schnur et al. |
| 4,990,291 A | 2/1991 | Schoen et al. |
| 5,227,038 A | 7/1993 | Smalley et al. |
| 5,804,563 A | 9/1998 | Still et al. |
| 5,831,012 A | 11/1998 | Nilsson et al. |
| 6,013,206 A | 1/2000 | Price et al. |
| 6,255,461 B1 | 7/2001 | Mosbach et al. |
| 6,306,610 B1 | 10/2001 | Bawendi et al. |
| 6,339,060 B1 | 1/2002 | Yatvin et al. |
| 6,495,680 B1 | 12/2002 | Gong |
| 6,613,875 B1 | 9/2003 | Ghadiri |
| 6,670,179 B1 | 12/2003 | Mattson et al. |
| 6,670,427 B1 | 12/2003 | Ulbricht et al. |
| 6,692,717 B1 | 2/2004 | Smalley et al. |
| 6,797,522 B1 | 9/2004 | Still et al. |
| 6,821,730 B2 | 11/2004 | Hannah |
| 6,841,139 B2 | 1/2005 | Margrave et al. |
| 7,008,604 B2 | 3/2006 | Smalley et al. |
| 7,087,770 B2 | 8/2006 | Wolff et al. |
| 7,098,030 B2 | 8/2006 | Rozema et al. |
| 7,133,725 B2 | 11/2006 | Stirbl et al. |
| 7,169,329 B2 | 1/2007 | Wong et al. |
| 7,288,623 B2 | 10/2007 | Ghadiri |
| 7,304,128 B2 | 12/2007 | Jagota et al. |
| 7,348,453 B2 | 3/2008 | Rozema et al. |
| 7,399,400 B2 | 7/2008 | Soundarrajan et al. |
| 8,246,995 B2 | 8/2012 | Dai et al. |
| 2003/0102263 A1 | 6/2003 | Lopez et al. |
| 2003/0134433 A1 | 7/2003 | Gabriel et al. |
| 2003/0232340 A1 | 12/2003 | Anderson |
| 2004/0018508 A1 | 1/2004 | Friedman |
| 2004/0023372 A1 | 2/2004 | Klein et al. |
| 2004/0033584 A1 | 2/2004 | Lederberg |
| 2004/0082521 A1 | 4/2004 | Singh |

(Continued)

FOREIGN PATENT DOCUMENTS

| | | |
|---|---|---|
| JP | 2005-185972 A | 7/2005 |
| WO | WO 2005/003722 A2 | 1/2005 |

(Continued)

OTHER PUBLICATIONS

Benson et al.; "GenBank"; Nucleic Acids Research; 2008; pp. D25-D30; vol. 36, Database issue.

(Continued)

*Primary Examiner* — Christopher M Babic
*Assistant Examiner* — Arthur S Leonard

(57) ABSTRACT

Devices, compositions, and methods are described which provide a tubular nanostructure or a composite tubular nanostructure targeted to a lipid bilayer membrane. The tubular nanostructure includes a hydrophobic surface region flanked by two hydrophilic surface regions. The tubular nanostructure is configured to interact with a lipid bilayer membrane and form a pore in the lipid bilayer membrane. The tubular nanostructure may be targeted by including at least one ligand configured to bind to one or more cognates on the lipid bilayer membrane of a target cell.

57 Claims, 10 Drawing Sheets

(56) References Cited

U.S. PATENT DOCUMENTS

| | | |
|---|---|---|
| 2004/0180094 A1 | 9/2004 | Joyce |
| 2005/0107289 A1 | 5/2005 | Ghadiri et al. |
| 2005/0171434 A1 | 8/2005 | Madden et al. |
| 2005/0180917 A1 | 8/2005 | Patel |
| 2005/0214356 A1 | 9/2005 | Joyce |
| 2006/0018912 A1 | 1/2006 | Finberg et al. |
| 2006/0051401 A1 | 3/2006 | Manohar et al. |
| 2006/0141164 A1 | 6/2006 | Akita et al. |
| 2006/0169975 A1 | 8/2006 | Noy et al. |
| 2006/0172318 A1 | 8/2006 | Medinz et al. |
| 2006/0275281 A1 | 12/2006 | Sullivan |
| 2006/0275371 A1 | 12/2006 | Dai et al. |
| 2007/0048383 A1 | 3/2007 | Helmus |
| 2007/0067882 A1 | 3/2007 | Atanasoska et al. |
| 2007/0190155 A1 | 8/2007 | Leary et al. |
| 2007/0200085 A1 | 8/2007 | Matsui et al. |
| 2007/0232699 A1 | 10/2007 | Russell et al. |
| 2008/0124281 A1 | 5/2008 | Gao et al. |
| 2009/0162277 A1 | 6/2009 | Ke et al. |
| 2011/0177154 A1* | 7/2011 | Bangera et al. ............ 424/450 |

FOREIGN PATENT DOCUMENTS

| | | |
|---|---|---|
| WO | WO 2005/069004 A2 | 7/2005 |
| WO | WO 2005/069750 A2 | 8/2005 |
| WO | WO 2008/066507 A2 | 6/2008 |

OTHER PUBLICATIONS

Brennan, John D.; "Preparation and Entrapment of Fluorescently Labeled Proteins for the Development of Reagentless Optical Biosensors"; 1999; pp. 295-312; vol. 9, No. 4; Plenum Publishing Corporation.

Bright et al.; "Regenerable Fiber-Optic-Based Immunosensor"; Analytical Chemistry; May 15, 1990; pp. 1065-1069; vol. 62, No. 10; American Chemical Society.

Brogden, Kim A.; "Antimicrobial Peptides: Pore Formers or Metabolic Inhibitors in Bacteria?"; Nature Reviews; Mar. 2005; pp. 238-250; vol. 3.

Cao et al.; "Molecular Beacon Aptamers for Protein Monitoring in Real-Time and in Homogeneous Solutions"; Current Proteomics; 2005; pp. 31-40; vol. 2, No. 1; Bentham Science Publishers Ltd.

Cato, Matthew H. et al.; Cell-Type Specific and Cytoplasmic Targeting of PEGylated Carbon Nanotube-Based Nanoassemblies; Journal of Nanoscience and Nanotechnology; bearing a date of 2008; pp. 2259-2269; vol. 8, No. 5; American Scientific Publishers.

Chakravarty et al.; "Thermal ablation of tumor cells with antibody-functionalized single-walled carbon nanotubes"; PNAS; Jun. 24, 2008; pp. 8697-8702; vol. 105; No. 25; The National Academy of Sciences of the USA.

Chen, Duan P.; "Bridging Natural Nano-Tubes With Designed Nanotubes"; pp. 161-174.

Chen et al.; "Aptamer from whole-bacterium SELEX as new therapeutic reagent against virulent *Mycobacterium tuberculosis*"; BBRC; 2007; pp. 743-748; vol. 357; Elsevier Inc.

Chen et al.; "Noncovalent functionalization of carbon nanotubes for highly specific electronic biosensors"; PNAS; Apr. 29, 2003; pp. 4984-4989; vol. 100, No. 9.

Chipuk et al.; "Mitochondrial outer membrane permeabilization during apoptosis: the innocent bystander scenario"; Cell Death and Differentiation; 2006; pp. 1396-1402; vol. 13; Nature Publishing Group.

Chung et al.; Size Comparisons among Integral Membrane Transport Protein Homologues in *Bacteria, Archaea, and Eucarya*; Feb. 2001; pp. 1012-1021; vol. 183, No. 3; American Society for Microbiology.

Dartois et al.; "Systemic Antibacterial Activity of Novel Synthetic Cyclic Peptides"; Aug. 2005; pp. 3302-3310; vol. 49, No. 8; American Society for Microbiology.

Dharap et al.; "Tumor-specific targeting of an anticancer drug delivery system by LHRH peptide"; Sep. 6, 2005; pp. 12962-12967; vol. 102, No. 36; The National Academy of Sciences of the USA.

Didenko et al.; "Horseradish peroxidase-driven fluorescent labeling of nanotubes with quantum dots"; BioTechniques; Mar. 2006; pp. 295-302; vol. 40, No. 3.

Elkin et al.; "Immuno-Carbon Nanotubes and Recognition of Pathogens"; ChemBioChem; 2005; pp. 640-643; vol. 6; Wiley-VCH Verlag GmbH & Co. KGaA, Weinheim.

Fan et al.; "Structures in *Bacillus subtilis* Are Recognized by CD14 in a Lipopolysaccharide Binding Protein-Dependent Reaction"; Infection and Immunity; Jun. 1999; pp. 2964-2968; vol. 67, No. 6; American Society for Microbiology.

Feazell et al.; "Soluble Single-Walled Carbon Nanotubes as Longboat Delivery Systems for Platinum(IV) Anticancer Drug Design"; J. Am. Chem. Soc.; 2007; pp. 8438-8439; vol. 129, No. 27; American Chemical Society.

Fenniri, Hicham et al.; "Entropically driven self-assembly of multichannel rosette nanotubes"; PNAS; bearing a date of Apr. 30, 2002; pp. 6487-6492; vol. 99, Suppl. 2; located at www.pnas.org/cgi/doi/10.1073/pnas.032527099.

Harrell et al.; "DNA-Nanotube Artificial Ion Channels"; J. Am. Chem. Soc.; 2004; pp. 15646-15647; vol. 126, No. 48; American Chemical Society.

Jhaveri et al.; "In vitro selection of signaling aptamers"; Nature Biotechnology; Dec. 2000; pp. 1293-1297; vol. 18; Nature America Inc.

Joseph et al.; "Ion Channel based biosensors: Ionic transport in carbon nanotubes"; Nanotech; 2003; pp. 1-4; vol. 1.

Kam et al.; "Carbon Nanotubes as Intracellular Transporters for Proteins and DNA: An Investigation of the Uptake Mechanism and Pathway"; Angew. Chem. Int. Ed.; 2005; pp. 1-6; vol. 44; Wiley-VCH Verlag GmbH & Co. KGaA, Weinheim.

Kam et al.; "Nanotube Molecular Transporters: Internalization of Carbon Nanotube-Protein Conjugates into Mammalian Cells"; J. Am. Chem. Soc.; 2004; pp. 6850-6851; vol. 126, No. 22; American Chemical Society.

Kam et al.; "Carbon nanotubes as multifunctional biological transporters and near-infrared agents for selective cancer cell destruction"; PNAS; Aug. 16, 2005; pp. 11600-11605; vol. 102, No. 33; The National Academy of Sciences of the USA.

Kang et al.; "Single-Walled Carbon Nanotubes Exhibit Strong Antimicrobial Activity"; Langmuir; 2007; pp. 8670-8673; vol. 23, No. 17; American Chemical Society.

Ke et al.; "Carbon nanomaterials in biological systems"; Journal of Physics: Condensed Matter; 2007; pp. 1-25; vol. 19; IOP Publishing Ltd.

Khandare et al.; "Novel Polymeric Prodrug with Multivalent Components for Cancer Therapy"; The Journal of Pharmacology and Experimental Therapeutics; 2006; pp. 929-937; vol. 317, No. 3; The American Society for Pharmacology and Experimental Therapeutics.

Kim et al.; "Oriented Self-Assembly of Cyclic Peptide Nanotubes in Lipid Membranes"; J. Am. Chem. Soc.; 1998; pp. 4417-4424; vol. 120, No. 18; American Chemical Society.

Knappik et al.; "Fully Synthetic Human Combinatorial Antibody Libraries (HuCAL) Based on Modular Consensus Frameworks and CDRs Randomized with Trinucleotides"; J. Mol. Biol.; 2000; pp. 57-86; vol. 296; Academic Press.

Koo et al.; "Development of a Streptavidin-Conjugated Single-Chain Antibody That Binds *Bacillus cereus* Spores"; Applied and Environmental Microbiology; Jul. 1998; pp. 2497-2502; vol. 64, No. 7; American Society for Microbiology.

Krag et al.; "Selection of Tumor-binding Ligands in Cancer Patients with Phage Display Libraries"; Cancer Res 2006; Aug. 1, 2006; pp. 7724-7733; vol. 66, No. 15; American Association for Cancer Research.

Kroemer et al.; "Mitochondrial Membrane Permeabilization in Cell Death"; Physiol Rev; Jan. 2007; pp. 99-163; vol. 87; American Physiological Society.

Kumar et al.; "Carbon Nanotubes from Camphor: An Environment-Friendly Nanotechnology"; Journal of Physics: Conference Series; 2007; pp. 643-646; vol. 61; IOP Publishing Ltd.

(56) References Cited

OTHER PUBLICATIONS

Kupper et al.; "Generation of human antibody fragments against *Streptococcus mutans* using a phage display chain shuffling approach"; BMC Biotechnology; 2005; pp. 1-12; vol. 5, No. 4; BioMed Central Ltd.

Lee et al.; "Self-Assembly of Biocidal Nanotubes from a Single-Chain Diacetylene Amine Salt"; J. Am. Chem. Soc.; 2004; pp. 13400-13405; vol. 126, No. 41; American Chemical Society.

Li et al.; "Carboxyl-modified single-walled carbon nanotubes selectively induce human telomeric i-motif formation"; PNAS; Dec. 26, 2006; pp. 19658-19663; vol. 103, No. 52; The National Academy of Sciences of the USA.

Lichlyter et al.; "Development of a novel Fret immunosensor technique"; Biosensors and Bioelectronics; 2003; pp. 219-226; vol. 19; Elsevier B.V.

Lin et al.; "Detection of phospholipid-carbon nanotube translocation using fluorescence energy transfer"; Applied Physics Letters; 2006; pp. 143118-1 to 143118-3 vol. 89; American Institute of Physics.

Lopez et al.; "Understanding nature's design for a nanosyringe"; PNAS; Mar. 30, 2004; pp. 4431-4434; vol. 101, No. 13; The National Academy of Sciences of the USA.

Liu et al.; "Supramolecular Chemistry on Water-Soluble Carbon Nanotubes for Drug Loading and Delivery"; $^{ACS}$ NANO; 2007; pp. 50-56; vol. 1, No. 1; American Chemical Society.

Lyonnais et al.; "DNA-Carbon Nanotube Conjugates Prepared by a Versatile Method Using Streptavidin-Biotin Recognition"; small; 2008; pp. 442-446; vol. 4, No. 4; Wiley-VCH Verlag GmbH & Co. KGaA, Weinheim.

Matsushita et al.; "Photo-acceleration of protein release from endosome in the protein transduction system"; FEBS Letters; 2004; pp. 221-226; vol. 572; Elsevier B.V. on behalf of the Federation of European Biochemical Societies.

McDevitt et al.; "Tumor Targeting with Antibody-Functionalized, Radiolabeled Carbon Nanotubes"; The Journal of Nuclear Medicine; Jul. 2007; pp. 1180-1189; vol. 48, No. 7; Society of Nuclear Medicine, Inc.

Moghimi et al.; "Nanomedicine: current status and future prospects"; The FASEB Journal; Mar. 2005; pp. 311-330; vol. 19.

Pantarotto et al.; "Synthesis, Structural Characterization, and Immunological Properties of Carbon Nanotubes Functionalized with Peptides"; J. Am. Chem. Soc.; 2003; pp. 6160-6164; vol. 125, No. 20; American Chemical Society.

Park et al.; "Single-walled Carbon Nanotubes Are a New Class of Ion Channel Blockers"; The Journal of Biological Chemistry; Sep. 30, 2003; pp. 50212-50216; vol. 278, No. 50; Issue of Dec. 12; The American Society for Biochemistry and Molecular Biology, Inc.

Peppas et al.; "Polymers and Gels as Molecular Recognition Agents"; Pharmaceutical Research; May 2002; pp. 578-587; vol. 19, No. 5; Plenum Publishing Corporation.

Reches et al.; "Molecular Self-Assembly of Peptide Nanostructures: Mechanism of Association and Potential Uses"; Current Nanoscience; 2006; pp. 105-111; vol. 2, No. 2; Bentham Science Publishers Ltd.

Reches, Meital et al.; "Biological and Chemical Decoration of Peptide Nanostructures via Biotin-Avidin Interactions"; Journal of Nanoscience and Nanotechnology; bearing a date of 2007; pp. 2239-2245; vol. 7, No. 7; American Scientific Publishers.

Schultz, Carsten et al.; "Acetoxymethyl Esters of Phosphates, Enhancement of the Permeability and Potency of cAMP*"; The Journal of Biological Chemistry; bearing a date of Jul. 29, 1992; pp. 6316-6322; vol. 268, No. 9; The American Society for Biochemistry and Molecular Biology, Inc.; located at www.jbc.org.

Seo et al.; "FeCo/graphitic-shell nanocrystals as advanced magnetic-resonance-imaging and near-infrared agents"; Nature Materials; Dec. 2006; pp. 971-976 including Supplementary Information pp. S1-S3; vol. 5; Nature Publishing Group.

Shangguan et al.; "Aptamers evolved from live cells as effective molecular probes for cancer study"; PNAS; Aug. 8, 2006; pp. 11838-11843; vol. 103, No. 32; The National Academy of Sciences of the USA.

Singh et al.; "Tissue biodistribution and blood clearance rates of intravenously administered carbon nanotube radiotracers"; PNAS, Feb. 28, 2006; pp. 3357-3362; vol. 103, No. 9; The National Academy of Sciences of the USA.

Sitharaman et al.; "Gadonanotubes as new high-performance MRI contrast agents"; International Journal of Nanomedicine; 2006; pp. 291-295; vol. 1, No. 3; Dove Medical Press Limited.

So et al.; "Single-Walled Carbon Nanotube Biosensors Using Aptamers as Molecular Recognition Elements"; J. Am. Chem. Soc.; 2005, pp. 11906-11907; vol. 127, No. 34; American Chemical Society.

Spear et al.; "Isolation, characterization, and recovery of small peptide phage display epitopes selected against viable malignant glioma cells"; Cancer Gene Therapy; 2001; pp. 506-511; vol. 8, No. 7; Nature Publishing Group.

Suri, Sarabjeet Singh et al.; "Nanotechnology-based drug delivery systems"; Journal of Occupational Medicine and Toxicology; bearing a date of Dec. 1, 2007; pp. 1-6; vol. 2:16; BioMed Central.

Verma, Ayush et al.; "Surface-structure-regulated cell-membrane penetration by monolayer-protected nanoparticles"; Nature Publishing Group; bearing a date of May 25, 2008; pp. 1-8; located at www.nature.com/naturematerials.

Wang et al.; "APD: the Antimicrobial Peptide Database"; Nucleic Acids Research; 2004; pp. D590-D592; vol. 32; Database issue; Oxford University Press.

Wang et al.; "Precise cutting of single-walled carbon nanotubes"; Nanotechnology; 2007; pp. 1-6; vol. 18; IOP Publishing Ltd.

Welsher et al.; "Selective Probing and Imaging of Cells with Single Walled Carbon Nanotubes as Near-Infrared Fluorescent Molecules"; Nano Letters; 2008; pp. 586-690 including Supplementary Information pp. 1-3; vol. 8, No. 2; American Chemical Society.

Ye et al.; "Molecularly imprinted polymers as antibody and receptor mimics for assays, sensors and drug discovery"; Anal Bioanal Chem; 2004; pp. 1887-1897; vol. 378.

Yoshikawa et al.; "Organelle-Targeted Delivery of Biological Macromolecules Using the Protein Transduction Domain: Potential Applications for Peptide Aptamer Delivery into the Nucleus"; J. Mol. Biol.; 2008; pp. 777-782; vol. 380; Elsevier Ltd.

Zhou, Yong; "Patenting Activity in Synthesis of Lipid Nanotubes and Peptide Nanotubes"; Recent Patents on Nanotechnology; 2007; pp. 21-28; vol. 1, No. 1; Bentham Science Publishers Ltd.

Ambudkar et al.; "A Novel Way to Spread Drug Resistance in Tumor Cells: Functional Intercellular Transfer of P-Glycoprotein (ABCB1)"; Trends in Pharmacological Sciences; dated Aug. 2005, available online Jun. 22, 2005; pp. 385-387; vol. 26, No. 8; Elsevier.

Korneva et al.; "Carbon Nanotubes Loaded with Magnetic Particles"; Nano Letters; dated May 2005, available online Mar. 30, 2005; pp. 879-884; vol. 5, No. 5; American Chemical Society.

Salvador-Morales et al.; "Complement Activation and Protein Adsorption by Carbon Nanotubes"; Molecular Immunology; dated Feb. 2006, available online Mar. 16, 2005; pp. 193-201; vol. 43; Elsevier Ltd.

Wang et al.; "Characterization of Micropatterned Lipid Membranes on a Gold Surface by Surface Plasmon Resonance Imaging and Electrochemical Signaling of a Pore-Forming Protein"; Langmuir; dated Nov. 8, 2005, available online Oct. 12, 2005; pp. 10292-10296; vol. 21, No. 23; American Chemical Society.

PCT International Search Report; International App. No. PCT/US 09/05111; bearing a date of Jan. 25, 2010; pp. 1-2.

PCT International Search Report; International App. No. PCT/US 09/05112; bearing a date of Jan. 21, 2010; pp. 1-4.

Cans et al., "Artificial cells: Unique insights into exocytosis using liposomes and lipid nanotubes"; PNAS; Jan. 21, 2003; pp. 400-404; vol. 100, No. 2.

Chekmenev et al.; "Flow-Through Lipid Nanotube Arrays for Structure-Function Studies of Membrane Proteins by Solid-State NMR Spectroscopy"; Biophysical Journal; bearing a date of Oct. 2006; pp. 3076-3084; vol. 91; The Biophysical Society.

(56) References Cited

OTHER PUBLICATIONS

Extended European Search Report, Pursuant to Rule 62 EPC; App. No. EP 09 81 3375; Aug. 1, 2013 (received by our Agent on Aug. 8, 2013); pp. 1-8.
Ghadiri et al.; "Artificial transmembrane ion channels from self-assembling peptide nanotubes"; Nature, Letters to Nature; May 26, 1994; pp. 301-304; vol. 369.
Joseph et al.; "Electrolytic Transport in Modified Carbon Nanotubes"; Nano Letters; Aug. 8, 2003; pp. 1399-1403; vol. 3, No. 10; American Chemical Society.
Chen et al.; "Solution Properties of Single-Walled Carbon Nanotubes"; Science; Oct. 2, 1998; pp. 94-98; vol. 282, No. 95; located at www.sciencemag.org.
Xu et al.; "Condensed Multiwalled Carbon Nanotubes as Super Fibers"; Jun. 5, 2006; pp. 1-10; located at: http://arxiv.org/pdf/cond-mat/0606105v1.pdf.
Hoshino et al.; "Use of fluorescent quantum dot bioconjugates for cellular imaging of immune cells, cell organelle labeling, and nanomedicine: surface modification regulates biological function, including cytotoxicity"; J. Artif. Organs; Jan. 31, 2007; pp. 149-157; vol. 10; The Japanese Society for Artificial Organs.

\* cited by examiner

TUBULAR NANOSTRUCTURE TARGETED TO CELL MEMBRANE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC§119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation of U.S. patent application Ser. No. 12/283,907, entitled TUBULAR NANOSTRUCTURE TARGETED TO CELL MEMBRANE, naming Mahalaxmi Gita Bangera, Ed Harlow, Roderick A. Hyde, Muriel Y. Ishikawa, Edward K.Y. Jung, Eric C. Leuthardt, Nathan P. Myhrvold, Dennis J. Rivet, Elizabeth A. Sweeney, Clarence T. Tegreene, Lowell L. Wood, Jr. and Victoria Y.H. Wood as inventors, filed 15 Sep. 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/283,908, entitled TUBULAR NANOSTRUCTURE TARGETED TO CELL MEMBRANE, naming Mahalaxmi Gita Bangera, Ed Harlow, Roderick A. Hyde, Muriel Y. Ishikawa, Edward K.Y. Jung, Eric C. Leuthardt, Nathan P. Myhrvold, Dennis J. Rivet, Elizabeth A. Sweeney, Clarence T. Tegreene, Lowell L. Wood, Jr. and Victoria Y.H. Wood as inventors, filed 15 Sep. 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at www.uspto.gov/web/offices/comlsol/og/2003/week11/patbene.htm.

The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

Devices, compositions, and methods described herein provide a tubular nanostructure targeted to a lipid bilayer membrane. The targeted tubular nanostructure can have a hydrophobic surface region flanked by two hydrophilic surface regions. The tubular nanostructure is configured to interact with a lipid bilayer membrane and form a pore in the lipid bilayer membrane. The tubular nanostructure may be targeted by including at least one ligand configured to bind to one or more cognates on the lipid bilayer membrane of a target cell, for example, on a tumor cell, an infected cell, or a diseased cell in a subject. The tubular nanostructure can form a pore in the lipid bilayer membrane which can permit transit or translocation of at least one compound across the membrane and cause cell death of the target cell.

Devices, compositions, and methods described herein provide a tubular nanostructure targeted to a lipid bilayer membrane. The targeted tubular nanostructure can have a hydrophobic surface region flanked by two hydrophilic surface regions. The tubular nanostructure is configured to interact with a lipid bilayer membrane and form a pore in the lipid bilayer membrane. The tubular nanostructure may be targeted by including at least one ligand configured to bind to one or more cognates on the lipid bilayer membrane of a target cell, for example, on a tumor cell, an infected cell, or a diseased cell in a subject. The tubular nanostructure can form a pore in the lipid bilayer membrane which can permit transit or translocation of at least one compound across the membrane and cause cell death of the target cell.

A tubular nanostructure is provided which includes a hydrophobic surface region flanked by two hydrophilic surface regions configured to form a pore in a lipid bilayer membrane, and at least one ligand configured to bind one or more cognates on the membrane. The nanostructure includes, but is not limited to, one or more of a carbon nanotube, cyclic peptide nanotube, crown ether nanotube, polymer nanotube, polymer/carbon nanotube, DNA nanotube, or inorganic nanotube. The inorganic nanotube further includes, but is not limited to, a boron nitride nanotube. The polymer nanotube includes, but is not limited to, polystyrene, polytetrafluoroethylene, polymethylmethacrylate, polyaniline, or poly-L-lactide/palladium acetate. The polymer/carbon nanotube includes, but is not limited to, a polyaniline/carbon nanotube. The hydrophobic surface region includes, but is not limited to, a single wall carbon nanotube surface region. The hydrophilic surface region includes, but is not limited to, one or more of amines, amides, charged or polar amino acids, alcohols, carboxylic groups, oxides, ester groups, ether groups, or ester-ether groups, ketones, aldehydes, or derivatives thereof. The one or more cognates include, but are not limited to, one or more cell surface receptors or cell surface markers in the lipid bilayer membrane. The one or more cognates include, but are not limited to, at least one of a protein, a carbohydrate, a glycoprotein, a glycolipid, a sphingolipid, a glycerolipid or a metabolite thereof. One or both of the hydrophilic surface regions may be at the end of the nanostructure. The nanostructure may have a length of about 1 nm to about 1500 nm, or a length of about 20 Å to about 40 Å. The nanostructure may have a diameter of about 0.5 nm to about 5 nm or a diameter of about 5 Å to about 20 Å. The at least one ligand includes, but is not limited to, at least a portion of an antibody, antibody-coated liposome, polynucleotide, polypeptide, receptor, viral plasmid, polymer, protein, small chemical compound, carbohydrate, lipid, toxin, pore-forming toxin, or lectin. The at least one ligand includes a therapeutic compound configured to affect a cell or process, or to treat at least one of a disease, condition, or symptom. The nanostructure may further include at least one second ligand configured to bind one or more cognates on the lipid bilayer membrane. The tubular nanostructure induces cell death.

The nanostructure may further include one or more elements to control transport of molecules through the tubular nanostructure. In one aspect, the one or more elements are on the extracellular end of the nanostructure. In a further aspect, the one or more elements are on the cytoplasmic end of the nanostructure. The one or more elements may include a hydrophilic inner liner of the tubular nanostructure. The one or more elements further includes at least one second ligand configured to reversibly bind a cognate of interest, wherein the cognate of interest passes through the pore. The at least one second ligand includes, but is not limited to, a monospecific antibody or a bispecific antibody. The one or more elements may reversibly block the pore. The one or more elements includes, but is not limited to, a magnetic entity or a molecular entity. The molecular entity includes, but is not limited to, at least a portion of a carbon nanostructure, polynucleotide, polypeptide, antibody, receptor, glycoprotein, lipid, polysaccharide, or polymer. The one or more elements may include a charged group. The one or more elements may be passive or active. In one aspect, the pore permits transit or translocation of at least one compound across the membrane. The one or more active elements includes, but is not limited to, at least one of an ATPase transport element, $Na^+K^+$ ATPase, $H^+K^+$ ATPase, or $Ca^{2+}$ ATPase. The one or more active elements further includes, but is not limited to, at least one of an ABC transporter element, CFTR transporter, TAP transporter, or liver cell transporter. The one or more active elements further includes, but is not limited to, at least one of a symport pump, $Na^+$/iodide transporter, *E. coli* permease, or an antiport pump.

The nanostructure may further include a marker attached to the nanostructure. The marker includes, but is not limited to, a fluorescent marker, a radioactive marker, quantum dot, metal, or magnetic resonance imaging marker. The marker may be activated by anchoring in the membrane. The marker may be activated by a ligand reaction. The marker may be activated by interaction with a hydrophobic medium. The hydrophobic surface region may be extended in diameter. The hydrophobic surface region may be extended in diameter by a disk, a stub, or a graphene sheet.

A composite tubular nanostructure includes two or more nanotubes wherein at least one nanotube includes a hydrophobic surface region, each hydrophobic surface region flanked by two hydrophilic surface regions configured to form a pore in a lipid bilayer membrane. The composite tubular nanostructure may further include at least one ligand configured to bind one or more cognates on the lipid bilayer membrane. The two or more ligands may be configured to bind to the one or more cognates on the lipid bilayer membrane. The composite tubular nanostructure may further include three or more nanotubes. The composite tubular nanostructure may further include at least one nanotube includes a completely hydrophobic surface region. The at least one nanotube including the completely hydrophobic surface region may be surrounded by at least six nanotubes including the hydrophobic surface region flanked by two hydrophilic surface regions configured to form the pore in the lipid bilayer membrane. The at least two of the nanotubes may have different diameters. The at least two of the nanotubes may have different lengths. The nanotubes may be substantially parallel. The nanotubes may be substantially orthogonal. The composite tubular nanostructure includes, but is not limited to, at least one of the two or more nanotubes is a carbon nanotube, cyclic peptide nanotube, crown ether nanotube, polymer nanotube, polymer/carbon nanotube, DNA nanotube, or inorganic nanotube. The inorganic nanotube further includes, but is not limited to, a boron nitride nanotube. The polymer nanotube includes, but is not limited to, polystyrene, polytetrafluoroethylene, polymethylmethacrylate, polyaniline, or poly-L-lactide/palladium acetate. The polymer/carbon nanotube includes, but is not limited to, a polyaniline/carbon nanotube. The hydrophobic surface region includes, but is not limited to, a single wall carbon nanotube surface region. The hydrophilic surface region includes, but is not limited to, one or more of amines, amides, charged or polar amino acids, alcohols, carboxylic groups, oxides, ester groups, ether groups, or ester-ether groups, ketones, aldehydes, or derivatives thereof. The one or more cognates include, but are not limited to, one or more cell surface receptors or cell surface markers in the lipid bilayer membrane. The one or more cognates include, but are not limited to, at least one of a protein, a carbohydrate, a glycoprotein, a glycolipid, a sphingolipid, a glycerolipid or a metabolite thereof. One or both of the hydrophilic surface regions may be at the end of the nanostructure. The nanostructure may have a length of about 1 nm to about 1500 nm, or a length of about 20 Å to about 40 Å. The nanostructure may have a diameter of about 0.5 nm to about 5 nm or a diameter of about 5 Å to about 20 Å. The at least one ligand includes, but is not limited to, at least a portion of an antibody, antibody-coated liposome, polynucleotide, polypeptide, receptor, viral plasmid, polymer, protein, small chemical compound, carbohydrate, lipid, toxin, pore-forming toxin, or lectin. The at least one ligand includes a therapeutic compound configured to affect a cell or process, or to treat at least one of a disease, condition, or symptom. The nanostructure may further include at least one second ligand configured to bind one or more cognates on the lipid bilayer membrane. The two or more ligands may be configured to bind to the one or more cognates on the lipid bilayer membrane. The composite tubular nanostructure may further include a therapeutic composition to treat a disease, symptom, or condition. The therapeutic composition includes, but is not limited to, a cytotoxic agent or antimicrobial agent.

The composite tubular nanostructure may further include one or more elements to control transport of molecules through the tubular nanostructure. In one aspect, the one or more elements are on the extracellular end of the nanostructure. In a further aspect, the one or more elements are on the cytoplasmic end of the nanostructure. The one or more elements may include a hydrophilic inner liner of the tubular nanostructure. The one or more elements further includes a ligand. The one or more elements may include a charged group. The one or more elements may be passive or active. The one or more elements may have different transport properties. The one or more active elements includes, but is not limited to, at least one of an ATPase transport element, $Na^+K^+$ ATPase, $H^+K^+$ ATPase, or $Ca^{2+}$ ATPase. The one or more active elements further includes, but is not limited to, at least one of an ABC transporter element, CFTR transporter, TAP transporter, or liver cell transporter. The one or more active elements further includes, but is not limited to, at least one of a symport pump, Na$^+$/iodide transporter, *E. coli* permease, or an antiport pump. In one aspect, the pore permits transit or translocation of at least one compound across the membrane. The nanostructure may further include a marker attached to the nanostructure. The marker includes, but is not limited to, a fluorescent marker, a radioactive marker, quantum dot, metal, or magnetic resonance imaging marker. The marker may be activated by anchoring in the membrane. The marker may be activated by a ligand reaction. The marker may be activated by interaction with a hydrophobic medium. In one aspect, the cognate includes one or more cell surface receptors or cell surface markers on a neoplastic cell or an infected cell A method for inserting a tubular nanostructure into a lipid bilayer membrane is provided which includes applying to a lipid bilayer membrane, a tubular nanostructure including a hydrophobic surface region flanked by two hydrophilic surface regions configured to form a pore in the lipid bilayer membrane and including at least one ligand configured to bind one or more cognates on the membrane, under conditions and for time sufficient to allow the nanostructure to penetrate the membrane. In one aspect, one or both of the hydrophilic regions of the nanostructure is located substantially at an end of the tubular nanostructure. The tubular nanostructure includes, but is not limited to, a carbon nanotube, cyclic peptide nanotube, crown ether nanotube, polymer nanotube, polymer/carbon nanotube, DNA nanotube, or inorganic nanotube. The hydrophilic regions of the tubular body include, but are not limited to, one or more of amines, amides, charged or polar amino acids, alcohols, carboxylic groups, ester groups, oxides, ether groups, ester-ether groups, ketones, aldehydes, or derivatives thereof. In one aspect, the tubular nanostructure is assisted in crossing the membrane core by lipid molecules from the membrane. In a further aspect, the lipid molecules assisting the tubular nanostructure in crossing the membrane undergo lipid translocation across a bilayer leaflet.

A method for providing a stable pore in a lipid bilayer membrane is provided which includes positioning across a lipid bilayer membrane a tubular nanostructure including a hydrophobic surface region flanked by two hydrophilic surface regions configured to form a pore in the lipid bilayer membrane and including at least one ligand configured to bind one or more cognates on the membrane. The one or more of the hydrophilic regions of the tubular nanostructure may be located at an end of a tubular nanostructure. In one aspect, the both hydrophilic regions may be located at opposite ends of a tubular nanostructure. In one aspect, positioning the tubular nanostructure across the lipid bilayer membrane induces cell death. The lipid bilayer membrane may be on a neoplastic cell or an infected cell.

A method for inserting a tubular nanostructure into a lipid bilayer membrane is provided which includes applying to a lipid bilayer membrane a composite tubular nanostructure including two or more nanotubes wherein at least one nanotube includes a hydrophobic surface region flanked by two hydrophilic surface regions configured to form a pore in a lipid bilayer membrane, under conditions and for time sufficient to allow the composite nanostructure to penetrate the membrane. The hydrophobic region of at least one of the two or more nanotubes may be located at the ends of a tubular body. The hydrophilic regions may be located at the ends of the at least one nanotube. The tubular nanostructure may include a composite nanostructure of three or more nanotubes. The composite tubular nanostructure may further include at least one nanotube includes a completely hydrophobic surface region. The at least one nanotube including the completely hydrophobic surface region may be surrounded by at least six nanotubes including the hydrophobic surface region flanked by two hydrophilic surface regions configured to form the pore in the lipid bilayer membrane. The at least two of the nanotubes may have different diameters. The at least two of the nanotubes may have different lengths. The tubular nanostructure may be assisted in crossing the membrane core by lipid molecules from the membrane. The lipid molecules assisting the tubular nanostructure in crossing the membrane may undergo lipid translocation across a bilayer leaflet.

A method for providing a pore in a lipid bilayer membrane includes positioning across a lipid bilayer membrane a composite tubular nanostructure including two or more nanotubes wherein at least one nanotube includes a hydrophobic surface region flanked by two hydrophilic surface regions configured to form a pore in a lipid bilayer membrane. The hydrophilic regions may be located at opposite ends of the at least one nanotubes. The tubular nanostructure may be positioned across the lipid bilayer membrane induces cell death. The lipid bilayer membrane may be on a neoplastic cell or an infected cell. The tubular nanostructure may be assisted in crossing the membrane core by lipid molecules from the membrane. The lipid molecules assisting the tubular nanostructure in crossing the membrane may undergo lipid translocation across a bilayer leaflet.

A method for disrupting a lipid bilayer membrane of a cell is provided which includes contacting the cell with at least one tubular nanostructure including a hydrophobic surface region flanked by two hydrophilic surface regions configured to form a pore in the lipid bilayer membrane and including at least one ligand configured to bind one or more cognates on the lipid bilayer membrane of the cell. Two or more ligands may be configured to bind to the one or more cognates on the lipid bilayer membrane. The at least one tubular nanostructure may be positioned across the lipid bilayer membrane induces cell death. The cell may be a neoplastic cell or an infected cell.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
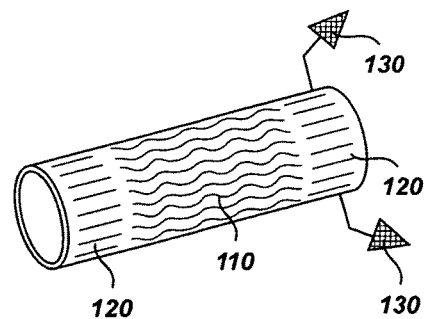
FIGS. 1A, 1B, 1C and 1D depict a diagrammatic view of one aspect of an exemplary embodiment of a tubular nanostructure and a method for inserting a tubular nanostructure into a lipid bilayer membrane of a cell.
Figure 1B:
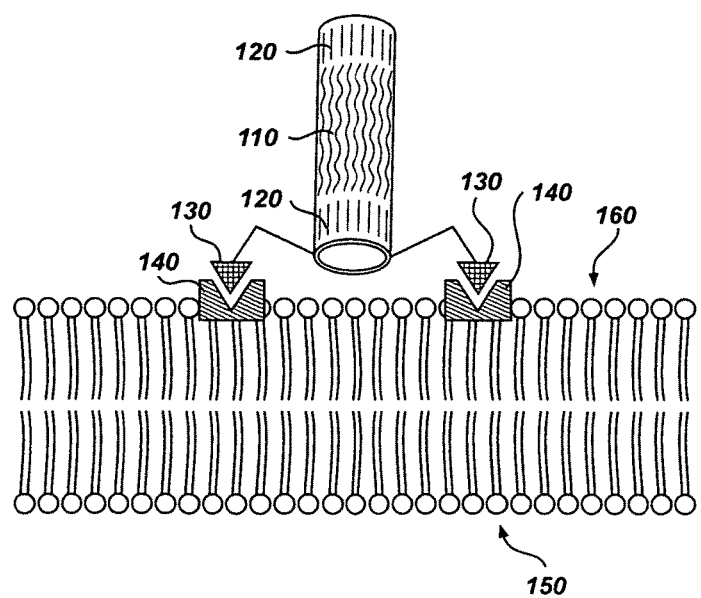
Figure 1C:
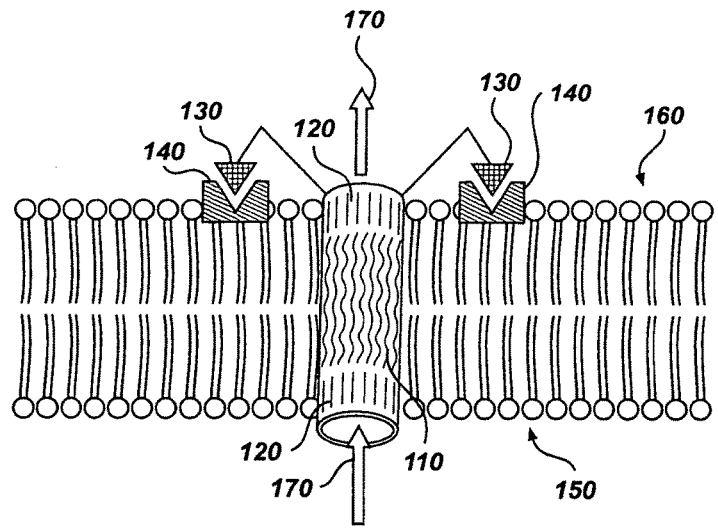
Figure 1D:
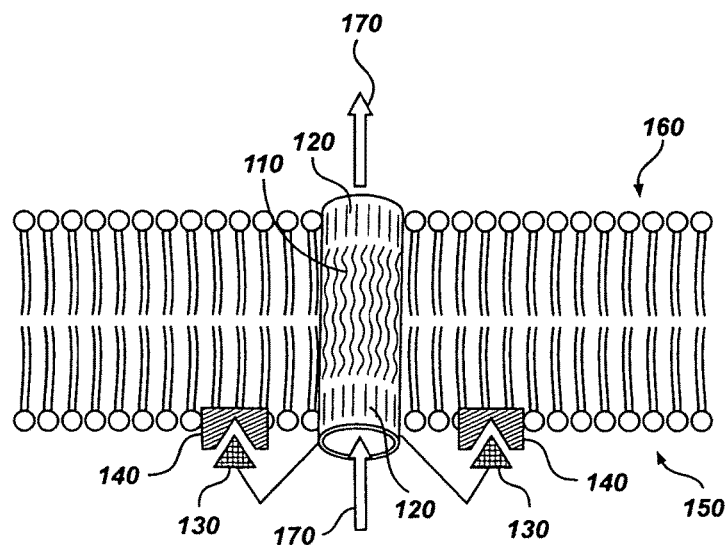
Figure 2A:
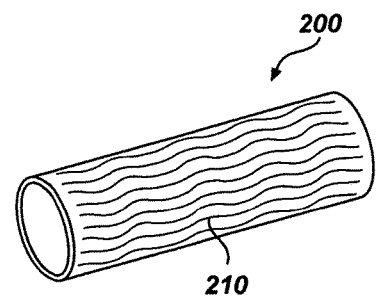
FIGS. 2A, 2B, 2C, 2D, and 2E depict a diagrammatic view of one aspect of an exemplary embodiment of a tubular nanostructure and a method for inserting a tubular nanostructure into a lipid bilayer membrane of a cellular organelle.
Figure 2B:
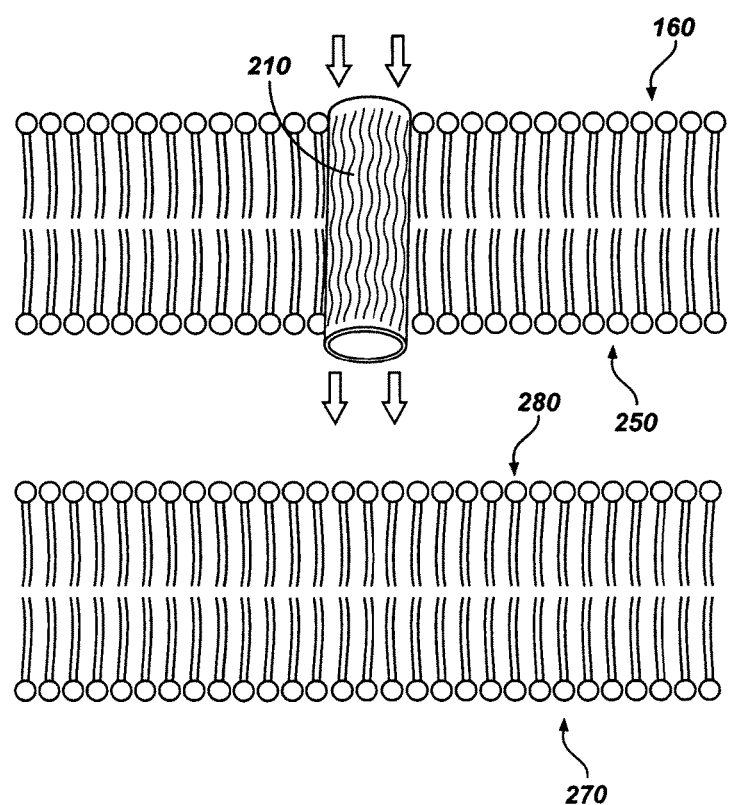
Figure 2C:
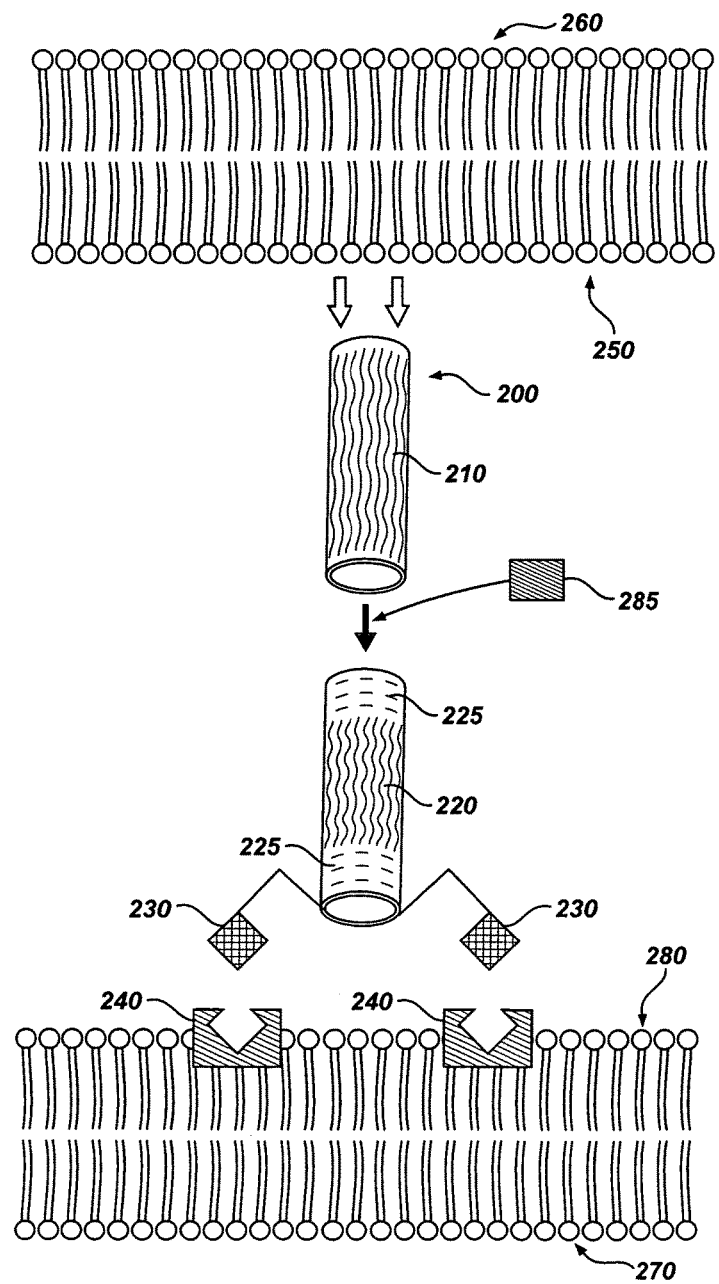
Figure 2D:
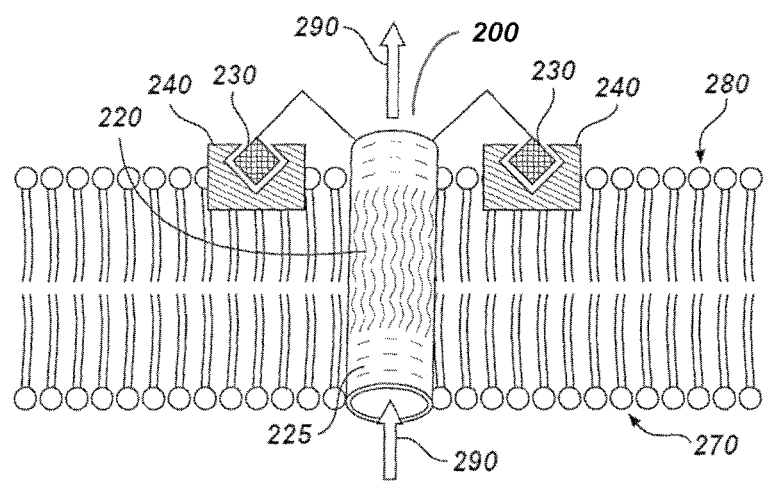
Figure 2E:
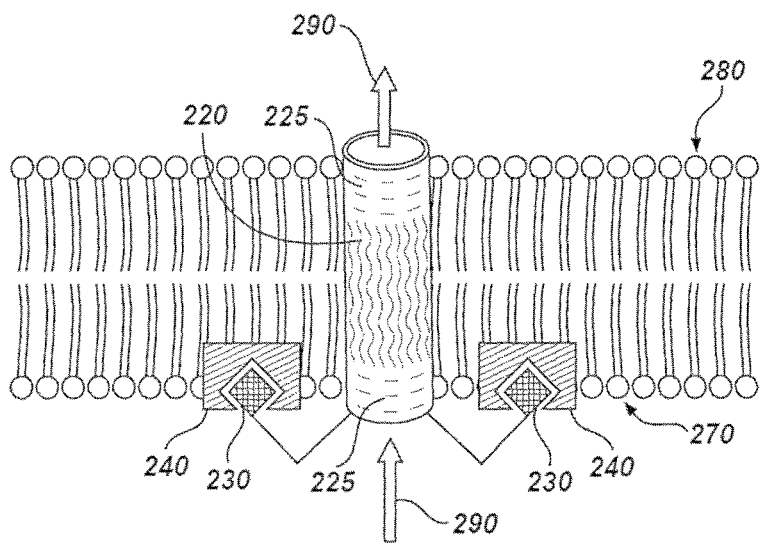

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings; and/or descriptions of single topics may span two or more topic headings). Hence, the use of the formal outline headings is not intended to be in any way limiting.

Devices, compositions, and methods described herein provide a tubular nanostructure targeted to a lipid bilayer membrane. The targeted tubular nanostructure can have a hydrophobic surface region flanked by two hydrophilic surface regions. The tubular nanostructure is configured to interact with a lipid bilayer membrane and form a pore in the lipid bilayer membrane. The tubular nanostructure may be targeted by including at least one ligand configured to bind to one or more cognates on the lipid bilayer membrane of a target cell, for example, on a tumor cell, an infected cell, or a diseased cell in a subject. The tubular nanostructure can form a pore in the lipid bilayer membrane which can permit transit or translocation of at least one compound across the membrane and cause cell death of the target cell.

At least one ligand includes a compound that binds a cognate and can be at least a portion of an antibody, antibody-coated liposome, polynucleotide, polypeptide, receptor, viral plasmid, polymer, protein, carbohydrate, lipid, toxin, lectin, pore-forming toxin, small chemical compound, or any combination thereof. In one aspect, the ligand can be a therapeutic compound configured to affect a cell or process or to treat at least one of a disease, condition, or symptom One or more cognates can be associated with a target cell or organelle and may include, but is not limited to, at least one of a protein, a carbohydrate, a glycoprotein, a glycolipid, a sphingolipid, a glycerolipid, or metabolites thereof. The cognate can be a cell surface receptor or a cell surface marker on the lipid bilayer membrane of a target cell, for example, on a tumor cell, an infected cell, or a diseased cell in a subject, or on a bacterial cell or a parasite cell.

Ligands can be targeted to cognates which are associated with lipid bilayer membranes of target cells and/or organelles. A target cell may include a tumor cell and/or other diseased cell type in a mammalian subject. A target cell may also include a pathogen, e.g., bacteria, fungi, and/or parasites. In some instances, the tubular nanostructures may be designed to target a specific cellular organelle, e.g., the mitochondria. The tubular nanostructure can include a surface region configured to pass through a lipid bilayer membrane of a cell, a hydrophobic surface region flanked by two hydrophilic surface regions configured to form a pore in a lipid bilayer membrane of a cellular organelle, and at least one ligand configured to bind one or more cognates on the lipid bilayer membrane of the cellular organelle.

The tubular nanostructure includes, but is not limited to, one or more of a carbon nanotube, cyclic peptide nanotube, crown ether nanotube, polymer nanotube, polymer/carbon nanotube, DNA nanotube, or inorganic nanotube. The inorganic nanotube can include a boron nitride nanotube. The polymer nanotube can include polystyrene, polytetrafluoroethylene, polymethylmethacrylate, polyaniline, or poly-L-lactide/palladium acetate. The polymer/carbon nanotube can include a polyaniline/carbon nanotube. A single wall carbon nanotube can have a hydrophobic surface region at least a portion of, or all of, the surface structure of the tubular nanostructure.

A hydrophobic surface region of a tubular nanostructure includes a tubular nanostructure with a carbon surface structure and/or a linker molecule having a hydrophobic portion adsorbed onto the tubular nanostructure, e.g., a phospholipid. A hydrophobic polymer refers to any polymer resistant to wetting, or not readily wet, by water, i.e., having a lack of affinity for water. A hydrophobic polymer typically will have a surface free energy of about 40 dynes/cm ($10^{-5}$ Newtons/cm or N/cm) or less. Examples of hydrophobic polymers include, by way of illustration only, polylactide, polylactic acid, polyolefins, such as poylethylene, poly (isobutene), poly(isoprene), poly(4-methyl-1-pentene), polypropylene, ethylene-propylene copolymers, and ethylenepropylene-hexadiene copolymers; ethylene-vinyl acetate copolymers; styrene polymers, such as poly(styrene), poly (2-methylstyrene), styrene-acrylonitrile copolymers having less than about 20 mole-percent acrylonitrile, and styrene-2,2,3,3,-tetrafluoro-propyl methacrylate copolymers. Further examples are given in U.S. Pat. No. 6,673,447, hereby incorporated by reference.

A hydrophilic surface region of a tubular nanostructure includes a tubular nanostructure with a surface structure, e.g., a carbon surface structure, and/or a linker molecule having a hydrophilic portion adsorbed onto the tubular nanostructure, e.g., polyethylene glycol (PEG). The hydrophilic surface region may include one or more of amines, amides, charged or polar amino acids, alcohols, carboxylic groups, oxides, ester groups, ether groups, or ester-ether groups, ketones, aldehydes, or derivatives thereof. In one aspect, the hydrophilic surface region includes PEG, which refers to a polymer with the structure ($—CH_2CH_2O—$)$_n$ that is synthesized normally by ring opening polymerization of ethylene oxide. The PEG will impart water (and serum) solubility to the hydrophobic nanoparticle and lipid portion of the polar lipid. The polymer is usually linear at molecular weights (MWs) less than or equal to 10 kD. The PEG will have an MW below 5,400, preferably below 2,000, or about 45 repeating ethylene oxide units. However, the higher MW PEGs (higher "n" repeating units) may have some degree of branching. Polyethylene glycols of different MWs have already been used in pharmaceutical products for different reasons (e.g., increase in solubility of drugs). Therefore, from the regulatory standpoint, they are very attractive for further development as drug or protein carriers. The PEG used here should be attached to the nanoparticles at a density adjusted for the PEG length. For example, with PL-PEG 2000, we have an estimate of 4 nm spacing between PEG chain along the tube. At this spacing, PEG5400 is too long and starts to block interaction with cell surface. For PEG at approximately 1 nm distance, the PEG MW should be less than about 200, to allow hydrophobicity.

In some instances, the one or more tubular nanostructures may be functionalized with one or more ligands, therapeutic compounds, toxin, marker, or combinations thereof. The functionalized component may be a small chemical compound. Small chemical compounds that might be added to a tubular nanostructure include, but are not limited to, targeting biomolecules, e.g., receptor binding ligands; therapeutic biomolecules, e.g., therapeutic small chemical compound drugs; toxins, e.g., chemotherapy agents; and markers, e.g., fluorescent dyes and/or radioactive compounds. Any of a number of homobifunctional, heterofunctional, and/or photoreactive cross linking agents may be used to bind biomolecules to tubular nanostructures. Examples of homobifunctional cross linkers include, but are not limited to, primary amine/primary amine linkers. Examples of heterofunctional cross linkers include, but are not limited to, primary amine/sulfhydryl linkers.

The one or more tubular nanostructures may be further functionalized with ligands as therapeutic agents, including but not limited to, anti-cancer therapeutic agents, antimicrobial therapeutic agents. The one or more tubular nanostructures may be further functionalized with markers to identify a cell target, e.g., a fluorescent marker, a radioactive marker, a quantum dot, a contrast agent for magnetic resonance imaging (MRI) marker, a ligand reaction activated marker, lipid membrane reactive marker, cell environment reactive marker, or combinations thereof.

A composite tubular nanostructure may comprise two or more tubular nanostructures each including a hydrophobic surface region, each hydrophobic region flanked by two hydrophilic surface regions configured to form a pore in a lipid bilayer membrane. For example, the composite tubular nanostructure can include 3 tubular nanostructures or 7 tubular nanostructures. Composite tubular nanostructures may be used to create multiple pores at one or more sites in the targeted lipid bilayer. Tubular nanostructures or composite tubular nanostructures may be modified to facilitate one or more elements to control transport of molecules through the tubular nanostructure. In one aspect, the one or more elements includes at least one second ligand configured to reversibly bind a cognate of interest, wherein the cognate of interest passes through the pore. In another aspect, the one or more elements can reversibly block the pore. Tubular nanostructures or composite tubular nanostructures may be further modified to facilitate active transport, facilitated transport, or passive transport of biomolecules through the pores formed by the nanotubes in the lipid bilayer. Active transport requires an external energy source, e.g., the hydrolysis of ATP to transport biomolecules such as ions against a concentration gradient, the biomolecules moving, for example, from low to high concentration.

The tubular nanostructures may be modified in such a manner as to allow transit of the nanotubes through the plasma membrane with subsequent targeting and insertion into the lipid bilayer of one or more internal organelles, e.g., mitochondria. Once targeted to the lipid bilayer of the organelle membrane, the tubular nanostructure may form pores that enable active transport, facilitated transport, or passive transport of contents into or out of the organelle. In certain organelles, disruption of the lipid bilayer may lead to cell death. In one example, tubular nanostructures may be selectively directed to the outer membrane of mitochondria in target cells where they insert into and disrupt the outer mitochondrial membrane leading to target cell death. The tubular nanostructures having hydrophobic surface region flanked by two hydrophilic surface regions for insertion and retention in a lipid bilayer may be modified in such a manner as to mask the hydrophilic ends and allow transit through the plasma membrane. In one embodiment, the hydrophilic ends of the tubular nanostructure are modified with a hydrophobic moiety through a chemical bond that may be cleaved once the nanotube has passed into the cell.

Figure 3:
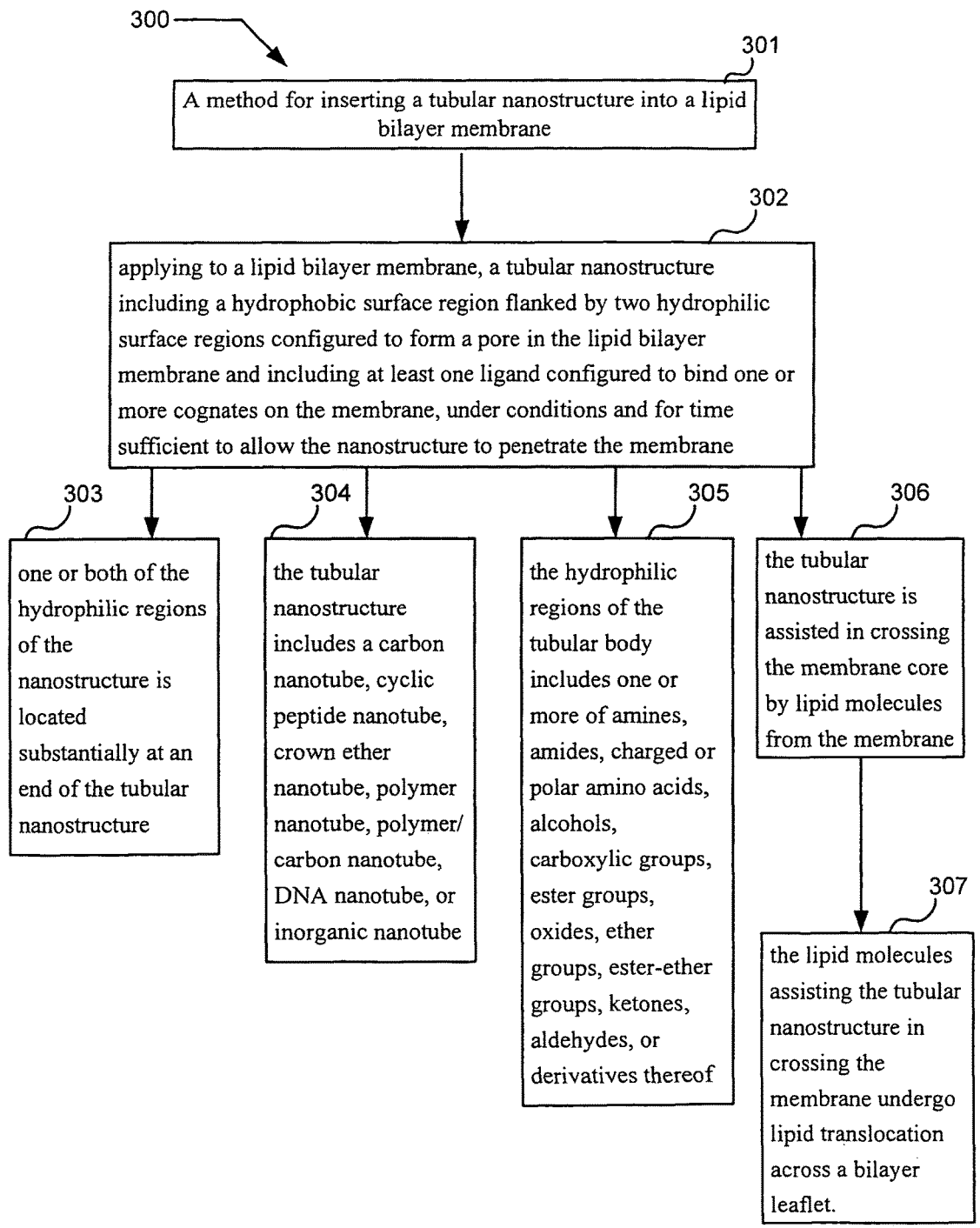
FIG. 3 depicts a logic flowchart of a method for inserting a tubular nanostructure into a lipid bilayer membrane.

With reference to the figures, and with reference now to FIGS. 1, 2, and 3, depicted is one aspect of a system that may serve as an illustrative environment of and/or for subject matter technologies, for example, a tubular nanostructure which comprises a hydrophobic surface region flanked by two hydrophilic surface regions configured to form a pore in a lipid bilayer membrane, and at least one ligand configured to bind one or more cognates on the membrane, or for example, a tubular nanostructure which comprises a surface region configured to pass through a lipid bilayer membrane of a cell, and a hydrophobic surface region flanked by two hydrophilic surface regions configured to form a pore in a lipid bilayer membrane of a cellular organelle. Accordingly, the present application first describes certain specific exemplary methods of FIGS. 1, 2, and 3; thereafter, the present application illustrates certain specific exemplary methods. Those having skill in the art will appreciate that the specific methods described herein are intended as merely illustrative of their more general counterparts.

Continuing to refer to FIG. 1, depicted is a partial diagrammatic view of an illustrative embodiment of a tubular nanostructure or a composite tubular nanostructure and a method for inserting a tubular nanostructure or a composite tubular nanostructure into a lipid bilayer membrane. In FIG. 1A, a tubular nanostructure 100 includes a hydrophobic surface region 110 flanked by two hydrophilic surface regions 120 is configured to form a pore 170 in a lipid bilayer membrane 150, 160. The tubular nanostructure 100 further includes at least one ligand 130 configured to bind one or more cognates 140 on the lipid bilayer membrane 150, 160. In FIG. 1B, the tubular nanostructure 100 includes the at least one ligand 130 configured to bind to the one or more cognates 140 on the membrane 150, 160. The one or more cognates 140 may be in various positions relative to the extracellular side 160 of the membrane and the intracellular side 150 of the membrane. In FIG. 1C, the tubular nanostructure 100 including the hydrophobic surface region 110 flanked by two hydrophilic surface regions 120 is integrated into the lipid bilayer membrane 150, 160 of the cell. The tubular nanostructure is configured to form a pore 170 in the lipid bilayer membrane 150, 160. In FIG. 1D, the tubular nanostructure 100 includes the at least one ligand 130 configured to bind to the one or more cognates 140 on the membrane 150, 160. In this aspect, the at least one ligand 130 is configured to bind to the one or more cognates 140 on the intracellular side 150 of the membrane. The tubular nanostructure is configured to form a pore 170 in the lipid bilayer membrane 150, 160 of the cell.

Continuing to refer to FIG. 2, depicted is a partial diagrammatic view of an illustrative embodiment of a tubular nanostructure or a composite tubular nanostructure and a method for inserting a tubular nanostructure or a composite tubular nanostructure into a lipid bilayer membrane of a cellular organelle. In FIGS. 2A and 2B, a tubular nanostructure 200 which comprises a surface region 210 is configured to pass through a lipid bilayer membrane 250, 260 of a cell. The lipid bilayer membrane of the cell has an extracellular side 260 of the membrane and an intracellular side 250 of the membrane In FIG. 2C, the tubular nanostructure further includes a hydrophobic surface region 220 flanked by two hydrophilic surface regions 225 configured to form a pore 290 in a lipid bilayer membrane 270, 280 of a cellular organelle. The tubular nanostructure 200 which comprises a surface region 210 is configured to pass through a lipid bilayer membrane 250, 260 of the cell. The tubular nanostructure 200 is configured to interact with a cellular component 285 to produce the at least one tubular nanostructure including the hydrophobic surface region 220 flanked by two hydrophilic surface regions 225. The tubular nanostructure 200 may further include at least one ligand 230 configured to bind one or more cognates 240 on the lipid bilayer membrane 270, 280 of the cellular organelle. The one or more cognates 240 may be in various positions relative to the cytoplasmic side 280 of the lipid bilayer membrane or the intraorganellar side 270 of the lipid bilayer membrane of the cellular organelle. In FIG. 2D, the tubular nanostructure 200 including the hydrophobic surface region 220 flanked by two hydrophilic surface regions 225 is integrated into the lipid bilayer membrane 270, 280 of the cellular organelle. The tubular nanostructure is configured to form a pore 290 in the lipid bilayer membrane 270, 280. The tubular nanostructure 200 may include the at least one ligand 230 configured to bind to the one or more cognates 240 on the membrane 280 of a cellular organelle. In FIG. 2E, at least one ligand 230 is configured to bind to the one or more cognates 240 on the intraorganellar side 270 of the membrane. The tubular nanostructure is configured to form a pore 290 in the lipid bilayer membrane 280 of the cellular organelle.

Figure 4:
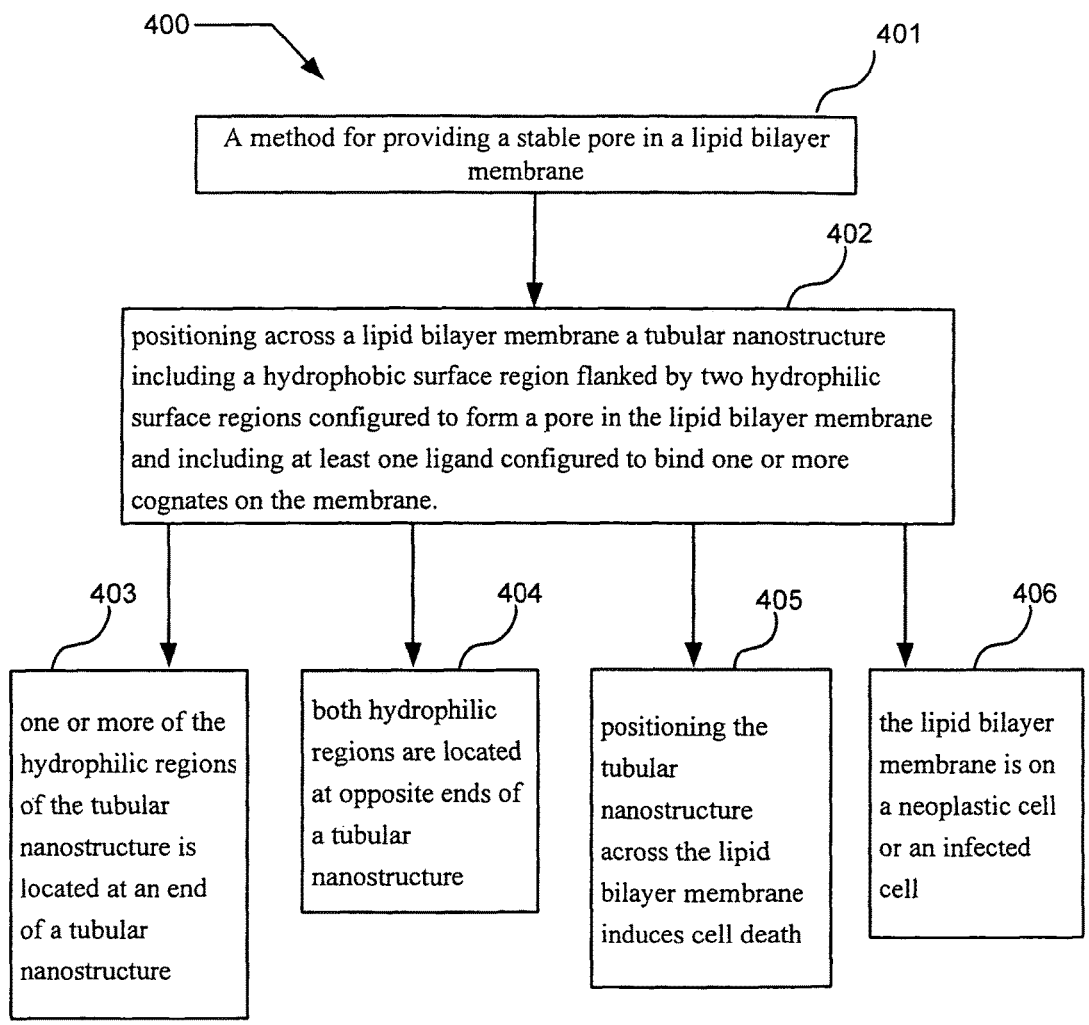
FIG. 4 depicts a logic flowchart of a method for providing a stable pore in a lipid bilayer membrane.

FIG. 3 depicts some exemplary aspects of a method as that described in FIGS. 1 and 2. FIG. 3 illustrates an exemplary method 300 for inserting a tubular nanostructure into a lipid bilayer membrane. The method includes applying 302 to a lipid bilayer membrane, a tubular nanostructure including a hydrophobic surface region flanked by two hydrophilic surface regions configured to form a pore in the lipid bilayer membrane and including at least one ligand configured to bind one or more cognates on the membrane, under conditions and for time sufficient to allow the nanostructure to penetrate the membrane FIG. 4 illustrates an exemplary method 400 for providing a stable pore in a lipid bilayer membrane. The method includes positioning 402 across a lipid bilayer membrane a tubular nanostructure including a hydrophobic surface region flanked by two hydrophilic surface regions configured to form a pore in the lipid bilayer membrane and including at least one ligand configured to bind one or more cognates on the membrane.

Figure 5:
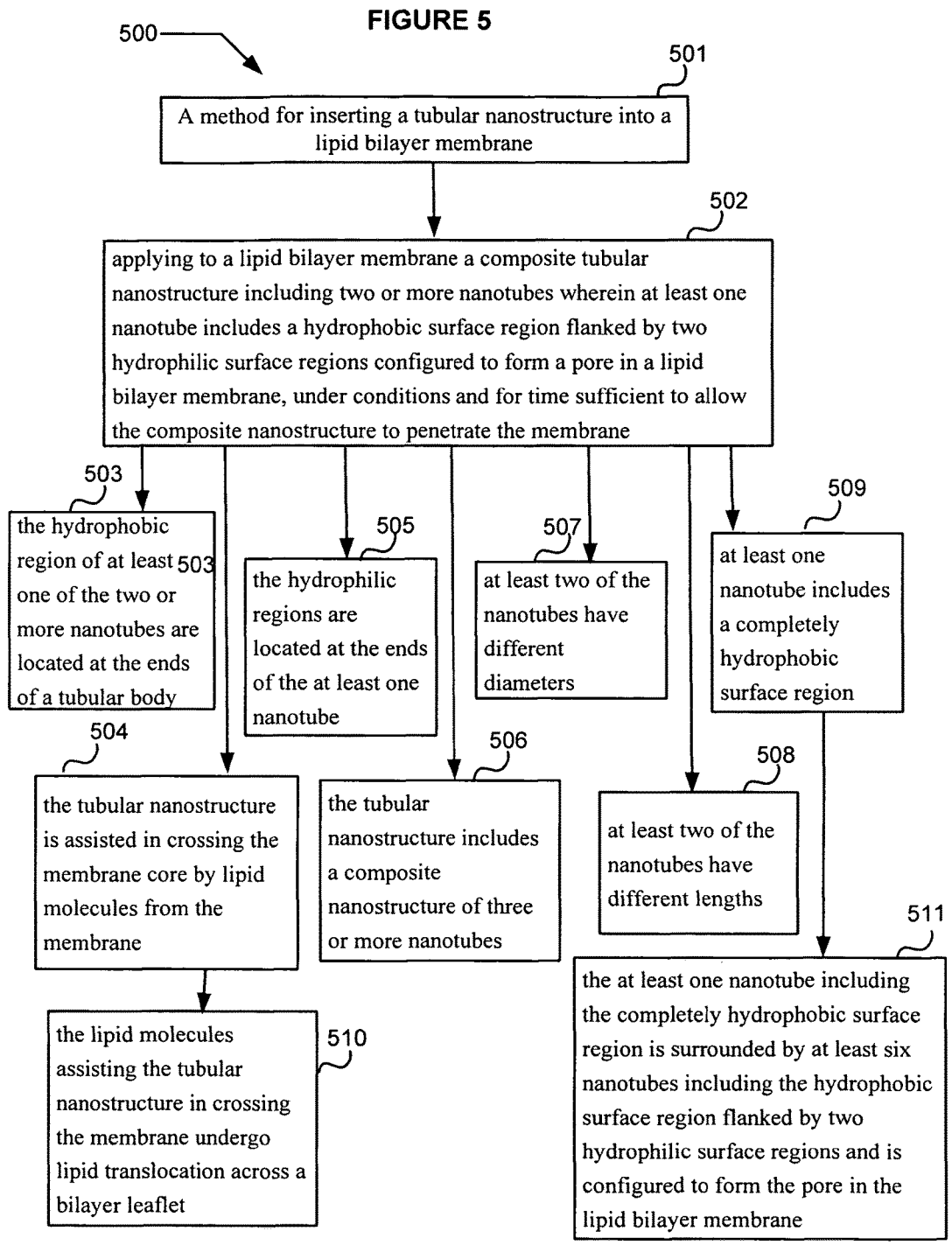
FIG. 5 depicts a logic flowchart of a method for inserting a tubular nanostructure into a lipid bilayer membrane.

FIG. 5 illustrates an exemplary method 500 for inserting a tubular nanostructure into a lipid bilayer membrane. The method includes applying 502 to a lipid bilayer membrane a composite tubular nanostructure including two or more nanotubes wherein at least one nanotube includes a hydrophobic surface region flanked by two hydrophilic surface regions configured to form a pore in a lipid bilayer membrane, under conditions and for time sufficient to allow the composite nanostructure to penetrate the membrane.

Figure 6:
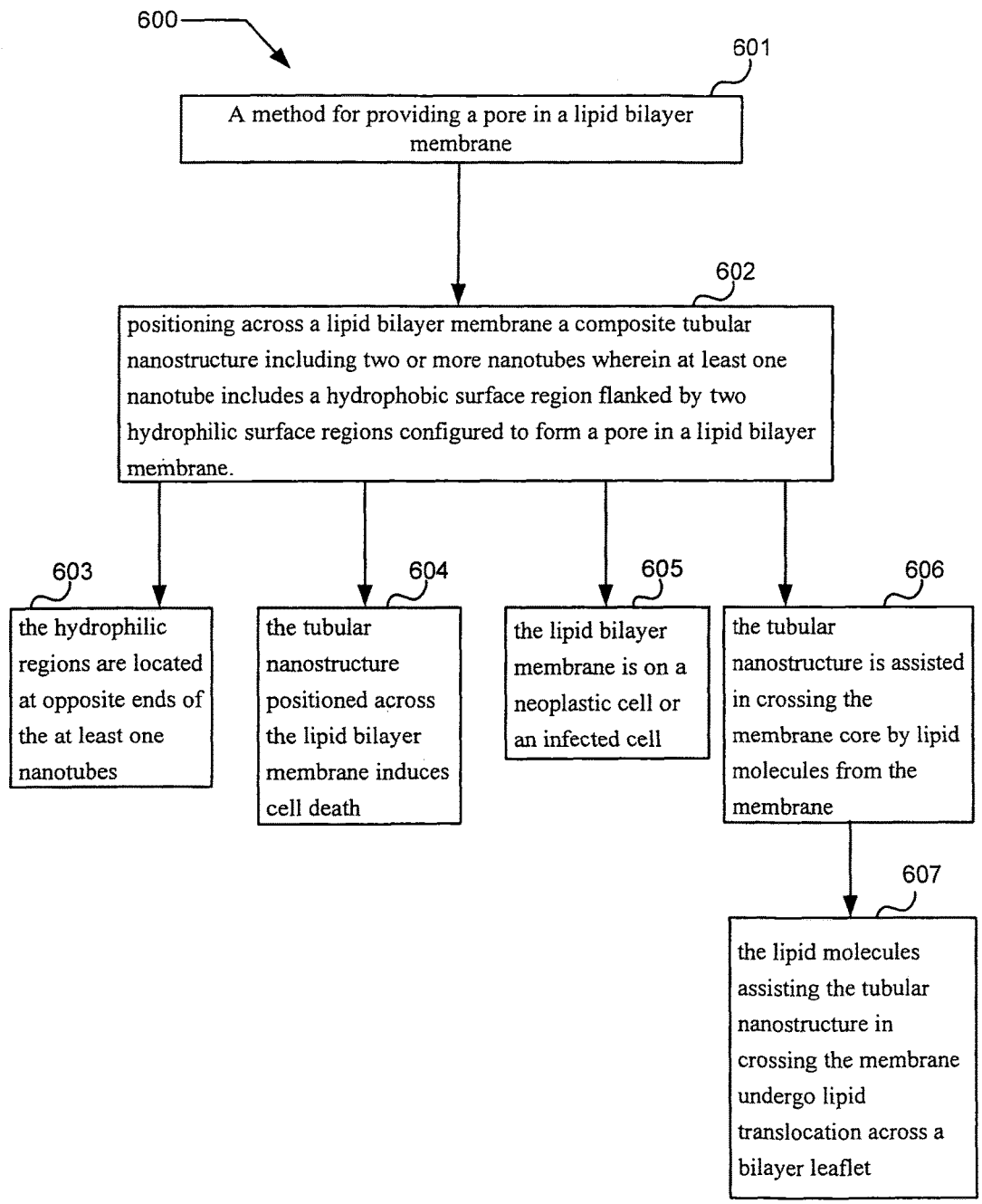
FIG. 6 depicts a logic flowchart of a method for providing a pore in a lipid bilayer membrane.

FIG. 6 illustrates an exemplary method 600 for providing a pore in a lipid bilayer membrane. The method includes positioning 602 across a lipid bilayer membrane a composite tubular nanostructure including two or more nanotubes wherein at least one nanotube includes a hydrophobic surface region flanked by two hydrophilic surface regions configured to form a pore in a lipid bilayer membrane.

Figure 7:
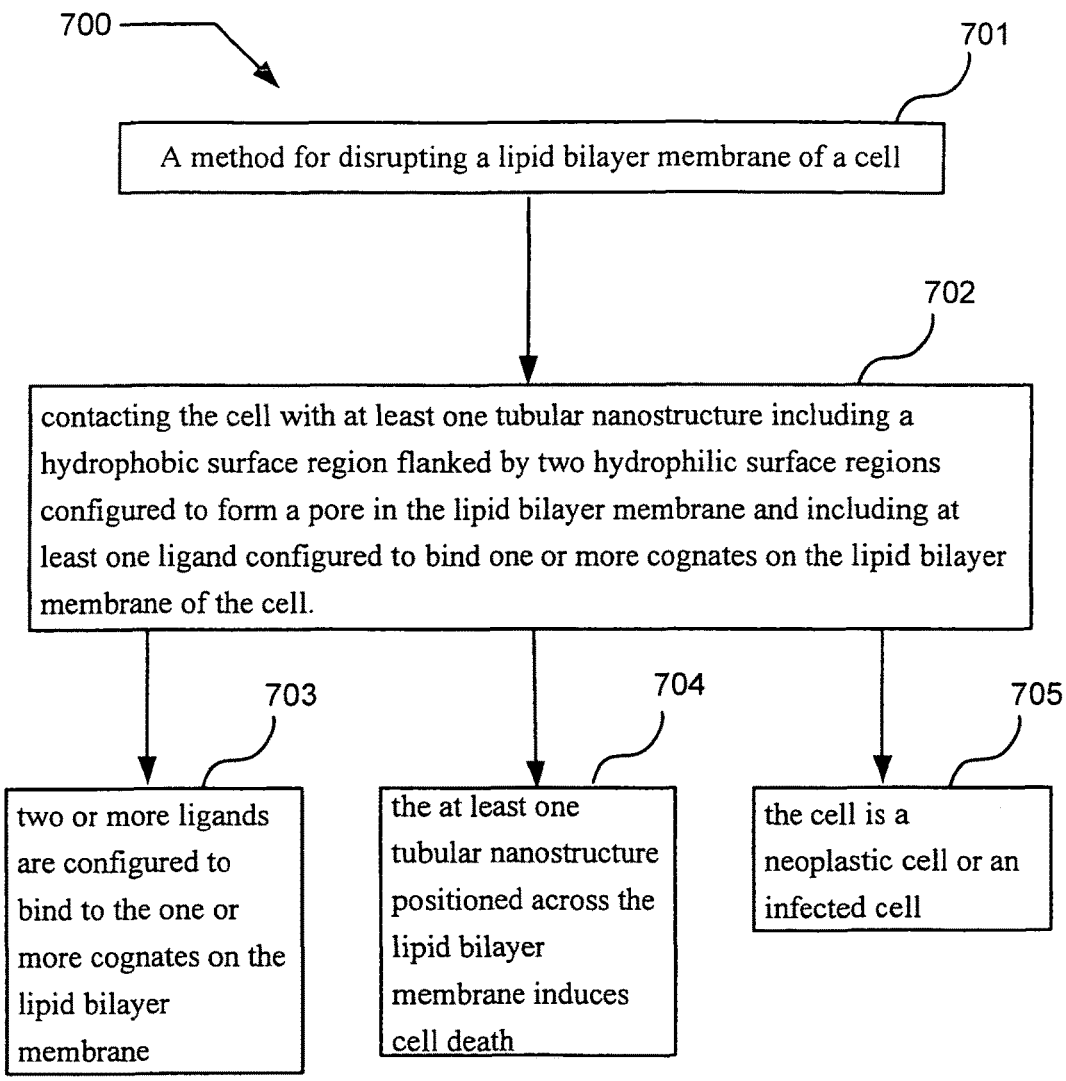
FIG. 7 depicts a logic flowchart of a method for disrupting a lipid bilayer membrane of a cell.

FIG. 7 illustrates an exemplary method 700 for disrupting a lipid bilayer membrane of a cell. The method includes contacting 702 the cell with at least one tubular nanostructure including a hydrophobic surface region flanked by two hydrophilic surface regions configured to form a pore in the lipid bilayer membrane and including at least one ligand configured to bind one or more cognates on the lipid bilayer membrane of the cell.

Tubular Nanostructure

Tubular nanostructures as described herein may be made from a wide variety of materials, for example, organic, inorganic, polymeric, biodegradable, biocompatible and combinations thereof. Non-limiting examples of inorganic materials to make tubular nanostructures as described herein include iron oxide, silicon oxide, titanium oxide and the like. Examples of biodegradable monomers formed into tubular nanostructures include polysaccharides, cellulose, chitosan, carboxymethylated cellulose, polyamino-acids, polylactides and polyglycolides and their copolymers, copolymers of lactides and lactones, polypeptides, poly-(ortho)esters, poly-dioxanone, poly-β-aminoketones, polyphosphazenes, polyanhydrides, polyalkyl(cyano)acrylates, poly(trimethylene carbonate) and copolymers, poly(ϵ-caprolactone) homopolymers and copolymers, polyhydroxybutyrate and polyhydroxyvalerate, poly(ester)urethanes and copolymers, polymethyl-methacrylate and combinations thereof. The carrier may even include or made from polyglutamic or polyaspartic acid derivatives and their copolymers with other amino-acids.

The tubular nanostructure as described herein may be a carbon nanotube. Carbon nanotubes are all-carbon hollow graphitic tubes with nanoscale diameter. They can be classified by structure into two main types: single walled CNTs (SWNTs), which consist of a single layer of graphene sheet seamlessly rolled into a cylindrical tube, and multiwalled CNTs (MWNTs), which consist of multiple layers of concentric cylinders. Carbon sources for use in generating carbon nanotubes include, but are not limited to, carbon monoxide and hydrocarbons, including aromatic hydrocarbons, e.g., benzene, toluene, xylene, cumene, ethylbenzene, naphthalene, phenanthrene, anthracene or mixtures thereof, non-aromic hydrocarbons, e.g., methane, ethane, propane, ethylene, propylene, acetylene or mixtures thereof; and oxygen-containing hydrocarbons, e.g., formaldehyde, acetaldehyde, acetone, methanol, ethanol or mixtures thereof.

Carbon nanotubes may be synthesized from one or more carbon sources using a variety of methods, e.g., arc-discharge, laser ablation, or chemical vapor deposition (CVD; see, e.g., Bianco, et al., in *Nanomaterials for Medical Diagnosis and Therapy*. pp. 85-142. Nanotechnologies for the Live Sciences Vol. 10 Edited by Challa S. S. R. Kumar, WILEY-VCH Verlag GmbH & Co. KGaA, Weinheim, 2007, which is incorporated herein by reference).

Carbon nanotubes may be synthesized using the arc discharge method which creates nanotubes through arc-vaporization of two carbon rods placed end to end, separated by approximately 1 mm, in an enclosure that is filled, for example, with inert gas (e.g., helium, argon) at low pressure (between 50 and 700 mbar). A direct current of 50 to 100 amperes driven by approximately 20 volts creates a high temperature discharge between the two electrodes. The discharge vaporizes one of the carbon rods and forms a small rod shaped deposit on the other rod.

Alternatively, carbon nanotubes may be synthesized using laser ablation in which a pulsed or continuous laser energy source is used to vaporize a graphite target in an oven at 1200° C. The oven is filled with an inert gas such as helium or argon, for example, in order to keep the pressure at 500 Torr. A hot vapor plume forms, expands, and cools rapidly. As the vaporized species cool, small carbon molecules and atoms quickly condense to form larger clusters. The catalysts also begin to condense and attach to carbon clusters from which the tubular molecules grow into single-wall carbon nanotubes. The single-walled carbon nanotubes formed in this case are bundled together by van der Waals forces.

Carbon nanotubes may also be synthesized using chemical vapor deposition (CVD). CVD synthesis is achieved by applying energy to a gas phase carbon source such as methane or carbon monoxide, for example. The energy source is used to "crack" the gas molecules into reactive atomic carbon. The atomic carbon diffuses towards a substrate, which is heated and coated with a catalyst, e.g., Ni, Fe or Co where it will bind. The catalyst is generally prepared by sputtering one or more transition metals onto a substrate and then using either chemical etching or thermal annealing to induce catalyst particle nucleation. Thermal annealing results in cluster formation on the substrate, from which the nanotubes will grow. Ammonia may be used as the etchant. The temperatures for the synthesis of nanotubes by CVD are generally within the 650-900° C. range. A number of different CVD techniques for synthesis of carbon nanotubes have been developed, such as plasma enhanced CVD, thermal chemical CVD, alcohol catalytic CVD, vapor phase growth, aero gel-supported CVD and laser-assisted thermal CVD, and high pressure CO disproportionation process (HiPCO). Additional methods describing the synthesis of carbon nanotubes may be found, for example, in U.S. Pat. Nos. 5,227,038; 5,482,601; 6,692,717; 7,354,881 which are incorporated herein by reference.

Carbon nanotubes may be synthesized as closed at one or both ends. As such, forming a hollow tube may necessitate cutting the carbon nanotubes. Carbon nanotubes may be cut into smaller fragments using a variety of methods including but not limited to irradiation with high mass ions, intentional introduction of defects into the carbon nanotube during synthesis, sonication in the presence of liquid or molten hydrocarbon, lithography, oxidative etching with strong oxidating agents, mechanical grinding with diamond balls, or physical cutting with an ultra microtome (see, e.g., U.S. Pat. No. 7,008,604; Wang et al, *Nanotechnol.* 18:055301, 2007, which are incorporated herein by reference). For irradiation with high mass ions, for example, the carbon nanotubes are subjected to a fast ion beam, e.g., from a cyclotron, at energies of from about 0.1 to 10 giga-electron volts. Suitable high mass ions include those over about 150 AMU's such as bismuth, gold, uranium and the like. To generate defects that are susceptible to cleavage, the carbon nanotubes may be synthesized in the presence of a small amount of boron, for example. For sonication, carbon nanotubes may be sonicated in the presence of 1,2-dichloroethane, for example, using a sonicator with sufficient acoustic energy over a period ranging from 10 minutes to 24 hours, for example. For oxidative etching, carbon nanotubes may be incubated in a solution containing 3:1 concentrated sulfuric acid:nitric acid for 1 to 2 days at 70° C. For cutting with an ultra microtome, the carbon nanotubes are magnetically aligned, frozen to a temperature of about −60° C., and cut using an ultra-thin cryo-diamond knife.

Once synthesized, carbon nanotubes may be further purified to eliminate contaminating impurities, e.g., amorphous carbon and catalyst particles. Methods for further purification include, but are not limited to, acid oxidation, microfiltration, chromatographic procedures, microwave irradiation, and polymer-assisted purification (see, e.g., U.S. Pat. No. 7,357,906, which is incorporated herein by reference). Chromatography and microfiltration may also be used to isolate a uniformed population of carbon nanotubes with similar size and diameter, for example (see, e.g., Bianco, et al., in *Nanomaterials for Medical Diagnosis and Therapy.* pp. 85-142. Nanotechnologies for the Live Sciences Vol. 10 Edited by Challa S. S. R. Kumar, WILEY-VCH Verlag GmbH & Co. KGaA, Weinheim, 2007, which is incorporated herein by reference). Alternatively, purified carbon nanotubes may be purchased from a commercial source (from, e.g., Carbon Nanotechologies, Houston, Tex.; Sigma-Aldrich, St. Louis, Mo.).

Alternatively, a tubular nanostructure as described herein may be a peptide nanotube. Peptide nanotubes are extended tubular beta-sheet-like structures and are constructed by the self-assembly of flat, ring-shaped peptide subunits made up of alternating D- and L-amino acid residues as described in U.S. Pat. Nos. 6,613,875 and 7,288,623, and in Hartgerink, et al., *J. Am. Chem. Soc.* 118:43-50, 1996, which are incorporated herein by reference. For example, gramicidin is a pentadecapeptide which forms a β-helix with a hydrophilic interior and a lipophilic exterior bearing amino acid side chains in membranes and nonpolar solvents. In this instance, the helix length is approximately half of the thickness of a lipid bilayer and as such, two gramicidin molecules form an end-to-end dimer stabilized by hydrogen bonds that spans the lipid bilayer. Peptide nanotubes are constructed by highly convergent noncovalent processes by which cyclic peptides rapidly self-assemble and organize into ultra large, well ordered three-dimensional structures, upon an appropriate chemical- or medium-induced triggering. The properties of the outer surface and the internal diameter of peptide nanotubes may be adjusted by the choice of the amino acid side chain functionalities and the ring size of the peptide subunit employed.

Alternatively, a tubular nanostructure as described herein may be a lipid nanotube. Lipid nanotubes are typically formed using self-assembling microtubule-forming diacetylenic lipids, such as complex chiral phosphatidylcholines, and mixtures of these diacetylenic lipids as described in U.S. Pat. Nos. 4,877,501, 4,911,981 and 4,990,291, which are incorporated herein by reference. The synthesis of self-assembling lipid nanotubes may be accomplished by combining the appropriate lipids with an alcohol and a water phase which leads to the production of lipid microcylinders by direct crystallization. The formation of the lipid tubules may be modulated by the choice of alcohol and/or combination of alcohols, the ratio of alcohol to water, and variations in the reaction temperature (see, e.g., U.S. Pat. No. 6,013,206, which is incorporated herein by reference). A simple method for generating uniform lipid nanotubes from single-chain diacetylene secondary amine salts has been described in Lee, et al., *J. Am. Chem. Soc.* 126:13400-13405, 2004, which is incorporated herein by reference.

Functionalization of Tubular Nanostuctures for Targeting and Insertion into a Cellular Membrane Tubular nanostructures as described herein may be functionalized to include hydrophilic surface regions at one or both ends of the tubular nanostructure to facilitate insertion and retention of the tubular nanostructure into a lipid bilayer membrane associated with a target cell or organelle (see, e.g., U.S. Patent Application 2004/0023372 A1, which is incorporated herein by reference). The hydrophilic surface region may include one or more of amines, amides, charged or polar amino acids, alcohols, carboxylic groups, oxides, ester groups, ether groups, or ester-ether groups, ketones, aldehydes, or derivatives thereof. Tubular nanostructures may be further functionalized to include one or more ligand, one or more therapeutic compounds, one or more toxins, one or more markers, or combinations thereof. A tubular nanostructure may be functionalized using non-covalent and covalent methodologies.

Non-covalent functionalization of carbon nanotubes, for example, may be accomplished using π-π stacking interactions between conjugated molecules and the graphitic sidewall of the tubular nanostructure. For example, compounds with a pyrene moiety, e.g., N-succinimidyl-1-pyrenebutanoate may be irreversibly absorbed onto the surface of a carbon nanotube through π-π stacking interaction. In this instance, the succinimidyl ester group associated with the pyrenebutonaote may be used to link to primary or secondary amines and as such may be used to couple biomolecules, e.g., proteins and nucleic acids to the tubular nanostructure. Other molecules that may be linked to a tubular nanostructure via π-π stacking interactions include the photosensitizers phthalocyanines and porphyrins (see, e.g., Bianco, et al., in *Nanomaterials for Medical Diagnosis and Therapy*. pp. 85-142. Nanotechnologies for the Live Sciences Vol. 10 Edited by Challa S. S. R. Kumar, WILEY-VCH Verlag GmbH & Co. KGaA, Weinheim, 2007, which is incorporated herein by reference).

Alternatively, non-covalent functionalization may be accomplished using hydrophobic interactions with amphiphilic molecules. In this instance, the hydrophobic surface of the amphiphilic molecules interact noncovalently with the aromatic surface of the carbon nanotube while exposing their hydrophilic parts to the aqueous medium, allowing for solubilization of hydrophobic tubular nanostructures in aqueous solutions. Examples of molecules that may be used for this purpose include, but are not limited to, water-soluble polymers, e.g., polyvinylpyrrolidone and polystyrenesulfonate; surfactants, e.g., anionic, nonionic, and cationic surfactants including, for example, deoxycholic acid, taurodeoxycholic acid, sodium dodecylbenzene sulfonate, and sodium dodecyl sulfate; amphiphilic peptides, and single stranded DNA. In addition, a biomolecule may be attached indirectly to a tubular nanotube, e.g., a carbon nanotube through an amphiphilic bifunctional linker, e.g., phospholipid (PL)-poly(ethylene glycol) (PEG) chains and terminal amine (PL-PEG-NH$_2$) in which the PL alkyl chains interact noncovalently with the carbon nanotube and the amine group may be used to link to biomolecules. Other examples of functionalized PEG lipids include, but are not limited to, phospholipid-PEG-carboxylic acid, phospholipid-PEG-maleimide, and phospholipid-PEG-biotin, for example. For example, the phospholipid-PEG-biotin derivative 1,2-distearoyl-sn-glycero-3-phosphoethanolamine-N-[biotinyl (polyethylene glycol] 2000] (DSPE-PEG(2000)-biotin) may be added to carbon nanotubes by sonication, followed by centrifugation to isolate the functionalized nanotubes (see, e.g., Chakravarty, et al., *Proc. Natl. Acad. Sci. USA* 105: 8697-8702, 2008, which is incorporated herein by reference). Similarly, DNA or RNA may be linked to a carbon nanotube using a heterofunctional crosslinker, e.g., sulfosuccinimidyl 6-(3'-[2-pyridyldithio]propionamido)hexanoate (sulfo-LC-SPDP). (see, e.g., Bianco, et al., in *Nanomaterials for Medical Diagnosis and Therapy*. pp. 85-142. Nanotechnologies for the Live Sciences Vol. 10 Edited by Challa S. S. R. Kumar, WILEY-VCH Verlag GmbH & Co. KGaA, Weinheim, 2007, which is incorporated herein by reference).

Tubular nanostructures may also be functionalized using covalent interactions. Covalent functionalization of carbon nanotubes, for example, may involve defect functionalization and/or side-wall functionalization. Defect functionalization takes advantage of defects in the carbon nanotube structure characterized by disruptions in the six-membered rings of the graphene sheets such as might be found at the cut ends of carbon nanotubes. Defect functionalization may also be present on the side-walls, characterized by the presence of five- and seven-membered rings within the graphene sheet of six-membered rings. Treatment of carbon nanotubes with strong oxidizing agents, e.g., nitric acid, $KMnO_4/H_2SO_4$, $O_2$, $K_2Cr_2O_7/H_2SO_4$ or $OsO_4$ may be used to cut carbon nanotubes, generating open ends and creating a hollow tube (see, e.g., U.S. Pat. No. 7,008,604, which is incorporated herein by reference). Oxidation may also be used to add functional groups, e.g., carboxylic acid, ketone, alcohol and ester groups to the ends and defect sites on the side-walls and as such may be used to create hydrophilic surface regions.

The functional groups added to carbon nanotubes by oxidation, for example, may be used to further modify the ends and/or the side walls of the nanotubes. For example, carboxylic acid moieties on the nanotube may be used to formamide and ester linkages. In this instance, reactive intermediates are formed by treating the carboxylic acid groups with thionyl chloride, carbodiimide, or N-hydroxysuccinimide (NHS). The reactive intermediates are then able to form covalent linkages with biomolecules, e.g., polymers such poly-propionyl-ethylenimine-co-ethylenimine (PPEI-EI), poly-n-vinylcarbazole (PVK-PS) and polyethylene glycol (PEG), poly-n-butyl methacrylate (PnBMA), polymethyl methacrylate (PMMA), and PMMA-b-polyhydroxyethyl methacrylate (PHEMA); proteins such as bovine serum albumin; DNA molecules; and other biomolecules, e.g., biotin.

End and/or side-wall functionalization of a tubular nanostructure may be accomplished using various chemical reactions including but not limited to fluorination, radical addition, nucleophilic addition, electrophilic addition, and cycloaddition, for example (see, e.g., Bianco, et al., in *Nanomaterials for Medical Diagnosis and Therapy*. pp. 85-142. Nanotechnologies for the Live Sciences Vol. 10 Edited by Challa S. S. R. Kumar, WILEY-VCH Verlag GmbH & Co. KGaA, Weinheim, 2007, which is incorporated herein by reference). Fluorine may be added to the surface of a carbon nanotube, for example, by heating the nanotube in the presence of elemental fluorine at temperatures ranging from 150 to 600° C. (see, e.g., U.S. Pat. No. 6,841,139, which is incorporated herein by reference). The fluorine group on the carbon nanotube may be further substituted with strong nucleophilic reagents, e.g., Grignard, alkyllithium reagents and/or metal alkoxides. Alternatively, a tubular nanostructure, e.g., a carbon nanotube, may be functionalized by cycloaddition with, for example, dichlorocarbene, nitrenes, bromomalonates, o-quinodimethane, azido group, alkyne/azide, and/or azomethine ylides. For example, protected amino groups may be introduced onto the surface of carbon nanotubes using 1,3-dipolar cycloaddition of azomethine ylides. The N-protected amino acid may then be used to link biomolecules, e.g., bioactive peptides (see, e.g., Pantorotto, et al., *J. Am. Chem. Soc.* 125:6160-6164, 2003, which is incorporated herein by reference).

In some instances, it may be beneficial to selectively functionalize one portion or portions of the ends and/or sidewalls of a tubular nanostructure. Asymmetric functionalization of carbon nanotubes may be accomplished using a masking technique. For example, carbon nanotubes may be partially embedded in a polymer matrix, including, but not limited to, poly(dimethylsiloxane), polystyrene, poly (methyl methacrylate), or polydiene rubber or a combination thereof and the non-embedded or exposed portion functionalized (see, e.g., Qu & Dai, *Chem. Commun.* 37: 3829-3861, 2007, which is incorporated herein by reference). An organic solvent, e.g., toluene, may be used to wash away the masking polymer. Asymmetric functionalization of the ends of carbon nanotubes may be accomplished using a lithographic procedure to cut the nanotubes followed by chemical modification of the exposed tube ends via plasma treatment while the tube side-walls remain protected by a resist layer (see, e.g., Burghard *Small* 1:1148-1140, 2005, which is incorporated herein by reference).

Alternatively, asymmetric functionalization of carbon nanotubes may be accomplished by floating the nanotubes on a photoreactive solution with only one side of the nanotube in contact with the solution and exposing the solution to UV light (see, e.g., U.S. Patent Application 2006/0257556 A1, which is incorporated herein by reference). Photoreactive reagents are chemically inert reagents that become reactive when exposed to ultraviolet or visible light and are exemplified by derivatives of aryl azides. When an aryl azide is exposed to UV light, it forms a nitrene group that can initiate addition reactions with double bonds, insertion into C—H and N—H sites, or subsequent ring expansion to react with a nucleophile (e.g., primary amines). Examples of photoreactive cross linkers include, but are not limited, to primary amine linkers such as ANB-NOS(N-5-azido-2-nitrobenzyloxysuccinimide), NHS-ASA (N-hydroxy-succinimideyl-4-azidosalicyclic acid), Sulfo HSAB (N-hydroxysulfosuccinimidyl-4-azidobenzoate), Sulfo SAED (sulfosuccinimidyl 2-(7-azido-4-methylcoumarin-3-acetamide)ethyl-1,3-dithiopropionate), Sulfo SAND (sulfosuccinimidyl 2-(m-azido-o-nitrobenzamido)-ethyl-1,3'-propionate), Sulfo SANPAH (sulfosuccinimidyl 6-(4'-azido-2'-nitrophenylamino) hexanoate), Sulfo SADP (sulfosuccinimidyl (4-azidophenyldithio) propionate, and Sulfo SASD (sulfosuccinimidyl-2-(rho-azidosalicylamido) ethyl-1,3-dithiopropionate; carbohydrate linkers such as ABH (azidobenzoyl hydrazide); arginine linkers such as APG (azidophenyl glyoxal monohydrate), sulfhydryl linkers such as APDP (N-(4-[rho-azidosalicylamido] butyl)-3'-(2'-pyridyldithio) propionamide); non selective linkers such as BASED (bis(beta-[4-azidosalicylamido]-ethyl) disulfide).

Tubular nanostructures may be functionalized to include one or more ligand, therapeutic compound, toxin, marker, or combinations thereof. In some instances the one or more ligand, therapeutic compound, toxin and/or marker is a protein biomolecule. Protein biomolecules that might be added to a tubular nanostructure include, but are not limited to, targeting biomolecules, e.g., antibodies, receptor ligands, and lectins; therapeutic biomolecules, e.g., therapeutic proteins or peptides; transporter biomolecules, e.g., components of the ATP-binding cassette (ABC) transporters; pore-forming agents such as antimicrobial peptides; and toxic biomolecules such as protein-based plant and bacterial toxins. The tubular nanostructure may be functionalized with amines, carboxylic acids, thiols, aldehydes and combinations thereof to facilitate linkage to protein biomolecules. For example, attachment of one or more protein molecules to a carbon nanotube may be performed using heterobifunctional crosslinkers. For example, a heterobifunctional crosslinker may be added covalently to a carbon nanotube by adding amino groups to the nanotube via azomethine ylide cycloaddition or alkyne azide cycloaddition, followed by derivatization of the amino groups with a heterobifunctional crosslinker, e.g., succiminidyl-4-(N-maleimidomethyl)cyclohexane-1-carboxy-(6-amidocaproate) (LC-SMCC). The nanotube functionalized in this manner is combined with a protein into which reactive sulfhydryl groups have been introduced with 2-iminothiolane-HCl (see, e.g., McDevitt, et al., *J. Nucl. Med.* 48:1180-1189, 2007, which is incorporated herein by reference). Alternatively, a protein biomolecule may be added to a tubular nanostructure such as a carbon nanotube, for example, by non-covalent attachment of phospholipid-PEG-NH$_2$ to the nanotube and covalent interaction of the associated amine group with thiolated protein (see, e.g., Welsher, et al., *Nano Lett.* 8:586-590, 2008, which is incorporated herein by reference). Alternatively, a protein biomolecule may be added to a tubular nanostructure using a biotin/avidin linkage in which the carbon nanotubes are functionalized with biotin using a phospholipid-PEG-biotin as described herein and combined with avidin- or streptavidin-modified protein. A protein may be modified with avidin, for example, by activating the avidin with m-maleimidobenzoyl-N-hydroxysuccinimide ester and linking it to thiolated target protein (see, e,g, Chakravarty, et al., *Proc. Natl. Acad. Sci. USA,* 105: 8697-8702, 2008, which is incorporated herein by reference).

Biomolecules such as antibodies, for example, may also be attached to peptide nanotubes and boron nitride nanotubes (see, e.g., Zhao & Matsui *Small* 3:1390-1393, 2007; U.S. Patent Application 2006/0067941, which are incorporated herein by reference). For example, boron nitride nanotubes may be chemically modified with primary amines such as methylamine and ethanolamine that may be used for additional functionalization of the nanotubes (Wu, et al., *J. Am. Chem. Soc.* 128:12001-12006, 2006, which is incorporated herein by reference).

One or more tubular nanostructures may be functionalized with one or more peptides. In some instances, one or more peptides may be linked to a tubular nanostructure using the methods described above for proteins. Alternatively, one or more peptides may be linked to a tubular nanostructure using fragment condensation of fully protected peptides and/or selective chemical ligation (see, e.g., U.S. Patent Application 20060199770; Pantarotto, et al., *J. Am. Chem. Soc.* 125:6160-6164, 2003, which are incorporated herein by reference). For selective chemical ligation, for example, carbon nanotubes may be functionalized with primary amines and N-succinimidyl 3-maleimidopropionate and reacted with N-terminal acetylated peptide to form peptide-carbon nanotube conjugates. Alternatively, peptides may be designed using phage display methodologies that selectively recognize and bind carbon nanotubes as described in U.S. Pat. No. 7,304,128, which is incorporated herein by reference.

In some instances, the one or more tubular nanostructures may be functionalized with one or more ligand, therapeutic compound, toxin, marker, or combination thereof that is a polynucleotide biomolecule. Polynucleotide biomolecules that might be added to a tubular nanostructure include, but are not limited to, aptamers, antisense RNA, RNAi, DNA, or combinations thereof. For example, DNA may be added to a tubular nanostructure such as a carbon nanotube using a streptavidin-biotin linkage. In this instance, streptavidin may be non-covalently associated with the carbon nanotube and combined with biotin modified DNA. Alternatively, single strand DNA may be bound to a carbon nanotube by direct non-covalent interaction forming a coil around the nanotube. Alternatively, a small oligonucleotide such as an aptamer, for example, may be linked to a carbon nanotube using carbodiimidazole (CDI)-Tween (see, e.g., So, et al., *J. Am. Chem. Soc.* 127:11906-11907, 2005, which is incorporated herein by reference). Alternatively, a DNA or RNA aptamer may be linked to a carbon nanotube via a streptavidin-biotin linkage. In this instance, biotin may be introduced into the DNA or RNA aptamer during synthesis of the aptamer and then bound to streptavidin associated with the carbon nanotube. Alternatively, a DNA or RNA aptamer may be conjugated to a tubular nanotube using amine- or sulfhydryl-reactive crosslinkers (e.g., from Pierce-Thermo Scientific, Rockford, Ill., USA) using the methods described herein. As such, the aptamer may be synthesized in the presence of specific bases modified with primary amines or thiols.

In some instances, the one or more tubular nanostructures may be functionalized with one or more ligand, therapeutic compound, toxin, marker, or combinations thereof as a small chemical compound. Small chemical compounds that might be added to a tubular nanostructure include, but are not limited to, targeting biomolecules, e.g., receptor binding ligands; therapeutic biomolecules, e.g., therapeutic small chemical compound drugs; toxins, e.g., chemotherapy agents; and markers, e.g., fluorescent dyes and/or radioactive compounds. For example, reversible attachment of a platinum based chemotherapy to a carbon nanotube can be used in which the platinum compound was modified with a linker arm and an N-succinimidyl ester group which readily formed amide linkages with PEG-tethered primary amines on the surface of carbon nanotubes (Feazell, et al., *J. Am. Chem. Soc.* 129:8438-8439, 2007, which is incorporated herein by reference).

In general, any of a number of homobifunctional, heterofunctional, and/or photoreactive cross linking agents may be used to bind biomolecules to tubular nanostructures. Examples of homobifunctional cross linkers include, but are not limited to, primary amine/primary amine linkers such as BSOCES ((bis(2-[succinimidooxy-carbonyloxy]ethyl) sulfone), DMS (dimethyl suberimidate), DMP (dimethyl pimelimidate), DMA (dimethyl adipimidate), DSS (disuccinimidyl suberate), DST (disuccinimidyl tartate), Sulfo DST (sulfodisuccinimidyl tartate), DSP (dithiobis(succinimidyl propionate), DTSSP (3,3'-dithiobis(succinimidyl propionate), EGS (ethylene glycol bis(succinimidyl succinate)) and sulfhydryl/sulfhydryl linkers such as DPDPB (1,4-di-(3'-[2' pyridyldithio]-propionamido) butane). Examples of heterofunctional cross linkers include, but are not limited to, primary amine/sulfhydryl linkers such as MBS (m-maleimidobenzoyl-N-hydroxysuccinimide ester), Sulfo MBS (m-maleimidobenzoyl-N-hydroxysuccinimide), GMBS (N-gamma-maleimidobutyryl-oxysuccinimide ester), Sulfo GMBS (N-gamma-maleimidobutyryloxysulfosuccinimide ester), EMCS(N-(epsilon-maleimidocaproyloxy) succinimide ester), Sulfo EMCS(N-(epsilon-maleimidocaproyloxy) sulfo succinimide), SIAB (N-succinimidyl (4-iodoacetyl)aminobenzoate), SMCC (succinimidyl 4-(N-maleimidomethyl) cyclohexane-1-carboxylate), SMPB (succinimidyl 4-(rho-maleimidophenyl) butyrate), Sulfo SIAB (N-sulfosuccinimidyl(4-iodoacetyl)aminobenzoate), Sulfo SMCC (sulfosuccinimidyl 4-(N-maleimidomethyl)cyclohexane-1-carboxylate), Sulfo SMPB (sulfosuccinimidyl 4-(rho-maleimidophenyl) butyrate), and MAL-PEG-NHS (maleimide PEG N-hydroxysuccinimide ester); sulfhydryl/hydroxyl linkers such as PMPI (N-rho-maleimidophenyl) isocyanate; sulfhydryl/carbohydrate linkers such as EMCH (N-(epsilon-maleimidocaproic acid) hydrazide); and amine/carboxyl linkers such as EDC (1-ethyl-3-(3-dimethylaminopropyl) carbodiimide hydrochloride).

Ligands Targeted to Cognates which are Associated with Target Cells and/or Organelles The tubular nanostructures as described herein may include one or more ligands that are configured to bind to one or more cognates associated with the lipid bilayer membrane of a target cell or organelle. A target cell may include a tumor cell and/or other diseased cell type in a mammalian subject. A target cell may also include a pathogen, e.g., bacteria, fungi, and/or parasites. In some instances, the tubular nanostructures may be designed to target a specific cellular organelle, e.g., the mitochondria. One or more cognates associated with a target cell or organelle may include at least one of a protein, a carbohydrate, a glycoprotein, a glycolipid, a sphingolipid, a glycerolipid, or metabolites thereof.

Tumor Markers

One or more tubular nanostructures may include one or more ligands that bind one or more cognates associated with a tumor cell. In this instance, the cognate may be a cell surface receptor or cell surface marker on a tumor cell. Examples of cognates associated with tumor cells may include, but are not limited to, BLyS receptor, carcinoembryonic antigen (CA-125), CD25, CD34, CD33 and CD123 (acute myeloid leukemia), CD20 (chronic lymphocytic leukemia), CD19 and CD22 (acute lymphoblastic leukemia), CD30, CD40, CD70, CD133, 57 kD cytokeratin, epithelial specific antigen, extracellular matrix glycoprotein tenascin, Fas/CD95, gastrin-releasing peptide-like receptors, hepatocyte specific antigen, human gastric mucin, human milk fat globule, lymphatic endothelial cell marker, matrix metalloproteinase 9, melan A, melanoma marker, mesothelin, mucin glycoproteins (e.g., MUC1, MUC2, MUC4, MUC5AC, MUC6), prostate specific antigen, prostatic acid phosphatase, PTEN, renal cell carcinoma marker, RGD-peptide binding integrins, sialyl Lewis A, six-transmembrane epithelial antigen of the prostate (STEAP), TNF receptor, TRAIL receptor, tyrosinase, villin. Other tumor associated antigens include, but are not limited to, alpha fetoprotein, apolipoprotein D, clusterin, chromogranin A, myeloperoxidase, MyoD1 myoglobin placental alkaline phosphatase c-fos, homeobox genes, aberrantly glycosylated antigens.

Bacterial Cognates

One or more tubular nanostructures may include one or more ligands that bind one or more cognates associated with bacteria. A cognate on bacteria may be a component of the bacterial outer membrane, cell wall, and/or cytoplasmic membrane, for example. Examples of cognates associated with the bacterial outer membrane of Gram-negative bacteria include, but are not limited to, lipopolysaccaride and OMP (outer membrane protein) porins, the latter of which are exemplified by OmpC, OmpF and PhoP of *E. coli*. Examples of cognates associated with the bacterial cell wall of both Gram-positive and Gram-negative bacterial include, but are not limited to, peptidoglycans polymers composed of an alternating sequence of N-acetylglucoamine and N-acetyl-muraminic acid and crosslinked by amino acids and amino acid derivatives. Examples of cognates associated with the bacterial cytoplasmic membrane include, but are not limited to, the MPA1-C (also called polysaccharide copolymerase, PCP2a) family of proteins, the MPA2 family of proteins, and the ABC bacteriocin exporter accessory protein (BEA) family of proteins. Other examples of cognates associated with bacteria include, but are not limited to, transporters, e.g., sugar porter (major facilitator superfamily), amino-acid/polyamine/organocation (APC) superfamily, cation diffusion facilitator, resistance-nodulation-division type transporter, SecDF, calcium:cation antiporter, inorganic phosphate transporter, monovalent cation:proton antiporter-1, monovalent cation:proton antiporter-2, potassium transporter, nucleobase:cation symporter-2, formate-nitrite transporter, divalent anion:sodium symporter, ammonium transporter, and multi-antimicrobial extrusion;

channels, e.g., major intrinsic protein, chloride channel, and metal ion transporter; and primary active transporters, e.g., P-type ATPase, arsenite-antimonite efflux, Type II secretory pathway (SecY), and sodium-transporting carboxylic acid decarboxylase. A number of other potential cognates associated with bacteria have been described in Chung, et al., *J. Bacteriology* 183: 1012-1021, 2001, which is incorporated herein by reference.

Mitochondrial Cognates

One or more tubular nanostructures may include one or more ligands that bind one or more cognates associated with an organelle, e.g., mitochondria within a tumor cell and/or other targeted cell. Examples of cognates associated with the mitochondrial outer membrane include, but are not limited to, carnitine palmitoyl transferase 2, translocase of outer membrane (TOM70), sorting/assembly machinery, ANT, voltage dependent anion channel (VDAC/Porin), and monoamine oxidase. In some instances, one or more tubular nanostructures as described herein may include one or more ligands that bind to one or more cognates on the inner mitochondrial membrane. A cognate of the inner mitochondrial membrane may be a membrane associated receptor or protein, e.g., one or more proteins associated with the carnitine acyltransferase II transporter, NADH dehydrogenase complex (Complex I), succinate dehydrogenase (Complex II), cytochrome bcl complex (Complex III), cytochrome c oxidase complex (Complex IV), ATP synthase, or uncoupling protein (UCP).

Functionalization of Tubular Nanotubes with Various Ligands that Bind to Cognates A tubular nanostructure as described herein may include one or more ligands that bind one or more cognates on a target cell or organelle. A ligand that binds a cognate may include, but is not limited to, at least a portion of an antibody, antibody-coated liposome, polynucleotide, polypeptide, receptor, viral plasmid, polymer, protein, carbohydrate, lipid, pore-forming toxin, lectin, or any combination thereof. As such, the tubular nanostructure containing one or more ligands may be selectively directed towards target cells expressing the corresponding one or more cognates. In one aspect, a protein cognate may bind to a compound having a lipid or carbohydrate moiety, e.g., a saccharide, a glycoprotein or a lipoprotein/proteolipid. The one or more ligands may be attached to the side-walls of the tubular nanostructure. Alternatively, one or more ligands may be attached to either and/or both ends of the tubular nanostructure. Increased tissue or cell specificity may be garnered by multifunctionalization of the tubular nanostructure with two or more ligands directed towards two or more distinct cognates on the target tissue. In the instance where the end targets are mitochondria in specific cells, the tubular nanostructure may be multifunctionalized, e.g., with a first ligand directed to a first cognate on the cell membrane of the target cell and with a second ligand directed to a second cognate on the membrane of the mitochondria.

Antibody Ligands

In some instances, tubular nanostructures may be modified with one or more ligands that are antibodies. Antibodies or fragments thereof for use in functionalizing a tubular nanostructure may include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies, among others. Single chain or multiple chain antigen-recognition sites can be used. Multiple chain antigen-recognition sites can be fused or unfused. Antibodies or fragments thereof may be generated using standard methods as described by Harlow & Lane (*Antibodies: A Laboratory Manual*, Cold Spring Harbor Laboratory Press; $1^{st}$ edition 1988), which is incorporated herein by reference). In another embodiment, the functional group is an antigen-binding moiety, e.g., a moiety comprising the antigen-recognition site of an antibody. Alternatively, an antibody or fragment thereof directed against a cognate may be generated using phage display technology (see, e.g., Kupper, et al. *BMC Biotechnology* 5:4, 2005, which is incorporated herein by reference). A single chain antibody, for example, may also incorporate streptavidin as part of a fusion protein to facilitate attachment of the antibody to the tubular nanostructure via a biotin-streptavidin linkage, for example (see, e.g., Koo, et al. *Appl. Environ. Microbiol.* 64:2497-2502, 1998). An antibody or fragment thereof could also be prepared using in silico design (Knappik et al., *J. Mol. Biol.* 296: 57-86, 2000, which is incorporated herein by reference). In addition or instead of an antibody, the assay may employ another type of recognition element, such as a receptor or ligand binding molecule. Such a recognition element may be a synthetic element like an artificial antibody or other mimetic. U.S. Pat. Nos. 6,255,461; 5,804,563; 6,797,522; 6,670,427; and 5,831,012; and U.S. Patent Application 20040018508; and Ye and Haupt, *Anal Bioanal Chem.* 378: 1887-1897, 2004; Peppas and Huang, *Pharm Res.* 19: 578-587 2002, provide examples of such synthetic elements and are incorporated herein by reference. In some instances, antibodies, recognition elements, or synthetic molecules that recognize a cognate may be available from a commercial source, e.g., Affibody® affinity ligands (Abcam, Inc. Cambridge, Mass. 02139-1517; U.S. Pat. No. 5,831,012, incorporated here in by reference).

Polypeptide Ligands

In some instances, tubular nanostructures may be modified with one or more ligands that are cellular receptors that recognize and/or bind to bacteria. For example, CD14, which is normally associated with monocyte/macrophages is known to bind lipopolysaccharide associated with gram negative bacteria as well as lipoteichoic acid associated with the gram positive bacteria *Bacillus subtilis* (see, e.g., Fan, et al. (1999) *Infect. Immun.* 67: 2964-2968). Other examples of cellular receptors include, but are not limited to, adenylate cyclase (*Bordatella pertussis*), Gal alpha 1-4Gal-containing isoreceptors (*E. coli*), glycoconjugate receptors (enteric bacteria), Lewis(b) blood group antigen receptor (*Heliobacter pylori*), CR3 receptor, protein kinase receptor, galactose N-acetylgalactosamine-inhibitable lectin receptor, and chemokine receptor (*Legionella*), annexin I (*Leishmania mexicana*), ActA protein (*Listeria monocytogenes*), meningococcal virulence associated Opa receptors (Meningococcus), alpha5beta3 integrin (*Mycobacterium avium*-M), heparin sulphate proteoglycan receptor, CD66 receptor, integrin receptor, membrane cofactor protein, CD46, GM1, GM2, GM3, and CD3 (*Neisseria gonorrhoeae*), KDEL receptor (Pseudomonas), epidermal growth factor receptor (*Samonella typhiurium*), alpha5beta1 integrin (Shigella), and non-glycosylated J774 receptor (*Streptococci*) (see, e.g., U.S. Patent Application 2004/0033584 A1). In some instances the pathogen specific receptor/ligand may be bound to the surface of the modified red blood cell through an antibody linkage (see, e.g., U.S. Patent Application 2006/0018912 A1, each incorporated herein by reference).

In some instances, tubular nanostructures may be modified with one or more ligands that are peptide hormones which interact with specific cognates, for example, cell surface receptors on target cells. Examples of peptide hormones that may be used to modify tubular nanostructures include, but are not limited to, neuropeptides, for example, enkephalins, neuropeptide Y, somatostatin, corticotropin-releasing hormone, gonadotropin-releasing hormone, adrenocorticotropic hormone, melanocyte-stimulating hormones, bradykinins, tachykinins, cholecystokinin, vasoactive intestinal peptide (VIP), substance P, neurotensin, vasopressin, and calcitonin; cytokines, for example, interleukins (e.g., IL-1 through IL-35), erythropoietin, thrombopoietin, interferon (IFN), granulocyte monocyte colony-stimulating factor (GM-CSF), tumor necrosis factor (TNF), and others; chemokines, e.g., RANTES, TARC, MIP-1, MCP, and others; growth factors, for example, platelet derived growth factor (PDGF), transforming growth factor beta (TGFβ); nerve growth factor (NGF), epidermal growth factor (EGF), insulin-like growth factor (IGF), basic fibroblast growth factor (bFGF); other peptide hormones, for example, atrial natriuretic factor, insulin, glucagon, angiotensin, prolactin, oxyocin, and others. In one aspect, Mattson, et al., describe functionalizing carbon nanotubes with nerve growth factor (see U.S. Pat. No. 6,670,179, which is incorporated herein by reference). Similarly, Liu, et al., describe functionalizing carbon nanotubes with cyclic arginine-glycine-aspartic acid (RGD) peptide, the latter of which is a ligand for integrin $alpha_v$-$beta_3$ receptors up-regulated in a wide range of solid tumors (Liu, et. al., *ACS Nano* 1:50-56, 2007, which is incorporated herein by reference). Alternatively, novel peptides that bind selective target, for example, tumor cells may be generated using phage display methodologies (see, e.g., Spear, et al., *Cancer Gene Ther.* 8:506-511, 2001, which is incorporated herein by reference).

Small Chemical Compound Ligands

In some aspects, the tubular nanostructure may be configured to include one or more small chemical compound ligands. As such, a tubular nanostructure may be modified with a small chemical compound ligand that interacts with a cognate on a target cell, such as a receptor. Examples of small chemical compound ligands include, but are not limited to, acetylcholine, adenosine triphosphate (ATP), adenosine, androgens, dopamine, endocannabinoids, epinephrine, folic acid, gamma-aminobutyric acid (GABA), glucocorticoids, glutamate, histamine, leukotrienes, mineralocorticoids, norepinephrine, prostaglandins, serotonin, thromoxanes, or vitamins. For example, the modification of carbon nanotubes with folic acid provides the modified nanotubes which can bind to folate receptors overexpressed on some tumor cells (see Kam et al., *Proc. Natl. Acad. Sci. USA* 102:11600-11605, 2005, which is incorporated herein by reference).

Aptamer Ligands

In some instances, tubular nanostructures may be modified with one or more ligands that are aptamers. Aptamers are artificial oligonucleotides (DNA or RNA) that can bind to a wide variety of entities (e.g., metal ions, small organic molecules, proteins, and cells) with high selectivity, specificity, and affinity. Aptamers may be isolated from a large library of $10^{14}$ to $10^{15}$ random oligonucleotide sequences using an iterative in vitro selection procedure often termed "systematic evolution of ligands by exponential enrichment" (SELEX; see, e.g., Cao, et al., *Current Proteomics* 2:31-40, 2005; Proske, et al., *Appl. Microbiol. Biotechnol.* 69:367-374, 2005, which are incorporated herein by reference). For example, an RNA aptamer may be generated against leukemia cells using a cell based SELEX method (see, e.g., Shangguan, et al., *Proc. Natl. Acad. Sci. USA* 103:11838-11843, 2006, which is incorporated herein by reference). Similarly, an aptamer that recognizes bacteria may be generated using the SELEX method against whole bacteria (see, e.g., Chen, et al., *Biochem. Biophys. Res. Commun.* 357: 743-748, 2007, which is incorporated herein by reference).

Lectin Ligands

In some embodiments, tubular nanostructures may be modified with one or more ligands that are lectins. The term "lectin" was originally used to define agglutinins which could discriminate among types of red blood cells and cause agglutination. Currently, the term "lectin" is used more generally and includes sugar-binding proteins from many sources regardless of their ability to agglutinate cells. Lectins have been found in plants, viruses, microorganisms and animals. Because of the specificity that each lectin has toward a particular carbohydrate structure, even oligosaccharides with identical sugar compositions can be distinguished or separated. Some lectins will bind only to structures with mannose or glucose residues, while others may recognize only galactose residues. Some lectins require that the particular sugar is in a terminal non-reducing position in the oligosaccharide, while others can bind to sugars within the oligosaccharide chain. Some lectins do not discriminate between a and b anomers, while others require not only the correct anomeric structure but a specific sequence of sugars for binding. Examples of lectins include, but are not limited to, algal lectins, e.g., b-prism lectin; animal lectins, e.g., tachylectin-2, C-type lectins, C-type lectin-like proteins, calnexin-calreticulin, capsid protein, chitin-binding protein, ficolins, fucolectin, H-type lectins, I-type lectins, sialoadhesin, siglec-5, siglec-7, micronemal protein, P-type lectins, pentrxin, b-trefoil, galectins, congerins, selenocosmia huwena lectin-I, Hcgp-39, Ym1; bacterial lectins, e.g., *Pseudomonas* PA-IL, *Burkholderia* lectins, chromobacterium CV-IIL, *Pseudomonas* PA IIL, Ralsonia RS-ILL, ADP-ribosylating toxin, Ralstonia lectin, Clostridium hemagglutinin, botulinum toxin, tetanus toxin, cyanobacterial lectins, FimH, GafD, PapG, Staphylococcal enterotoxin B, toxin SSL11, toxin SSL5; fungal and yeast lectins, e.g., Aleuria aurantia lectin, integrin-like lectin, *Agaricus* lectin, *Sclerotium* lectin, Xerocomus lectin, *Laetiporus* lectin, Marasmius oreades agglutinin, *agrocybe* galectin, *coprinus* galectin-2, Ig-like lectins, L-type lectins; plant lectins, e.g., alpha-D-mannose-specific plant lectins, *amaranthus* antimicrobial peptide, hevein, pokeweed lectin, *Urtica dioica* UD, wheat germ agglutinins (WGA-1, WGA-2, WGA-3), artocarpin, artocarpus hirsute AHL, banana lectin, Calsepa, heltuba, jacalin, Maclura pomifera MPA, MornigaM, Parkia lectins, abrin-a, abrus agglutinin, amaranthin, castor bean ricin B, ebulin, mistletoe lectin, TKL-1, cyanovirin-N homolog, and various legume lectins; and viral lectins, e.g., capsid protein, coat protein, fiber knob, hemagglutinin, and tailspike protein (see, e.g., E. Bettler, R. Loris, A. Imberty "3D-Lectin database: A web site for images and structural information on lectins" 3rd Electronic Glycoscience Conference, The interne and World Wide Web, 6-17 Oct. 1997; www.cermav.cnrs.fr/lectines/

Pore Forming Ligands

In some aspects, tubular nanostructures may be modified with one or more ligands that are pore-forming toxins. Examples of pore-forming toxins include, but are not limited to, beta-pore-forming toxins, e.g., hemolysin, Panton-Valentine leukocidin S, aerolysin, Clostridial epsilon-toxin; binary toxins, e.g., anthrax, *C. perfringens* iota toxin, *C. difficile* cytolethal toxins; cholesterol-dependent cytolysins; pneumolysin; small pore-forming toxins; and gramicidin A In some aspects, tubular nanostructures may be modified with one or more ligands that are pore-forming antimicrobial peptides. Antimicrobial peptides represent an abundant and diverse group of molecules that are naturally produced by many tissues and cell types in a variety of invertebrate, plant and animal species. The amino acid composition, amphipathicity, cationic charge and size of antimicrobial peptides allow them to attach to and insert into microbial membrane bilayers to form pores leading to cellular disruption and death. More than 800 different antimicrobial peptides have been identified or predicted from nucleic acid sequences, a subset of which have are available in a public database (see, e.g., Wang & Wang *Nucleic Acids Res.* 32:D590-D592, 2004); www.aps.unmc.edu/AP/main.php/, which is incorporated herein by reference). More specific examples of antimicrobial peptides include, but are not limited to, anionic peptides, e.g., maximin H5 from amphibians, small anionic peptides rich in glutamic and aspartic acids from sheep, cattle and humans, and dermcidin from humans; linear cationic alpha-helical peptides, e.g., cecropins (A), andropin, moricin, ceratotoxin, and melittin from insects, cecropin P1 from *Ascaris* nematodes, magainin (2), dermaseptin, bombinin, brevinin-1, esculentins and buforin II from amphibians, pleurocidin from skin mucous secretions of the winter flounder, seminalplasmin, BMAP, SMAP (SMAP29, ovispirin), PMAP from cattle, sheep and pigs, CAP18 from rabbits and LL37 from humans; cationic peptides enriched for specific amino acids, e.g., praline-containing peptides including abaecin from honeybees, praline- and arginine-containing peptides including apidaecins from honeybees, drosocin from *Drosophila*, pyrrhocoricin from European sap-sucking bug, bactenicins from cattle (Bac7), sheep and goats and PR-39 from pigs, praline- and phenylalanine-containing peptides including prophenin from pigs, glycine-containing peptides including hymenoptaecin from honeybees, glycine- and praline-continuing peptides including coleoptericin and holotricin from beetles, tryptophan-containing peptides including indolicidin from cattle, and small histidine-rich salivary polypeptides, including histatins from humans and higher primates; anionic and cationic peptides that contain cysteine and from disulfide bonds, e.g., peptides with one disulphide bond including brevinins, peptides with two disulfide bonds including alpha-defensins from humans (HNP-1, HNP-2, cryptidins), rabbits (NP-1) and rats, beta-defensins from humans (HBD1, DEFB118), cattle, mice, rats, pigs, goats and poultry, and rhesus theta-defensin (RTD-1) from rhesus monkey, insect defensins (defensin A); and anionic and cationic peptide fragments of larger proteins, e.g., lactoferricin from lactoferrin, casocidin 1 from human casein, and antimicrobial domains from bovine alpha-lactalbumin, human hemoglobin, lysozyme, and ovalbumin (see, e.g., Brogden, *Nat. Rev. Microbiol.* 3:238-250, 2005, which is incorporated herein by reference).

Ligands as Therapeutic Agents

In some instances, the tubular nanostructure as described herein may be configured to include one or more ligands that is a therapeutic agent. As such, the one or more therapeutic agent may contribute to disruption and/or death of the targeted cell in addition to the disruptive pore-forming capability of the tubular nanostructure. Examples of therapeutic agents that might be incorporated into the tubular nanostructure to aide in disrupting and/or killing cancer cells or microbes include anti-cancer therapeutic agents and/or antimicrobial therapeutic agents. Antimicrobial therapeutic agents may include, but are not limited to, antibacterial, antifungal and antiparasital agents.

Anti-Cancer Therapeutic Agents

In one aspect, the therapeutic agent is an anti-cancer drug. The anti-cancer drug may be selected from a variety of known small chemical compound pharmaceuticals. Alternatively, the chemotherapy agent may include, but is not limited to, an inactivating peptide nuclei acid (PNA), an RNA or DNA oligonucleotide aptamer, short double-stranded RNA (e.g., interfering RNA, microRNA), a peptide, or a protein. Examples of chemotherapy agents include, but are not limited to, antimetabolites such as capecitabine, cladribine, cytarabine, fludarabine, 5-fluorouracil, gemcitabine, 6-mercaptopurine, methotrexate, pemetrexed, and 6-thioguanine; antitumor antibiotics such as bleomycin, epipodophyllotoxins such as etoposide and teniposide; taxanes such as docetaxel and paclitaxel; vinca alkaloids such as vinblasine, vinfristine, and vinorelbine; alkylating agents such as busulfan, carmustine, cyclophosphamide, dacarbazine, ifosfamide, lomustine, mechlorethamine, melphalan, temozolomide, and thiotepa; anthracyclines such as daunorubucin, doxorubicin, epirubicin, idarubicin, and mitoxantrope; antitumor antibiotics such as dactinomycin and mitomycin; camptothecins such as irinotecan and topotecan; and platinum analogs such as carboplatin, cisplatin, and oxaliplatin; hormonally active agents such as flutamide, bicalutamide, nilutamide, tamoxifen, megestrol acetate, hydrocortisone, prednisone, goserelin acetate, leuprolide, aminoglutethimide, anastrozole, exemestane, and letrozole; and miscellaneous drugs used for cancer chemotherapy such as arsenic trioxide, erlotinib, gefitinib, imatinib, bortezomib, hydroxyurea, mitoxantrone, retinoic acid derivatives, estramustine, leucovorin and the photosensitizer Photofrin.

The anti-cancer drug may be a biological agent, e.g., a peptide, a protein, an enzyme, a receptor and/or an antibody. Examples of biological agents currently used to treat cancer include, but are not limited to, cytokines such as interferon-α, interferon-γ, and interleukin-2, an enzyme such as asparaginase, and monoclonal antibodies such as alemtuzumab, bevacizumab, cetuximab, gemtuzumab, rituximab, and trastuzumab.

Novel biological agents for the treatment of cancer may be generated by screening a peptide phage library, for example, in proliferation assays against cancerous cells, e.g., cultured transformed cells lines and/or against primary tumors from patients with various cancers (see, e.g., Spear, et al. *Cancer Gene Therapy* 8:506-511, 2001; Krag, et al. *Cancer Res.* 66:7724-7733, 2006, which are incorporated herein by reference).

Antimicrobial Therapeutic Agents

In another aspect, the therapeutic agent is an antibacterial drug. Examples of antibacterial drugs include, but are not limited to, beta-lactam compounds such as penicillin, methicillin, nafcillin, oxacillin, cloxacillin, dicloxacilin, ampicillin, ticarcillin, amoxicillin, carbenicillin, and piperacillin; cephalosporins and cephamycins such as cefadroxil, cefazolin, cephalexin, cephalothin, cephapirin, cephradine, cefaclor, cefamandole, cefonicid, cefuroxime, cefprozil, loracarbef, ceforanide, cefoxitin, cefinetazole, cefotetan, cefoperazone, cefotaxime, ceftazidime, ceftizoxime, ceftriaxone, cefixime, cefpodoxime, proxetil, cefdinir, cefditoren, pivoxil, ceftibuten, moxalactam, and cefepime; other beta-lactam drugs such as aztreonam, clavulanic acid, sulbactam, tazobactam, ertapenem, imipenem, and meropenem; other cell wall membrane active agents such as vancomycin, teicoplanin, daptomycin, fosfomycin, bacitracin, and cycloserine; tetracyclines such as tetracycline, chlortetracycline, oxytetracycline, demeclocycline, methacycline, doxycycline, minocycline, and tigecycline; macrolides such as erythromycin, clarithromycin, azithromycin, and telithromycin; aminoglycosides such as streptomycin, neomycin, kanamycin, amikacin, gentamicin, tobramycin, sisomicin, and netilmicin; sulfonamides such as sulfacytine, sulfisoxazole, silfamethizole, sulfadiazine, sulfamethoxazole, sulfapyridine, and sulfadoxine; fluoroquinolones such as ciprofloxacin, gatifloxacin, gemifloxacin, levofloxacin, lomefloxacin, moxifloxacin, norfloxacin, and ofloxacin; antimycobacteria drugs such as isoniazid, rifampin, rifabutin, rifapentine, pyrazinamide, ethambutol, ethionamide, capreomycin, clofazimine, and dapsone; and miscellaneous antimicrobials such as colistimethate sodium, methenamine hippurate, methenamine mandelate, metronidazole, mupirocin, nitrofurantoin, polymyxin B, clindamycin, choramphenicol, quinupristin-dalfopristin, linezolid, spectrinomycin, trimethoprim, pyrimethamine, and trimethoprim-sulfamethoxazole.

In another aspect, the therapeutic agent is an antifungal agent. Examples of antifungal agents include, but are not limited to, anidulafungin, amphotericin B, butaconazole, butenafine, caspofungin, clotrimazole, econazole, fluconazole, flucytosine griseofulvin, itraconazole, ketoconazole, miconazole, micafungin, naftifine, natamycin, nystatin, oxiconazole, sulconazole, terbinafine, terconazole, tioconazole, tolnaftate, and/or voriconazole.

In another aspect, the therapeutic agent is an anti-parasite agent. Examples of anti-parasite agents include, but are not limited to, antimalaria drugs such as chloroquine, amodiaquine, quinine, quinidine, mefloquine, primaquine, sulfadoxine-pyrimethamine, atovaquone-proguanil, chlorproguanil-dapsone, proguanil, doxycycline, halofantrine, lumefantrine, and artemisinins; treatments for amebiasis such as metronidazole, iodoquinol, paromomycin, diloxanide furoate, pentamidine, sodium stibogluconate, emetine, and dehydroemetine; and other anti-parasite agents such as pentamidine, nitazoxanide, suramin, melarsoprol, eflornithine, nifurtimox, clindamycin, albendazole, and timidazole.

In some instances, the antimicrobial agent may be an antimicrobial peptide. A number of naturally occurring antimicrobial peptides have been described herein and amino acid sequence information for a subset of these may be found as part of a public database (see, e.g., Wang & Wang *Nucleic Acids Res.* 32:D590-D592, 2004); www.aps.unmc.edu/AP/main.php/, which is incorporated herein by reference). Alternatively, a phage library of random peptides may be used to screen for peptides with antimicrobial properties against live bacteria, fungi and/or parasites. The DNA sequence corresponding to an antimicrobial peptide may be generated ex vivo using standard recombinant DNA and protein purification techniques and subsequently attached to tubular nanostructures using the methods described herein.

Markers on Tubular Nanostructures

In some instances, the tubular nanostructure as described herein may be configured to include one or more marker. The one or more marker may include, e.g., a fluorescent marker, a radioactive marker, a quantum dot, a contrast agent for magnetic resonance imaging (MRI) marker, or combinations thereof. One or more markers may be used to facilitate imaging of the tubular nanostructure in association with target cells or organelles.

Fluorescent Markers

In one aspect, the tubular nanostructure may include one or more markers capable of fluorescence in response to appropriate wavelengths of electromagnetic energy. The one or more fluorescent marker associated with the tubular nanostructure may include one or more of the fluorescent compounds currently approved by the United States Food and Drug Administration (FDA) for use in human mammals including, but not limited to, fluorescein (FITC), indocyanine green, and rhodamine B. FITC, for example, may be readily added to a carbon nanotube functionalized with PL-PEG-NH$_2$ as described in Kam, et al., *Proc. Natl. Acad. Sci. USA* 102:11600-11605, 2005, which is incorporated herein by reference. Alternatively, the one or more fluorescent marker associated with the tubular nanostrucure may include one or more of a number of other fluorescent compounds including, but not limited to, cyanine dyes such as Cy5, Cy5.5, and Cy7 (Amersham Biosciences, Piscataway, N.J., USA) and/or a variety of Alexa Fluor dyes including Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., USA; see, e.g., U.S. Pat. App. No. 2005/0171434 A1). Additional fluorophores include IRD41 and IRD700 (LI-COR, Lincoln, Nebr., USA), NIR-1 and 1C5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, Calif.) and VivoTag 680 (VT680; VisEn Medical, Woburn, Mass., USA). Many of these fluorophores are available from commercial sources either attached to primary or secondary antibodies or as amine-reactive succinimidyl or monosuccinimidyl esters, for example, ready for conjugation to appropriately functionalized tubular nanostructures using the methods described herein. Alternatively, the fluorophore may be added to a small single-stranded DNA and the fluorophore/DNA conjugate attached to the tubular nanostructure via non-covalent interaction between the DNA and nanotube (see, e.g., Karn, et al., *Proc. Natl. Acad. Sci. USA* 102:11600-11605, 2005, which is incorporated herein by reference).

In one aspect, the tubular nanostructure may include one or more markers that are quantum dots (Q-dots). Q-dots are nanocrystal semiconductors with unique optical properties, fluorescing at various excitation wavelengths depending upon composition and size. A variety of Q-dots are available from a number of commercial sources and may be added to tubular nanostructures through, e.g., amines, carboxyl groups, biotin, streptavidin, secondary antibodies, and phopholipid-PEG (from, e.g., Evident Technologies, Troy, N.Y.; Invitrogen, Carlsbad, Calif.). For example, Chen et al., describe adding Q-dots conjugated to streptavidin to nanotubes modified with biotin through pyrene bound to the nanotube side-wall via π-π stacking (see Chen et al., *Proc. Natl. Acad. Sci. USA* 104:8218-8222, 2007, which is incorporated herein by reference. Similarly, Didenko and Baskin describe using an enzymatic process with horseradish peroxidase to add streptavidin conjugated Q-dots to nanotubes (*BioTechniques* 40:295-302, 2006, which is incorporated herein by reference).

In a further embodiment, the tubular nanostructures themselves may be inherently fluorescent at specific wavelengths of electromagnetic energy. For example, single-walled carbon nanotubes have been shown to exhibit photoluminescence in the near infrared when excited by a diode laser at 785 nm (see, e.g., Welsher, et al., *Nano Lett* 8: 586-590, 2008, which is incorporated herein by reference).

Fluorescence associated with tubular nanostructures may be monitored using invasive and non-invasive methods. Invasive methods are exemplified by insertion of an endoscope or a catheter containing optical fibers for fluorescence excitation and measurement into body cavities or vessels (see, e.g., U.S. Pat. Nos. 7,341,557; 6,389,307, which are incorporated herein by reference). Non-invasive methods are exemplified by fluorescence mediated molecular tomography. For example, non-invasive monitoring of near infrared (NIR) fluorescence may be performed using fluorescence mediated molecular tomography as described in U.S. Pat. No. 6,615,063, which is incorporated herein by reference. Additional information regarding NIR imaging in human subjects is described in Frangioni *Curr. Op. Chem. Biol.* 7:626-634, 2003, which is incorporated herein by reference. In some instances, a wireless system may be used in which light sources such as light emitting diodes (LEDs) of appropriate wavelength as well as detectors such as charge-coupled devices (CCDs) are housed along with a power supply and a wireless communication circuit to create a device that may be placed on the skin of a subject to monitor NIR signal as described by Muehlemann, et al., *Optics Express*, 16:10323, 2008, which is incorporated herein by reference.

Radioactive Markers

In another embodiment, the tubular nanostructure may include one or more markers that are radioactive. Tubular nanostructures modified with one or more radioisotopes may be monitored using a gamma camera, positron emission tomography (PET), other gamma ray probe. Examples of radioactive molecular that might be used for this purpose include, but are not limited to, carbon-11, nitrogen-13, oxygen-15, fluorine-18, rubidium-82, yttrium-86, technetium-99, iodine-123, indium-111, thallium-201. For example, indium-111 may be added to carbon nanotubes using bifunctional metal chelating agents such as 2-(4-isothiocyanatobenzyl)-1,4,7,10-tetraazacyclododecane-1,4,7,10-tetraacetic acid (DOTA-NCS) or diethylentriaminepentaacetic (DTPA) (see, e.g., McDevitt, et al., *J. Nucl. Med.* 48:1180-1189, 2007; Singh, et al., *Proc. Natl. Acad. Sci. USA* 103:3357-3362, 2006, which are incorporated herein by reference). Similar methods are described for adding yttrium-86 to carbon nanotubes (McDevitt et al., *PLoS ONE* 2:e907, 2007, which is incorporated herein by reference).

Contrast Agent Markers

In another aspect, the tubular nanostructures may include one or more markers that are contrast agents used in magnetic resonance imaging (MRI). For example, tubular nanostructures, e.g., carbon nanotubes may be combined with the high-spin paramagnetic gadolinium ($Gd^{3+}$) metal ions to form an effective contrast agent for MRI (see, e.g., Sitharaman & Wilson *Int. J. Nanomed.* 1:291-295, 2006, which is incorporated herein by reference). Alternatively, tubular nanostructures may be functionalized with a combination of iron and cobalt salts to form MRI and near infrared imaging agents (see, e.g., Seo, et al., *Nat. Mater.* 5:971-976, 2006, which is incorporated herein by reference). Other divalent metal ions that might be included in tubular nanostructures for MRI detection include, but are not limited to, cobalt, nickel, zinc, magnesium, and manganese (see, e.g., U.S. Patent Application 2008/0124281, which is incorporated herein by reference). Alternatively, bacterial derived magnetic nanocrystals may be absorbed onto the tubular nanostructure as described in U.S. Patent Application 2007/0200085, which is incorporated herein by reference.

Activated Markers on Tubular Nanostructures

The tubular nanostructure as described herein may include one or more markers that may be activated. One or more markers associated with the tubular nanostructure may be activated by a ligand reaction, anchoring in the membrane and interaction with a hydrophobic medium, and/or change in the cellular environment (e.g., changes in pH). One or more marker associated with the tubular nanostructure may be activated upon reaching the intended target. Alternatively, one or more marker associated with the tubular nanostructure may be activated upon disruption and/or death of the target cell. Alternatively, one or more marker associated with the tubular nanostructure may be activated upon passage of the tubular nanostructure from one cellular compartment to another.

Ligand Reaction Activated Markers

The one or more activatable marker associated with the tubular nanostructure may be activated by a ligand reaction. The marker may be activated when the marker or a component associated with the marker binds to, comes in close contact with, or otherwise interacts with a ligand associated with the target cell or organelle. The marker may include a donor and an acceptor molecule that undergo fluorescence resonance energy transfer (FRET) in response to interaction of the marker with the ligand. FRET is a distance-dependent interaction between the electronic excited states of two dye molecules in which excitation is transferred from a donor molecule to an acceptor molecule without emission of a photon. In some instances, interaction of a donor molecule with an acceptor molecule may lead to a shift in the emission wavelength associated with excitation of the acceptor molecule. In other instances, interaction of a donor molecule with an acceptor molecule may lead to quenching of the donor emission.

The donor and acceptor molecules of the marker may be conjugated to the same biomolecule such that changes in the conformation of the biomolecule in response to ligand interaction move the donor and acceptor molecules relative to one another. Examples of biomolecules that might be used in this manner include, but are not limited to, polynucleotides, e.g., aptamers or polypeptides, e.g., antibodies. In this instance, the aptamers or antibodies associated with the marker may be the same aptamer or antibody used to bind the tubular nanostructure to cognates on a target cell or organelle. Alternatively, the aptamers or antibodies associated with the marker may be distinct, interacting with different components on the target cell or organelle. Other biomolecules that change conformation in response to binding a ligand may be used for this purpose.

Alternatively, the donor and acceptor molecules may be conjugated to separate biomolecules such that changes in proximity of the separate biomolecules moves the donor and acceptor molecules relative to one another. In this instance, the target cell or organelle may be modified with either a donor or acceptor molecule while the tubular nanostructure may be modified with the corresponding donor or acceptor molecule. In either instance, the interaction of the tubular nanostructure with the target cell or organelle triggers a measurable response.

Tubular nanostructures may be modified with one or more activatable marker, for example, an aptamer-based molecular beacon. Molecular beacons are dual labeled aptamer probes with a donor fluorophore at one end and an acceptor fluorophore or quencher at the other end. Upon binding of a specific target, the aptamer undergoes a conformational shift such that the distance between the donor fluorophore and the acceptor fluorophore or quencher is altered, leading to a change in measurable fluorescence through the phenomenon of FRET, as discussed above (see, e.g. Cao, et al., *Current Proteomics*, 2:31-40, 2005, which is incorporated herein by reference). In some instances, the fluorescence associated with aptamer may be quenched until the tubular nanostructure reaches its intended target. Alternatively, the fluorescence associated with the aptamer may be shifted in wavelength when the tubular nanostructure reaches its intended target.

Tubular nanostructures may be modified with one or more activatable marker that is an antibody-based molecular beacon. In this instance, the antibody may be labeled with a donor or acceptor molecule and a secondary protein associated with the antibody such as Protein A, Protein G, or a $F_{ab}$ fragment, for example, may be labeled with the corresponding donor or acceptor molecule (see, e.g., Lichlyter, et al., *Biosens. Bioelectron.* 19:219-226, 2003, which is incorporated herein by reference). Interaction of the labeled antibody/secondary protein complex with the appropriate ligand shifts the antibody and the secondary protein relative to one another and induces a FRET signal. Alternatively, the one or more marker may be an antibody labeled near the antigen-binding site with a donor or acceptor molecule and a flexible arm attached to an analog of the antigen recognized by the antibody which itself includes the corresponding donor or acceptor molecule (see, e.g. U.S. Patent Application 2006/0172318 A1). Competition for the antigen-binding site by the analog and the actual ligand on the target cell or organelle results in measurable changes in the spatial relationship between the donor and acceptor molecules. In some instances, the tubular nanostructures may be modified with a marker that is an antibody that is labeled with a solvent sensitive fluorophore, e.g., dansyl chloride (5-dimethylaminonaphthalene-1-sulfonyl chloride), and exhibits a shift in fluorescent signal in response to interaction with a ligand associated with the target cell or organelle antigen (see, e.g., Brennan *J. Fluor.* 9:295-312, 1999, which is incorporated herein by reference). An antibody of this type may be labeled such that interaction of the ligand with the antibody shields the solvent sensitive fluorescent in the active binding site from the solvent water, in a measurable change fluorescence intensity (see, e.g., Bright, et al. *Anal. Chem.* 62:1065-1069, 1990, which is incorporated herein by reference).

The donor and acceptor fluorophore pairs associated with the marker may include, but are not limited to, fluorescein and tetramethylrhodamine; IAEDANS and fluorescein; fluorescein and fluorescein; and BODIPY FL and BODIPY FL. Alternatively, the marker may include any of a number of Alexa Fluor (AF) fluorophores (from, e.g., Invitrogen, Carlsbad, Calif.) paired with other AF fluorophores for use in FRET. Some examples include AF 350 with AF 488; AF 488 with AF 546, AF 555, AF 568, or AF 647; AF 546 with AF 568, AF 594, or AF 647; AF 555 with AF594 or AF647; AF 568 with AF6456; and AF594 with AF 647.

Alternatively, the donor and acceptor fluorophore pairs associated with the marker may include cyanine dyes. The cyanine dyes Cy3, Cy5, Cy5.5 and Cy7, which emit in the red and far red wavelength range (>550 nm), offer a number of advantages for FRET-based detection systems. Their emission range is such that background fluorescence is often reduced and relatively large distances (>100 Å) can be measured as a result of the high extinction coefficients and good quantum yields. For example, Cy3, which emits maximally at 570 nm and Cy5, which emits at 670 nm, may be used as a donor-acceptor pair. When the Cy3 and Cy5 are not proximal to one another, excitation at 540 nm results only in the emission of light by Cy3 at 590 nm. In contrast, when Cy3 and Cy5 are brought into proximity by a conformation change in an aptamer, for example, excitation at 540 nm results in an emission at 680 nm.

Alternatively, the donor or acceptor molecular of the marker may include one or more semiconductor quantum dots (Q-dots) paired with an appropriate organic dye donor or acceptor molecule as described by Bawendi, et al., in U.S. Pat. No. 6,306,610, which is incorporated herein by reference.

In some instances, the donor molecule of the marker may be a quenching dye that quenches the fluorescence of visible light-excited fluorophores when in close proximity. Examples include DABCYL, the non-fluorescing diarylrhodamine derivative dyes QSY 7, QSY 9 and QSY 21 (from, e.g., Invitrogen, Carlsbad, Calif.), the non-fluorescing Black Hole Quenchers BHQ0, BHQ1, BHQ2, and BHQ3 (from, e.g., Biosearch Technologies, Inc., Novato, Calif., USA) and Eclipse (from, e.g., Applera Corp., Norwalk, Conn., USA). A variety of donor fluorophore and quencher pairs may be considered for FRET including but not limited to fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (from, e.g., Invitrogen, Carlsbad, Calif.) may be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

In some instances, the tubular nanostructure itself may act as a quencher. Carbon nanotubes, for example, can act collectively as quenchers of covalently tethered and/or π stacked pyrenes and chromophores. This phenomenon is attributed to electron transfer or energy transfer from the photoactive compound to the carbon nanotubes if sufficiently close in proximity. As such, fluorescence emitted by chromophores bound to carbon nanotubes may be quenched by the association. For example, lysophospholipid 1,2-dipalmitoyl-sn-glycero-3-lysophosphoethanolamine-N-(Liss-amine rhodamine B sulfonyl), or Rd-LPE may be added to carbon nanotubes as described by Lin et al. (*Appl. Phys. Lett.* 89:143118, 2006, which is incorporated herein by reference). In this instance, Rd-LPE solubilizes carbon nanotubes in aqueous solution via pure hydrophobic interactions and these self-assembled supramolecular complexes, once excited, readily undergo fluorescence energy transfer from the Rd-LPE to the carbon nanotubes, quenching the rhodamine associated fluorescence. This energy transfer may be used to detect membrane translocation of modified carbon nanotubes and dissociation of Rd-LPE in cells, for example. During translocation through the plasma membrane, the lipid-rhodamine moiety may be transferred off the carbon nanotubes and as such the quenching is removed and the rhodamine associated fluorescence is detected. Alternatively, the lipid rhodamine moiety is stripped from the carbon nanotube during entry into the cell, quenching is removed and rhodamine associated fluorescence is detected.

Lipid translocation in combination with carbon nanotubes crossing the membrane is accompanied by lipid flip or lipid flip-flop within the lipid bilayer membrane.

Lipid Membrane Reactive Markers

The one or more activatable marker associated with the tubular nanostructure may be activated by a lipid versus aqueous environment. As such, incorporation of the tubular nanostructure modified with an activatable marker that is lipid sensitive into the lipid bilayer of a target tissue or organelle may result in a measurable response. For example, the marker may be a fluorescent dye such as one of several aminonaphthlethenyl-pyridinium (ANEP) dyes which are essentially non-fluorescent in an aqueous environment but fluoresce within a lipid environment. Examples of lipid sensitive fluorescent ANEP dyes include, but are not limited to, di-4ANEPPS and di-8-ANEPPS. When bound to phospholipid vesicles, di-8-ANEPPS has excitation/emission maxima of ~467/631 nm. The fluorescence excitation/emission maxima of di-4-ANEPPS bound to neuronal membranes, for example, are ~475/617 nm.

Alternatively, the marker may be a derivative of nitrobenzoxadiazole (NBD) which is almost non-fluorescent in aqueous solvents. The NBD fluorophore is moderately polar and both its homologous 6-carbon and 12-carbon fatty acid analogs and the phospholipids derived from these probes may be used to sense the lipid-water interface region of membranes.

The marker may be fluorescent phospholipid analog β-DPH HPC which comprises diphenylhexatriene propionic acid coupled to glycerophosphocholine at the sn-2 position. DPH and its derivatives exhibit strong fluorescence enhancement when incorporated into membranes, as well as sensitive fluorescence polarization (anisotropy) responses to lipid ordering. β-DPH HPC may be used to specifically label one leaflet of a lipid bilayer, thus facilitating analysis of membrane asymmetry.

A number of phospholipid analogs with pyrene-labeled sn-2 acyl chains, e.g., 4-hydroxy-N,N,N-trimethyl-10-oxo-7-((1-oxo-10-(1-pyrenyl)decyl)oxy)-hydroxide are also non-fluorescent in aqueous solution but become fluorescent in a lipid environment. Various pyrenedecanoyl-labeled glycerophospholipids may be used for this purpose including but not limited to those with phosphocholine, phosphoglycerol, and phosphomethanol head groups.

Alternatively, the marker may be a derivative of the polyunsaturated fatty acid cis-parinaric acid which offers several experimentally advantageous optical properties, including a very large fluorescence Stokes shift (~100 nm) and an almost complete lack of fluorescence in water.

Cell Environment Reactive Markers

The one or more activatable marker associated with the tubular nanostructure may be activated in response to the cellular environment. For example, the marker may be activated by changes pH and/or by enzymatic reactions associated with lipid bilayer and/or components of the cytoplasm.

The tubular nanostructures may include a marker that is sensitive to pH changes in the cellular environment. For example, the marker may be a pH sensitive fluorescent dye such as LysoSensor Yellow/Blue DND-160 (Invitrogen, Carlsbad, Calif.) which undergoes a pH dependent emission and excitation shift to longer wavelengths in acidic environments. Examples of pH sensitive dyes include, but are not limited to, other LysoSensor probes, e.g., LysoSensor Blue DND-167 and LysoSensor Green DND-189 which are almost nonfluorescent except when inside acidic compartments; and fluorescein containing dyes such as dichlorofluorescein, carboxydichlorofluorescein, carboxydifluorofluorescein, and BCECF; and Oregon Green 514 carboxylic acid, Oregon Green 488 carboxylic acid, 5-(and 6-)carboxy-2',7'-, 9-amino-6-chloro-2-methoxyacridine (ACMA) (e.g., from Invitrogen, Carlsbad, Calif.).

The tubular nanostructures may include a marker that is activated by a chemical process. For example, the marker may be a bis-BODIPY FL $C_{11}$-PC which has BODIPY FL dye-labeled sn-1 and sn-2 acyl groups, resulting in partially quenched fluorescence that increases when one of the acyl groups is hydrolyzed by phospholipase $A_1$ or $A_2$. The phospholipase may be associated with either the membrane or the cytoplasm. The hydrolysis products are BODIPY FL undecanoic acid and BODIPY FL dye-labeled lysophosphatidylcholine. Other examples include markers that are linked to the tubular nanostructures through a cleavable disulfide bond, ester linkage, or ortho carboxy phenol derived acetal linkage (see, e.g., U.S. Pat. Nos. 7,087,770 and 7,348,453, which are incorporated herein by reference). For example, Q-dots linked to carbon nanotubes by disulfide bond may be cleaved from the nanotubes upon entry into the cell (see, e.g., Chen, et al., Proc. Natl. Acad. Sci. USA 104:8218-8222, 2007, which is incorporated herein by reference). As such, donor and acceptor molecules associated with the marker may be separated from one another by breaking a cleavable bond, resulting in a measurable signal.

Assemblies of Tubular Nanostructures

The one or more tubular nanostructures as described herein may be individual, discrete nanotubes. Alternatively, tubular nanostructures may form higher order assemblies or compositive tubular nanostructures. A composite tubular nanostructure may comprise two or more tubular nanostructures each including a hydrophobic surface region, each hydrophobic region flanked by two hydrophilic surface regions configured to form a pore in a lipid bilayer membrane. Composite tubular nanostructures may be used to create multiple pores at one or more sites in the targeted lipid bilayer.

In general, carbon nanotubes, for example, have a tendency to form large, insoluble aggregates due to substantial van der Waals interactions. As such, solubilization techniques may be used to break up these aggregates into smaller bundles and/or individual nanotubes. The nanotubes may be solubilized by acid oxidation, by surfactants, by polymer wrapping and/or by chemical functionalization, for example. Solubilization in acid or surfactant or other solubilizing agent such as polyoxometalates, for example, may be carried out in the presence of sonication and may be monitored using scanning and/or transmission electron microscopy (see, e.g., Fei, et al., Nanotechnol. 17:1589-1593, 2006, which is incorporated herein by reference). Alternatively, Raman spectroscopy may be used to monitor disaggregation of carbon nanotubes. For example, Raman signals at 266 $cm^{-1}$ correspond to aggregated nanotube bundles whereas a broad photoluminescence peak observed at approximately 3,200 $cm^{-1}$ (1,050 nm) corresponds to individual tubes (see, e.g., Kam, et al., Proc. Natl. Acad. Sci. USA 102:11600-11605, 2005, which is incorporated herein by reference). There is evidence to suggest that electron and ion irradiation of nanotubes give rise to covalent bonds between tubes in bundles (see, e.g., Sammalkorpi, et al., Nucl. Instr. Methods Phys. Res. B 228:142-145, 2005; Szabados, et al., Phys. Rev. 73:195404, 2006, which are incorporated herein by reference).

In a further aspect, bundles of two or more tubular nanostructures may be formed by modification of the nanotube sidewall that confers attraction between individual nanotubes. For example, bundles of two or more tubular nanostructures may be formed by combining an appropriate ratio of nanotubes modified with biotin and nanotubes modified with streptavidin. Other biomolecule binding interactions that might be used to construct composite tubular nanostructures include, but are not limited to, protein-protein interactions, antibody-antigen interactions, sense-antisense DNA or RNA interactions, aptamer-target interaction, peptide-nucleic acid (PNA)-DNA or RNA interactions. Biomolecules for use in forming higher ordered bundles of tubular nanostructures may be added to the nanotubes using one or more of the methods described herein. Optionally, asymmetric sidewall functionalization in which one surface or portion of a surface is masked during the functionalization process may be used to selectively place biomolecules on the surface of tubular nanostructures as described herein. As such, the compatible surfaces are expected to come together to form composite tubular nanostructures.

Two or more tubular nanostructures may be bundled together through the interaction of biomolecules associated with the nanotubes that normally oligomerize into higher order complexes. Tubular nanostructures may be modified with a protein or proteins that naturally form a triplex, for example, and as such would bring together three associated nanotubes. An example is the ATP responsive, cation-selective ion channels P2X1, P2X2, and P2X3 which have been shown by various means including atomic force microscopy to form trimeric structures (see, e.g., Barrera, et al., *J. Biol. Chem.* 280:10759-10765, 2005, which is incorporated herein by reference). Alternatively, tubular nanostructures may be modified with a protein or proteins that naturally form a heptamer and as such would bring together seven associated nanotubes. An example is the pore-forming toxin hemolysin which forms a heptameric beta-barrel structure in biological membranes.

Assembly of Tubular Nanostructures Enabling Active Transport, Facilitated Transport, or Passive Transport Tubular nanostructures as described herein may be further modified to control flow of biomolecules through the pores formed by the nanotubes in the lipid bilayer. For example, tubular nanostructures may be modified with one or more proteins or peptides that facilitate active and or passive transport across the pore. Active transport requires an external energy source, e.g., the hydrolysis of ATP to transport biomolecules such as ions against a concentration gradient, the biomolecules moving, for example, from low to high concentration. In contrast, passive transport is driven by the concentration gradient of the biomolecule across an open pore, the biomolecules moving from high to low concentration to establish equilibrium. Facilitated transport is a form of passive transport in which materials are moved across the plasma membrane by a transport protein down their concentration gradient; hence, it does not require energy. Biomolecules that are involved in active transport, facilitated transport, or passive transport of molecules across the lipid bilayer may be incorporated into the tubular nanostructures.

Tubular nanostructures may be include one or more components of an ATP-binding cassette transporters (ABC transporters). ABC transporters are composed of transmembrane domains connected to one or more ligand binding domains on either the intracellular or extracellular side of the lipid bilayer and one or more ATP binding domains on the intracellular surface. ATP transporters may be classified as half or full transporters. Full transporters may contain two transmembrane domains and two ATP binding domains and are fully functional. Half transporters contain one transdomain and one ATP binding domain and must combine with another half transporter to be fully functional. As such, a tubular nanostructure may include all or part of a full transporter sufficient to confer functionality. Alternatively, a tubular nanostructure may include half of a full transporter or all of part of a half transporter which upon interacting with one or more similarly modified tubular nanostructure generates a functional ABC transporter.

One or more tubular nanostructures may include all or part of an ABC transporter, for example, the cystic fibrosis transmembrane conductance regulator (CFTR), the transporter associated with antigen processing (TAP), or the multidrug resistance efflux pump (MDR). There are seven distinct gene families of ABC transporters found in humans including, but not limited to, ABCA, ABCB, ABCD, ABCE, ABCF, and ABCG, with each family consisting of 1 to 12 members. Examples of ABC transporter genes found in prokaryotes include, but are not limited to, transporters such as Carbohydrate Uptake Transporter-1 (CUT1), Carbohydrate Uptake Transporter-2 (CUT2), Polar Amino Acid Uptake Transporter (PAAT), Peptide/Opine/Nickel Uptake Transporter (PepT), Hydrophobic Amino Acid Uptake Transporter (HAAT), Sulfate/Tungstate Uptake Transporter (SulT), Phosphate Uptake Transporter (PhoT), Molybdate Uptake Transporter (MolT), Phosphonate Uptake Transporter (PhnT), Ferric Iron Uptake Transporter (FeT), Polyamine/Opine/Phosphonate Uptake Transporter (POPT), Quaternary Amine Uptake Transporter (QAT), Vitamin B12 Uptake Transporter (B12T), Iron Chelate Uptake Transporter (FeCT), Manganese/Zinc/Iron Chelate Uptake Transporter (MZT), Nitrate/Nitrite/Cyanate Uptake Transporter (NitT), Taurine Uptake Transporter (TauT), Cobalt Uptake Transporter (CoT), Thiamin Uptake Transporter (ThiT). Brachyspira Iron Transporter (BIT), Siderophore-Fe3+ Uptake Transporter (SIUT), Nickel Uptake Transporter (NiT), Nickel/Cobalt Uptake Transporter (NiCoT), and Methionine Uptake Transporter (MUT); and exporters such as Lipid Exporter (LipidE), Capsular Polysaccharide Exporter (CPSE), Lipooligosaccharide Exporter (LOSE), Lipopolysaccharide Exporter (LPSE), Teichoic Acid Exporter (TAE), Drug Exporter-1 (DrugE1), Lipid Exporter (LipidE), Putative Heme Exporter (HemeE), β-Glucan Exporter (GlucanE), Protein-1 Exporter (Prot1E), Protein-2 Exporter (Prot2E), Peptide-1 Exporter (Pep1E), Peptide-2 Exporter (Pep2E), Peptide-3 Exporter (Pep3E), Probable Glycolipid Exporter (DevE), Na+ Exporter (NatE), Microcin B17 Exporter (McbE), Drug Exporter-2 (DrugE2), Microcin J25 Exporter (McjD), Drug/Siderophore Exporter-3 (DrugE3), (Putative) Drug Resistance ATPase-1 (Drug RA1), (Putative) Drug Resistance ATPase-2 (Drug RA2), Macrolide Exporter (MacB), Peptide-4 Exporter (Pep4E), 3-component Peptide-5 Exporter (Pep5E), Lipoprotein Translocase (LPT), β-Exotoxin I Exporter ((βETE), AmfS Peptide Exporter (AmfS-E), SkfA Peptide Exporter (SkfA-E), and CydDC Cysteine Exporter (CydDC-E).

Alternatively, the tubular nanostructures may include one or more components of an ion channel. Ion channels are integral membrane proteins that regulate the flow of ions across the cell membrane and often include a circular arrangement of identical or homologous proteins closely packed around a water-filled pore through the plane of the lipid bilayer. The pore-forming subunit(s) are called the α subunit, while the auxiliary subunits are denoted β, γ, and so on. In some ion channels, passage through the pore is governed by a "gate," which may be opened or closed by chemical or electrical signals, temperature, or mechanical force, depending on the variety of channel. Examples of ion channels that might be incorporated into one or more tubular nanostructures include, but are not limited to, voltage-gated sodium, calcium and potassium channels, voltage gated proton channels, transient receptor potential channels (TRP), cyclic nucleotide-gated channels, light gated channels, inward-rectifier potassium channels, calcium-activated potassium channels, and ligand gated channels, e.g., ionotropic glutamate-gated receptors, ATP-gated P2X receptors, and anion-permeable gamma-aminobutyric acid-gated GABA receptors.

In some instances, the tubular nanostructures may include one or more components that alone or in combination form a synthetic ion channel. Compounds that might be used to form synthetic ion channels include, but are not limited to, crown ethers, octiphenyl derivatives, octa- and decapeptides, and bolaamphiphiles (two-headed amphiphiles; see, e.g., Fyles *Chem. Soc. Rev.* 36: 335-347, 2007, which is incorporated herein by reference).

In some instances, opening or closing of the pore associated with the tubular nanostructure may be controlled by a component of the tubular nanostructure that reversibly covers and or uncovers the one or more pore openings. For example, the tubular nanostructures may include one or more components at one or both pore openings that change in conformation in response stimuli such as, for example, pH, temperature, electric field, light, and or ligand binding. Conformational changes in proteins, for example, in response to stimuli may modulate activity of the protein and or play a role in signal transduction. An example is the glutamate receptor family of glutamate binding proteins in which the glutamate binding domain is in a clam-shell like hinge region which opens in the absence of glutamate and closes in the presence of glutamate (see, e.g., Dinglehine, et al., *Pharmacol. Rev.* 51:7-62, 1999, which is incorporated herein by reference). Similarly, DNA and RNA biomolecules such as aptamers, for example, may be designed to change in conformation in response to ligand binding (see, e.g., Ha, et al., *PNAS* 96:9077-9082, 1999, which is incorporated herein by reference). As such, the tubular nanostructure may be modified with a biomolecule such as a protein or an aptamer at one or both pore openings that is able to open and close in response to ligand binding and as such can control the flow of other biomolecules through the pore.

Alternatively, the tubular nanostructures may include one or more components at one or both pore openings that is responsive to light or electromagnetic energy. Electromagnetic energy may include gamma rays, x-rays, ultraviolet, visible, infrared, microwave and or radio waves. In this instance, the one or more component may contain one or more cleavage sites, for example, that are activated by electromagnetic energy and results in removal of portion of the component that may be covering the pore opening. For example, Rock, et al., describe a number of dithiane adduct derivatives that may be used with proteins as photolabile linkers (U.S. Pat. No. 5,767,288, which is incorporated herein by reference). Alternatively, the energy activated component may change conformation in response to electromagnetic energy and as such cover or uncover the pore opening.

In a further aspect, the tubular nanotubes may include components that are magnetic and allow binding of one or both ends of the pore to a magnet bead that physically blocks the pore opening. For example, one or both ends of the tubular nanostructure may be modified with molecules having magnetic properties. Examples of molecules having magnetic properties include but are not limited to the common magnetic metals iron, nickel, and cobalt and their alloys as well as the rare earth metals and alloys or combinations thereof such as for example gadolinium, samarium, and europium. Tubular nanostructures such as carbon nanotubes, for example, may be functionalized with iron and or gadolinium, for example, using methods described in Seo, et al., (*Nat. Mater.* 5:971-976, 2006) and Sitharaman & Wilson (*Int. J. Nanomed.* 1:291-295, 2006), respectively, which are incorporated herein by reference. The magnetized tubular nanotubes may be administered to a subject to form pores in targeted lipid membranes, and magnetic beads administered at a subsequent time point to block the pore opening. Alternatively, the magnetized tubular structures may be combined with magnetic beads prior to administration, and an external magnetic source, for example, may be used to separate the beads from the nanotubes.

In some instances, the pore associated with the tubular nanostructure may be covered by a nanoparticle such as for example a bead which has been modified with an aptamer or antibody, for example, that binds to a corresponding ligand at one or both ends of the tubular nanostructure. Alternatively, the nanoparticle may include streptavidin or biotin which binds to biotin or streptavidin, respectively, at the end of the tubular nanostructure.

The tubular nanostructures may be further modified to allow for controlled release of an agent such as, for example, a therapeutic agent and or toxin in proximity to the pore opening. For example, the tubular nanotubes may include a binding moiety such as an aptamer or antibody situated at one or both ends of the tubular nanostructure to which is reversibly bound an agent. The affinity of the antibody for the agent is such that the agent dissociates from the antibody and because of its proximity to the pore, has a higher probability of passing through the pore. Alternatively, the tubular nanostructure may include a ligand that is recognized by a bifunctional binding moiety such as, for example, a bifunctional antibody. In this instance, the bifunctional antibody has a component that binds to a ligand on the tubular nanostructure as well as a component that reversibly binds to an agent such as, for example, a therapeutic agent and or toxin. In this instance, the bifunctional antibody carrying an agent may be administered to the subject at a point in time following administration of the tubular nanostructures. As such, the tubular nanostructure embedded into the lipid bilayer, binds the bifunctional antibody, and over time, the agent is released from the bifunctional antibody and passes through the lipid bilayer by way of the proximal tubular nanostructure pore.

Tubular Nanostructure Directed to Specific Organelles

In some instances, the tubular nanostructures as described herein may be modified in such a manner as to allow transit of the nanotubes through the plasma membrane with subsequent targeting and insertion into the lipid bilayer of one or more internal organelles. Once targeted to the lipid bilayer of the organelle membrane, the tubular nanostructure may form pores that enable active transport, facilitated transport, or passive transport of contents into or out of the organelle. In certain organelles, disruption of the lipid bilayer may lead to cell death. In one example, the membrane target is the outer membrane of mitochondria. In general, mitochondrial outer membrane permeabilization is considered the "point of no return" during apoptosis of cells as it results in the diffusion to the cytosol of numerous proteins that normally reside in the space between the outer and inner mitochondrial membranes and initiates a cascade of events leading to cell death (see, e.g., Chipuk, et al., *Cell Death Differ.* 13:1396-1402, 2006, which is incorporated herein by reference). As such, tubular nanostructures may be selectively directed to the outer membrane of mitochondria in target cells where they insert into and disrupt the outer mitochondrial membrane leading to target cell death.

The tubular nanostructures with hydrophobic surface region flanked by two hydrophilic surface regions for insertion and retention in a lipid bilayer may be modified in such a manner as to mask the hydrophilic ends and allow transit through the plasma membrane. In one embodiment, the hydrophilic ends of the tubular nanostructure are modified with a hydrophobic moiety through a chemical bond that may be cleaved once the nanotube has passed into the cell. Examples of biologically cleavable bonds include, but are not limited to, disulfide bonds, diols, diazo bonds, ester bonds, sulfone bonds, acetals, ketals, enol ethers, enol esters, enamines and imines (see, e.g., U.S. Pat. Nos. 7,087,770, 7,098,030 and 7,348,453, which are incorporated herein by reference).

Alternatively, the cleavable bond may be a photolabile bond. Examples of hydrophobic moieties that might be added to the ends of the tubular nanostructure include, but are not limited to, non-polar hydrocarbon chains of various lengths. In one aspect, the hydrophobic moiety is an ester that can be cleaved by an intracellular esterase to form a hydrophilic acid moiety and alcohol moiety. For example, hydrophilic moieties may be masked by acetoxymethyl esters of phosphates, sulfates, or other compounds having alcohol moieties or acid moieties which will enhance permeability of the tubular nanostructure across the lipid bilayer membrane. Because acetoxymethyl esters are rapidly cleaved intracellularly, they facilitate the delivery of tubular nanostructures into the cytoplasm of the cell without puncturing or disruption of the cell plasma membrane (see, e.g., Schultz et al., *J. Biol. Chem.* 268: 6316-6322, 1993, which are incorporated herein by reference). Once within the cytoplasm, the tubular nanostructures having a hydrophobic surface region flanked by two hydrophilic surface regions is configured to form a pore in the lipid bilayer membrane of the cellular organelle.

Alternatively, the tubular nanostructure may be tethered to a protein transduction domain (PTD) such as human immunodeficiency virus type 1 (HIV-1) transactivator of transcription (Tat), *Drosophila* Antennapedia (Antp), or herpes simplex virus VP22 that masks the hydrophilic ends and facilitates entry of the nanotubes into the cell. In one aspect, all or part of the 86 amino acid long Tat protein may be added to tubular nanostructures through primary amines associated with the peptide and/or the functionalized nanotubes using the methods described herein (also see, e.g., Santra, et al., *Chem. Commun.* 24:2810-2811, 2004, which is incorporated herein by reference). The Tat protein or other protein transduction domain may be linked to the tubular nanostructure to the hydrophilic regions on either end of the nanotube through a cleavable bond such as those described herein and as such removed from the tubular nanostructure once the latter has entered the cell, unmasking the hydrophilic regions.

Under certain conditions, the masked tubular nanostructures may be actively taken up by the cell through the process of endocytosis (see, e.g., Kam, et al., *Angew. Chem. Int. Ed.* 44:1-6, 2005, which is incorporated herein by reference). Endocytosis is the process whereby cells absorb extracellular material by engulfing the material with their cell membrane. The engulfed material is contained in small vesicles that pinch off from the plasma membrane, enter the cytoplasm and fuse with other intracellular vesicles, e.g., endosomes or lysosomes.

Material such as tubular nanostructures may be released from endosomes by a number of mechanisms. In one aspect, artificial acceleration of endosomal release may be achieved by photo-excitation of fluorescent probes associated with the engulfed material (see, e.g., Matsushita, et al., *FEBS Lett.* 572:221-226, 2004, which is incorporated herein by reference). Alternatively, the tubular nanostructure may include a pH sensitive element that is activated in the low pH environment of the endosome. In a further aspect, all or part of the influenza virus hemagglutinin-2 subunit (HA-2), a pH-dependent fusogenic peptide that induces lysis of membranes at low pH, may be used to induce efficient release of encapsulated material from cellular endosomes (see, e.g., Yoshikawa, et al., *J. Mol. Biol.* 380:777-782, 2008, which is incorporated herein by reference).

Alternatively, the masked tubular nanostructures may enter the cell by passing directly through the cell membrane and into the cytoplasm. In this instance, the tubular nanostructure may include moieties on the surface of the nanotubes that confers direct passage through the lipid bilayer, e.g., an amphiphilic striated surface on the nanotube. The deposition of a hydrophilic-hydrophobic striated pattern of molecules, e.g., the anionic ligand 11-mercapto-1-undecanesulphonate (MUS) and the hydrophobic ligand 1-octanethiol (OT) on the surface of nanotubes may facilitate direct passage of the tubular nanostructures into the cytoplasm (see, e.g., Verma, et al., *Nature Materials* 7: 588-95, 2008, which is incorporated herein by reference). Once the masked tubular nanostructures has entered the cytoplasm, it can be modified to reveal tubular nanostructures with hydrophobic surface region flanked by two hydrophilic surface regions and at least one ligand bound to the nanostructure and configured to bind one or more cognates on an organellar membrane, e.g., a mitochondrial membrane.

The one or more tubular nanostructures may include one or more ligands that binds to one or more cognate on a cellular organelle, e.g., mitochondria, as well as one or more ligand that binds to one or more cognates on the cell surface membrane of the target cell. The one or more ligands may be an antibody, antibody-coated liposome, polynucleotide, polypeptide, receptor, viral plasmid, polymer, protein, carbohydrate, lipid, toxin, lectin, or any combination thereof as described herein. Cognates associated with a mitochondrial membrane may include at least one of a protein, a carbohydrate, a glycoprotein, a glycolipid, a sphingolipid, a glycerolipid, or metabolites thereof. Examples of cognates associated with the mitochondrial outer membrane, for example, include, but are not limited to, carnitine palmitoyl transferase 2, translocase of outer membrane (TOM70), sorting/assembly machinery, ANT, voltage dependent anion channel (VDAC/Porin), and monoamine oxidase. In some instances, one or more tubular nanostructures may include one or more ligands that bind to one or more cognates on the inner mitochondrial membrane. A cognate of the inner mitochondrial membrane may be a membrane associated receptor or protein, e.g., one or more proteins associated with the carnitine acyltransferase II transporter, NADH dehydrogenase complex (Complex I), succinate dehydrogenase (Complex II), cytochrome bc1 complex (Complex III), cytochrome c oxidase complex (Complex IV), ATP synthase, or uncoupling protein (UCP).

Pharmaceutical Formulation of a Tubular Nanostructure and Administration to a Subject The compositions and methods described herein for inserting a tubular nanostructure into a lipid bilayer membrane are useful for treatment of a disease or condition, e.g., cancer or infectious disease, in a mammalian subject in need thereof. A pharmaceutical formulation including the tubular nanostructures or the composite tubular nanostructures described herein may be formulated neat or may be combined with one or more acceptable carriers, diluents, excipients, and/or vehicles such as, for example, buffers, surfactants, preservatives, solubilizing agents, isotoni city agents, and stablilizing agents as appropriate. A "pharmaceutically acceptable" carrier, for example, may be approved by a regulatory agency of the state and/or Federal government such as, for example, the United States Food and Drug Administration (US FDA) or listed in the U.S. Pharmacopeia or other generally recognized pharmacopeia for use in animals, and more particularly in humans. Conventional formulation techniques generally known to practitioners are described in Remington: *The Science and Practice of Pharmacy*, 20th Edition, Lippincott Williams & White, Baltimore, Md. (2000), which is incorporated herein by reference.

Acceptable pharmaceutical carriers include, but are not limited to, the following: sugars, such as lactose, glucose and sucrose; starches, such as corn starch and potato starch; cellulose, and its derivatives, such as sodium carboxymethyl cellulose, ethyl cellulose, cellulose acetate, and hydroxymethylcellulose; polyvinylpyrrolidone; cyclodextrin and amylose; powdered tragacanth; malt; gelatin, agar and pectin; talc; oils, such as mineral oil, polyhydroxyethoxylated castor oil, peanut oil, cottonseed oil, safflower oil, sesame oil, olive oil, corn oil and soybean oil; polysaccharides, such as alginic acid and acacia; fatty acids and fatty acid derivatives, such as stearic acid, magnesium and sodium stearate, fatty acid amines, pentaerythritol fatty acid esters; and fatty acid monoglycerides and diglycerides; glycols, such as propylene glycol; polyols, such as glycerin, sorbitol, mannitol and polyethylene glycol; esters, such as ethyl oleate and ethyl laurate; buffering agents, such as magnesium hydroxide, aluminum hydroxide and sodium benzoate/benzoic acid; water; isotonic saline; Ringer's solution; ethyl alcohol; phosphate buffer solutions; other non-toxic compatible substances employed in pharmaceutical compositions.

A pharmaceutical formulation including the tubular nanostructures or the composite tubular nanostructures described herein may be formulated in a pharmaceutically acceptable liquid carrier. The liquid carrier or vehicle may be a solvent or liquid dispersion medium comprising, for example, water, saline solution, ethanol, a polyol, vegetable oils, nontoxic glyceryl esters, and suitable mixtures thereof. The solubility of a chemical blocking agent may be enhanced using solubility enhancers such as, for example, water; diols, such as propylene glycol and glycerol; mono-alcohols, such as ethanol, propanol, and higher alcohols; DMSO (dimethylsulfoxide); dimethylformamide, N,N-dimethylacetamide; 2-pyrrolidone, N-(2-hydroxyethyl) pyrrolidone, N-methylpyrrolidone, 1-dodecylazacycloheptan-2-one and other n-substituted-alkyl-azacycloalkyl-2-ones and other n-substituted-alkyl-azacycloalkyl-2-ones (azones). The proper fluidity may be maintained, for example, by the formation of liposomes, by the maintenance of the necessary particle size in the case of dispersions or by the use of surfactants. One or more antimicrobial agent may be included in the formulation such as, for example, parabens, chlorobutanol, phenol, sorbic acid, and/or thimerosal to prevent microbial contamination. In some instances, it may be preferable to include isotonic agents such as, for example, sugars, buffers, sodium chloride or combinations thereof.

A pharmaceutical formulation including the tubular nanostructures or the composite tubular nanostructures described herein may be formulated for transdermal delivery. For example, water-insoluble, stratum corneum-lipid modifiers such as for example 1,3-dioxanes, 1,3-dioxolanes and derivatives thereof, 5-, 6-, 7-, or 8-numbered lactams (e.g., butyrolactam, caprolactam), morpholine, cycloalkylene carbonate have been described for use in transdermal iontophoresis (see, e.g., U.S. Pat. No. 5,527,797, which is incorporated herein by reference). Other suitable penetration-enhancing agents include but are not limited to ethanol, hexanol, cyclohexanol, polyethylene glycol monolaurate, azacycloalkan-2-ones, linoleic acid, capric acid, lauric acid, neodecanoic acid hexane, cyclohexane, isopropylbenzene; aldehydes and ketones such as cyclohexanone, acetamide; N,N-di(lower alkyl)acetamides such as N,N-diethylacetamide, N,N-dimethyl acetamide; N-(2-hydroxyethyl)acetamide; esters such as N,N-di-lower alkyl sulfoxides; essential oils such as propylene glycol, glycerine, isopropyl myristate, and ethyl oleate; salicylates; and mixtures of any of the above (see, e.g., U.S. Patent Publication 2008/0119449).

In some instances, the pharmaceutical formulation including the tubular nanostructures or the composite tubular nanostructures described herein may be formulated in a dispersed or dissolved form in a hydrogel or polymer associated with, for example, implantable or a transdermal delivery method. Examples of hydrogels and/or polymers include but are not limited to gelled and/or cross-linked water swellable polyolefins, polycarbonates, polyesters, polyamides, polyethers, polyepoxides and polyurethanes such as, for example, poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(allyl alcohol). Other suitable polymers include but are not limited to cellulose ethers, methyl cellulose ethers, cellulose and hydroxylated cellulose, methyl cellulose and hydroxylated methyl cellulose, gums such as guar, locust, karaya, xanthan gelatin, and derivatives thereof. For iontophoresis, for example, the polymer or polymers may include an ionizable group such as, for example, (alkyl, aryl or aralkyl) carboxylic, phosphoric, glycolic or sulfonic acids, (alkyl, aryl or aralkyl) quaternary ammonium salts and protonated amines and/or other positively charged species as described in U.S. Pat. No. 5,558,633, which is incorporated herein by reference in its entirety.

Information regarding formulation of FDA approved tubular nanostructures or the composite tubular nanostructures may be found in the package insert and labeling documentation associated with each approved agent. A compendium of package inserts and FDA approved labeling may be found in the Physician's Desk Reference. Alternatively, formulation information for approved chemical blocking agents may be found on the interne at websites such as, for example, www.drugs.com and www.rxlist.com. For those tubular nanostructures or composite tubular nanostructures described herein which do not currently have a formulation appropriate for use in any of the delivery methods described above, an appropriate formulation may be determined empirically and/or experimentally using standard practices. The pharmaceutical compositions are generally formulated as sterile, substantially isotonic and in full compliance with all Good Manufacturing Practice (GMP) regulations of the U.S. Food and Drug Administration.

Pharmaceutical compositions including the tubular nanostructures or the composite tubular nanostructures described herein can be administered to an individual by any of a number of routes including, but not limited to, oral, nasal, pulmonary, rectal, transdermal, vaginal, or transmucosal routes as well as the parenteral routes. Suitable parenteral delivery routes for the pharmaceutical compositions include, but are not limited to, intramuscular, subcutaneous, intramedullary injections, as well as intrathecal, direct intraventricular, intravenous, intraperitoneal, intranasal, or intraocular injections. Examples of microbead and nanoparticle approaches and materials that would be appropriate for the delivery of pharmaceutical compositions including the tubular nanostructures or the composite tubular nanostructures are described in *Nanomaterials for Medical Diagnosis and Therapy*, 1st edition, edited by Challa Kumar (Nanotechnologies for the Life Sciences Vol. 10, 2007, WILEY-VCH Verlag GmbH & Co. KGaA, Wienham; *Nanomaterials for Cancer Therapy*, edited by Challa Kumar (Nanotechnologies for the Life Sciences, Vol. 6, 2006, WILEY-VCH Verlag GmbH & Co. KGaA, Wienham, which are incorporated herein by reference).

The methods and compositions are further described with reference to the following examples; however, it is to be understood that the methods and compositions are not limited to such examples.

EXEMPLARY ASPECTS

Example 1

Preparation of Tubular Nanostructures for Targeting Cancer Cells

One or more tubular nanostructures may be used to selectively target and kill tumor cells in a subject with cancer. The one or more tubular nanostructures may be selectively directed to the tumor cells through a ligand associated with the tubular nanostructures that recognizes a corresponding cognate on the membrane of the tumor cells. The one or more ligands may be at least a portion of an antibody, antibody-coated liposome, polynucleotide, polypeptide, receptor, viral plasmid, polymer, protein, carbohydrate, lipid, toxins, pore-forming toxins, or lectin. The one or more cognates on a membrane of a tumor cell may be a least one of a protein, a carbohydrate, a glycoprotein, a glycolipid, a sphingolipid, a glycerolipid, or a metabolite thereof. For example, one or more carbon nanotubes may be modified with a ligand that is an antibody or fragment thereof that specifically binds a cognate that is a cell surface receptor on a tumor cell. A tumor cell may be a breast cancer cell. An example of a cell surface receptor on a breast cancer cell may be the HER2/erb/neu receptor. An antibody to HER2 may be attached to tubular nanostructures and used to direct interaction of the carbon nanotube to the breast cancer cells. Once at the targeted tumor cell, the one or more tubular nanostructures may form pores in the plasma membrane through which intracellular and extracellular components may flow. Disruption of the highly controlled barrier function of the plasma membrane ultimately results in death of the targeted tumor cell.

One or more tubular nanostructures for selective targeting of tumor cells may be derived from one or more carbon nanotubes. Carbon nanotubes may be generated using one of several methods including, but not limited to, arc-discharge, laser ablation, chemical vapor deposition (CVD), or the gas-phase catalytic process (HiPCO). For example, carbon nanotubes may be generated using an appropriate carbon source as described herein in the presence of one or more Group VI and/or Group VIII transition metals, e.g., chromium, iron, cobalt, ruthenium, nickel and platinum using laser vaporization with dual pulsed lasers as described in U.S. Pat. No. 7,008,604, which is incorporated herein by reference. Alternatively, carbon nanotubes may be purchased from a commercial source (from, e.g., Unidym, Menlo Park, Calif.; Sigma-Aldrich, St. Louis, Mo.; Carbolex, Inc., Lexington, Ky.)

The carbon nanotubes may be used directly for functionalization. Alternatively, the carbon nanotubes may be cut to generate more uniform, open-ended nanotubes. Disrupting the closed ends of the carbon nanotube will also facilitate functionalization of the ends. Carbon nanotubes may be cut by any of a number of different methods as described herein. For example, carbon nanotubes may be cut using an ultra microtome (Wang et al., *Nanotechnology* 18: 055301, 2007, which is incorporated herein by reference). In this instance, a magnetic field may be used to align the nanotubes prior to cutting. Pristine nanotubes are dispersed in water, stabilized in surfactant and passed under pressure through a nylon filter in the bore of a resistive coil magnetic, e.g., with a magnet field of 17.3 T. The nanotubes aligned on the filter are dried under vacuum. The resulting film of aligned nanotubes is cut and the strips stacked to form a rigid block of nanotubes. The block of nanotubes may be cut with a cryo-diamond knife at a temperature of approximately −60° C. using an ultra microtome, e.g., the Leica EM UC6 or EM FC6 microtome (from, e.g., Leica Microsystems, Bannockburn, Ill.).

The carbon nanotubes may be further treated by oxidation to facilitate functionalization of the ends and side-walls of the carbon nanotubes. As such, carbon nanotubes may be oxidized in the presence of strong oxidizing agents, e.g., nitric acid, $KMnO_4/H_2SO_4$, $O_2$, $K_2Cr_2O_7/H_2SO_4$ or $OsO_4$, to clean the nanotubes, cut the nanotubes, and/or prepare the nanotubes for functionalization. Oxidation of carbon nanotubes in nitric acid at a temperature of 120° C., for example, may be used to further clean the nanotubes by eliminating amorphous carbon and other contaminants. Oxidation may be also be used to cut the carbon nanotubes into shorter lengths and to open up the ends of the nanotubes. In addition, oxidation creates defects in the carbon nanotube sidewall which may be used to add moieties to the otherwise inert sidewall. As such, oxidation may be used to prepare the carbon nanotubes for functionalization. Following oxidation, the carbon nanotubes may be treated with neutralizing agents and further purified by size using electrophoresis, filtration or chromatography.

The carbon nanotubes are inherently hydrophobic. To facilitate improved insertion of the tubular nanostructure into the plasma membrane of a tumor cell, the carbon nanotubes may be functionalized at either or both ends with hydrophilic moieties. Hydrophilic moieties might include one or more of amines, amides, charged or polar amino acids, alcohols, carboxylic groups, oxides, ester groups, ether groups, ester-ether groups, ketones, aldehydes, or derivatives thereof. For example, carboxylic groups may be added to a carbon nanotube by sonicating the carbon nanotubes in a 3:1 vol/vol solution of concentrated sulfuric acid (98%) and concentrated nitric acid (70%) for 24 hours at 35-40° C., and washed with water, leaving an open hole in the nanotube and functionalizing the open end with one or more carboxyl group (see, e.g., Li, et al., *Proc. Natl. Acad. Sci. USA* 103:19658-19663, 2006, which is incorporated herein by reference).

The carbon nanotube may be further modified with a ligand that is an antibody or fragment thereof that specifically binds a cognate that is a cell surface receptor on a breast cancer. For example, the carbon nanotube may be modified with an antibody that specifically binds to the HER2/neu receptor on certain breast cancer cells. An example of an antibody that binds HER2/neu receptors on breast cancer cells is trastuzumab (Genentech, South San Francisco, Calif.). An antibody such as trastuzumab may be added to functionalized carbon nanotubes using one or more of the methods described herein. Alternatively, any of a number of commercially available antibodies to the HER2/neu receptor may be used (from, e.g., Novus Biologicals, Littleton, Colo.; Affinity BioReagents, Inc., Golden Colo.; Genway Biotech, Inc., San Diego, Calif.). For example, a thiolated antibody may be conjugated to carbon nanotubes functionalized with primary amines or phospholipid (PL)-PEG-$NH_2$ (see, e.g., McDevitt, et al., *J. Nucl. Med.* 48:1180-1189, 2007; Welsher, et al., *Nano Lett.* 8:586-590, 2008, which are incorporated herein by reference). PL-PEG-$NH_2$ (from, e.g., Avanti Polar Lipids, Inc., Alabaster, Ala.) at a concentration of 100-200 μM is mixed with approximately 0.25 mg/ml carbon nanotubes previously functionalized with hydrophilic ends in water and sonicated for 1 hour. The suspension is centrifuged at 200,000×g for 1 hour and the resulting pellet discarded. Excess PL-PEG-NH$_2$ may be removed by filtration through a filter, e.g., a filter with a 100 kDa molecular weight cut off (from, e.g., Millipore, Billerica, Mass.). The PL-PEG-NH$_2$ modified carbon nanotubes may be conjugated to thiolated antibody through a sulfo-SMCC linker. Thiolation may be accomplished using 2-iminothiolane.HCl which reacts with primary amines on the antibody to introduce sulfhydryl groups. The antibody (10 mg/ml) is mixed with 10-fold molar excess of 2-iminothiolane.HCl (e.g., 46 μl of a 14 mM stock solution of 2-iminothiolane to each milliliter of antibody solution) in phosphate buffered saline in the presence of 20 mM EDTA for 2 hours. Unreacted 2-iminothiolane may be removed by filtration through a 100 kDa filter. To finish conjugation, the PL-PEG-NH$_2$ modified carbon nanotubes (400 nM) are treated with 2 mM sulfo-SMCC (Pierce-Thermo Scientific, Rockford, Ill.) for 2 hours in phosphate buffered saline at pH 7.4 and excess sulfo-SMCC removed by filtration as above. The sulfo-SMCC treated carbon nanotubes are mixed with the thiolated antibody at a 1:10 molar ratio and allowed to incubate overnight at 4° C. to generate the carbon nanotube-antibody conjugate.

The tubular nanostructure as described herein is further modified with a ligand that is an antibody or fragment thereof, e.g., trastuzumab antibody, that specifically binds a cognate that is a HER2/neu cell surface receptor on certain breast cancer cells. The tubular nanostructure is targeted to the breast cancer cells, wherein the tubular nanostructure has a hydrophobic surface region flanked by two hydrophilic surface regions and is configured to form a pore in a lipid bilayer membrane of the breast cancer cell, and thus causing cell death of the breast cancer cell.

Example 2

Tubular Nanostructure with Lectin

One or more tubular nanostructures modified with a lectin may be used to selectively target and kill tumor cells in a subject with cancer. The one or more tubular nanostructures may be selectively directed to the tumor cells through a ligand, e.g., a lectin, associated with the tubular nanostructures that recognizes a corresponding cognate on the membrane of the tumor cells. In some instances, the binding of the lectin to the cognate on the target tumor cell may contribute to disruption and death of the targeted cell. For example, the lectin may be one of several galactose-binding plant lectins, e.g., *Ricinus communis* agglutinin I (RCA$_I$) or *Bandeirae simplicifolia* lectin I, which may bind to abnormally high quantities of galactose moieties found on the plasma membranes of some tumor cells, such as bladder carcinoma cells, and thereby weakening the membrane of the tumor cells and contributing to cell death (see, e.g., U.S. Pat. No. 4,496,539, which is incorporated herein by reference).

Tubular nanostructures generated using the methods as described herein may be modified with a lectin. For example, RCA$_I$, which is a 120,000 molecular weight protein, may be purchased from commercial sources (e.g., from Sigma-Aldrich, St. Louis, Mo.) and used to functionalize tubular nanostructures. Alternatively, all or part of RCAI may be generated using standard recombinant molecular biology techniques and corresponding cDNA sequences reported in GenBank as part of the National Center for Biotechnology Information (NCBI) (see, e.g., Benson, et al., *Nucleic Acids Res.* 36:D25-D30, 2008, which is incorporated herein by reference). RCA, may be conjugated to primary amines associated with tubular nanostructures using the methods described herein.

The tubular nanostructures may be further modified with one or more ligand such as an antibody or an aptamer, for example, that directs the nanotubes to the target tissue and enhances target specificity. For example, one or more aptamers specific for one or more cognates on a tumor cell may be generated using SELEX. In general, a diverse library of random DNA oligonucleotide sequences (40 to 55 nucleotides in length) may be amplified using the polymerase chain reaction (PCR) in the presence of a 5' primer labeled with a fluorescent tag and a 3' primer labeled with biotin. After denaturing the DNA under alkaline conditions, the fluorescently labeled sense single strand DNA (ssDNA) can be separated from the biotinylated antisense ssDNA using streptavidin coated Sepharose beads. Aptamers to live cells, for example, may be isolated by incubating the fluorescently labeled ssDNA with live cells and monitoring ssDNA binding by flow cytometry. Those ssDNA sequences that bind to the cells may be subjected to another round of PCR in the presence of labeled primers as described above. This cycle may be repeated several times until aptamers of appropriate binding affinity and selectivity are selected. Once the specific aptamer sequence for a target has been identified, the oligonucleotide sequence may be generated using standard procedures.

Example 3

Tubular Nanostructure with Toxin

One or more tubular nanostructures modified with one or more toxins may be used to selectively disrupt and kill target cells. The one or more toxins may act as a ligand to direct specific interaction with a cognate on a target cell. Alternatively, the one or more tubular nanostructures may be further modified with a ligand that specifically binds to a cognate on a target cell and brings the associated one or more toxins into proximity with the target cell.

The tubular nanostructures may include one or more toxins that specifically target and kill bacteria. For example, the one or more toxins may be one or more antimicrobial peptides. Antimicrobial peptides represent an abundant and diverse group of molecules that are naturally produced by many tissues and cell types in a variety of invertebrate, plant and animal species. The amino acid composition, amphipathicity, cationic charge and size of antimicrobial peptides allow them to attach to and insert into microbial membrane bilayers to form pores leading to cellular disruption and death. Antimicrobial peptides are generated as part of the host innate immune system and as such are capable of selectively targeting bacterial cells. For example, magainin 2, an antimicrobial peptide originally isolated from *Xenopus laevis*, may first be attracted to the net negative charges on the surface of bacteria associated with anionic phospholipids and the phosphate groups of lipopolysaccharide (LPS) on Gram-negative bacteria and teichoic acids on Gram-positive cells. Passing through the outer portions of the bacteria, the magainin 2 reaches the cytoplasmic membrane where it oligomerizes with other magainin 2 subunits to form a toroidal pore resulting in the immediate loss of cytoplasmic potassium and cell death (see, e.g., Brogden *Nat. Rev.*

*Microbiol.* 3:238-250, 2005, which is incorporated herein by reference). As such, magainin 2, for example, may be used to target and contribute to the death of bacteria.

Antimicrobial peptides, e.g., magainin 2 may be added to a tubular nanostructure using the methods described herein. Like many antimicrobial peptides, magainin 2 is a relatively small peptide with only 23 amino acids and as such is amenable to direct chemical peptide synthesis using commercial custom peptide synthesis services (from, e.g., Invitrogen, Carlsbad, Calif.; Sigma-Genosys, The Woodlands, Tex.; Abgent, San Diego, Calif.). Alternatively, magainin 2 or other antimicrobial peptides may be generated using standard recombinant molecular biology techniques and DNA sequence information available in GenBank as part of the National Center for Biotechnology Information (NCBI) (Benson, et al., *Nucleic Acids Res.* 36:D25-D30, 2008, which is incorporated herein by reference). The peptide is preferably synthesized with an amino terminal cysteine residue that enables interaction with a reactive group associated with the tubular nanostructure such as a succinimidyl group, for example. Tubular nanostructures such as carbon nanotubes are synthesized as described herein. The nanotubes are further functionalized with a primary amine group followed by addition of N-succinimidyl-3-maleimidopropionate (from, e.g., Pierce-Thermo Scientific, Rockford, Ill.) in preparation for adding the peptide. For example, carbon nanotubes (5-10 mg) are suspended in 2 milliliters of dimethylformamide (DMF) and mixed with 2 milliliters of N-succinimidyl-3-maleimidopropionate in DMF. The reaction is stirred for 4-8 hours at room temperature and excess N-succinimidyl-3-maleimidopropionate removed by incubation with a resin containing a primary amine, e.g., PEGA-$NH_2$ resin (from, e.g., Sigma-Aldrich, St. Louis, Mo.). The resin is removed by filtration. The carbon nanotubes as prepared are added to approximately 4 mg of purified peptides in 1.5 milliliters of an aqueous solution, e.g., water. After 4-8 hours, PEGA-$NH_2$ resin derivatized with N-succinimidyl-3-maleimidopropionate may be used to eliminate excess peptide and is removed by filtration.

In some instances, the tubular nanostructures may specifically target tumor cells and include one or more toxins. The one or more toxins may be a pore-forming toxin, e.g., aerolysin. Aerolysin is a bacterial toxin derived from *Aeromonas* spp that binds to glycosylphosphatidylinositol-anchored proteins (GPI-AP) on mammalian cells and oligomerizes, inserting into the target membranes and forming channels that cause cell death. Aerolysin may be generated using standard recombinant molecular biology techniques and the known polynucleotide sequences of aerolysin (see, e.g., Howard, et al., *J. Bacteriol.* 169:2869-2871, 1987, which is incorporated herein by reference).

The one or more toxin associated with a tubular nanostructure may by itself lack sufficient cell type specificity to selectively target tumor cells, for example. As such, the tubular nanostructures may further include a ligand that specifically binds a cognate on tumor cells. For example, the tubular nanostructures may include the luteinizing hormone-releasing hormone (LHRH) peptide. LHRH binds to LHRH receptors that are overexpressed on ovarian tumor cells and to a lesser extent on breast and prostate tumor cells (see, e.g., Khandare, et al., *J. Pharmacol. Exp. Ther.* 317:929-937, 2006; Dharap, et al., *Proc. Natl. Acad. Sci. USA* 102:12962-12967, 2005, which are incorporated herein by reference). LHRH may be generated using standard recombinant molecular biology techniques and the known polynucleotide sequences of LHRH available in GenBank as part of the National Center for Biotechnology Information (NCBI) (see, e.g., Benson, et al., *Nucleic Acids Res.* 36:D25-D30, 2008, which is incorporated herein by reference). Alternatively, LHRH may be obtained from commercial sources (from, e.g., Sigma-Aldrich, St. Louis, Mo.). Alternatively, LHRH may be purified from a nature source. LHRH may be conjugated to tubular nanostructure through its primary amines using the methods described herein for peptide ligands.

Example 4

Tubular Nanostructure with Controlled Flow

One or more tubular nanostructures targeted to a tumor cell may be further modified to control flow of biomolecules through the pores formed by the nanotubes in the lipid bilayer. For example, the pore associated with the tubular nanostructure may be closed by physically blocking the pore. The pore may be blocked by administering an agent to the subject that specifically binds at or near the pore opening. The agent may be a nanoparticle such as, for example a bead. The bead may be modified with an antibody, for example, that recognizes and binds to a ligand associated with one or both ends of the tubular nanostructure. Alternatively, the bead may be modified with a ligand that binds to an antibody associated with one or both ends of the tubular nanostructure. Alternatively, the bead may be modified with either streptavidin or biotin and as such binds to biotin or streptavidin, respectively, attached to the tubular nanostructure. Other biomolecule binding interactions that might be used to bind a bead to a tubular nanostructure include but are not limited to protein-protein interactions, sense-antisense DNA or RNA interactions, aptamer-target interaction, peptide-nucleic acid (PNA)-DNA or RNA interactions. The beads may be administered to the subject at some point in time after administration of the tubular nanostructures to block further movement of biomolecules through the pore.

Beads may be modified with an antibody, for example, using a number of methods. For example, antibodies may be conjugated to beads using amine or carboxyl derivatized beads (from, e.g., Pierce, Rockford, Ill.) using the cross linking methods described herein. Alternatively, an antibody may be conjugated to beads using immunoglobulin binding proteins derived from bacteria such as, for example, Protein A or Protein G. Beads modified with Protein A or Protein G are available from commercial sources (e.g., µMACS Protein A or µMACS Protein G MicroBeads, from Miltenyi Biotec, Auburn, Calif.; Protein A or Protein G sepharose, from Invitrogen, Carlsbad, Calif.).

Alternatively beads may be labeled with either streptavidin or biotin. Beads labeled with streptavidin are available from commercial sources (from, e.g., Applied Biosystems, Foster City, Calif.; BD Biosciences, San Jose, Calif.; and Invitrogen, Carlsbad, Calif.). Beads labeled with biotin are also available from commercial sources (from, e.g., Polysciences, Inc., Warrington, Pa.). Biotin and or streptavidin, for example, may be added to a tubular nanostructure using the methods described herein.

In some instances, the interaction between the tubular nanostructure and the bead may be reversible. For example, the binding affinity of the bead to the tubular nanostructure may be such that over time the two entities dissociate and the pore is re-opened. Alternatively, the bead may be dissociated from the tubular nanostructure by competition with free ligand.

Example 5

Tubular Nanostructure with Controlled Release of an Agent

One or more tubular nanostructures targeted to a tumor cell may be further modified to allow delivery of an agent proximal to the pore through the lipid bilayer formed by the nanotube. The agent may be a therapeutic agent and or a toxin that contributes to the death of the tumor cell. The agent may be bound to an antibody or aptamer that is itself bound to the tubular nanostructure. Alternatively, the agent may be bound to an antibody or aptamer that is administered subsequent to administration of the tubular nanostructures and binds to the membrane associated nanotube. In either instance, the agent dissociates from the antibody or aptamer and due to its proximity to the nanotube pore, flows through the pore and through the associated lipid bilayer.

An antibody may be generated against a therapeutic agent using the methods described herein. For example, antibodies to taxols such as the chemotherapy agent paclitaxel, for example, may be generated by attaching the taxol to a carrier protein such as bovine thyroglobin (BTG), immunizing mice, and generating monoclonal antibodies using standard hybridoma techniques (see, e.g., U.S. Pat. No. 7,175,993, which is incorporated herein by reference). Optionally, additional screening may be done to access binding affinity for the therapeutic agent to identify antibodies that have sufficient affinity to bind the agent but are able to dissociate the agent over a given time frame. Antigen/antibody on-off rates may be assessed using a Biacore 3000, for example (from Biacore, Inc., Piscataway, N.J.). Alternatively an antibody to a therapeutic agent may be available from a commercial source. For example, antibodies to the chemotherapeutic agent doxorubicin are commercially available (from, e.g., United States Biological, Swampscott, Mass.).

An antibody that recognizes and binds a chemotherapy agent, for example, may be bound to a tubular nanostructure using a heterofunctional cross linker or using other methods described herein. The antibody attached to the tubular nanostructure may be loaded with the chemotherapy agent prior to administering the tubular nanostructure to a subject. Alternatively, the chemotherapy agent may be administered before or after administration of the tubular nanostructure. In this instance, binding of the chemotherapy to the antibody associated with the tubular nanostructure would occur in vivo.

Alternatively, an antibody that recognizes and binds a chemotherapy agent may be a bifunctional antibody. In addition to recognizing and binding a chemotherapy agent, the bifunctional antibody may also recognize and bind to a ligand on the surface of the tubular nanostructure. The antibodies within the bifunctional antibody may be two or more intact antibodies and/or two or more antibody fragments such as, for example, Fab, F(ab)$_2$ and/or F$_v$ that are linked in some way to one another. The two or more antibodies may be fused by chemical conjugation, cross-linking and/or linker moieties. For example, polypeptides may be covalently bonded to one another through functional groups associated with the polypeptides such as, for example, carboxylic acid or free amine groups.

Alternatively, one or more antibodies may be linked through disulfide bonds. For example, the antibody that binds the chemotherapy agent may be reacted with N-succinimidyl S-acetylthioacetate (SATA) and subsequently deprotected by treatment with hydroxylamine to generate an SH-antibody with free sulfhydryl groups (see, e.g., U.S. Pat. App. No. 2003/0215454 A1, which is incorporated herein by reference). The antibody the binds the tubular nanostructure may be reacted with sulfosuccinimidyl 4-(N-maleimidomethyl)cyclohexane-1-carboxylate (sSMCC). The two antibodies treated as such are purified by gel filtration and then reacted with one another to form a bifunctional antibody complex. Alternatively, the antibodies may be chemically cross-linked to form a heteropolymerized complex using, for example, SPDP [N-succinimidyl-3-(2-pyridyldithio) propionate] (see, e.g., Liu, et al. *PNAS* 82:8648-8652, 1985; U.S. Pat. No. 5,470,570, which are incorporated herein by reference).

Alternatively, the two antibody binding activities may be incorporated into a single fusion protein using recombinant DNA approaches (see, e.g., U.S. Pat. No. 6,132,992, which is incorporated herein by reference). For example, cDNA encoding the variable regions ($V_L$ and $V_H$) of two antibodies directed against separate and distinct antigens, for example, may be combined into a linear expression construct from which a bispecific single-chain antibody may be produced (see, e.g., Haisma, et al. *Cancer Gene Ther.* 7:901-904, 2000, which is incorporated herein by reference). As such, cDNA encoding the variable regions ($V_L$, and $V_H$) of the antibody that binds the chemotherapy agent and the antibody that binds the tubular nanostructure, for example, may be manipulated to form a bispecific single-chain antibody.

The bifunctional antibody recognizing a chemotherapeutic agent and a tubular nanostructure may be combined with the tubular nanostructure prior to administering the nanotubes to a subject. Alternatively, the bifunctional antibody may be administered before or after administering the tubular nanostructures. As such, binding of the bifunctional antibody to the tubular nanostructures would occur in vivo. The chemotherapy agent may be bound to the bifunctional antibody when the latter is administered. Alternatively, the chemotherapy agent may be administered separately.

Example 6

Tubular Nanostructure with Marker

One or more tubular nanostructures modified with one or more marker may be used to selectively mark a target cell, e.g., a tumor cell. One or more tubular nanostructures may include one or more marker that is a fluorescent marker, a radioactive marker, a quantum dot, and/or magnetic resonance imaging marker. The one or more tubular nanostructures modified with one or more marker may be selectively directed to tumor cells or other target cells through a ligand associated with the tubular nanostructures that recognizes a corresponding cognate on the target cells. Imaging of the one or more marker may be used to monitor association of the tubular nanostructures with the targeted cells.

Tubular nanostructures generated using the methods described herein may be further modified with one or more markers. For example, a tubular nanostructure that includes an antibody to the HER-2 receptor as described herein may be further modified with one or more fluorescent markers, for example, to enable imaging of breast cancer cells. The one or more fluorescent markers may be any of a number of fluorescent dyes some of which are described herein. For example, fluorescein isothiocyanate (FITC) may be added to a tubular nanostructure using FITC modified phospholipid-PEG-NH$_2$ (see, e.g., Kam et al., *Proc. Natl. Acad. Sci. USA* 102:11600-11605, 2005, which is incorporated herein by reference). PL-PEG-NH$_2$ may be purchased from Avanti Polar Lipids (Alabaster, Ala.) and dissolved in 0.1 M carbonate buffer solution (pH 8.0) to which is added FITC (from, e.g., Sigma-Aldrich, St. Louis, Mo.). The mixture may be incubated overnight at room temperature with protection from light. The PL-PEG-FITC may be isolated from the reaction mix by gel chromatography on a Sephadex G-25 column, for example. The PL-PEG-FITC is mixed with carbon nanotubes and sonicated for 45 minutes to 1 hour and centrifuged at 22,000×g for 4-8 hours.

Alternatively, the one or more markers are indirectly linked to the carbon nanotube, for example, through a fluorescently labeled protein, antibody, oligonucleotide, aptamer or combinations thereof. For example, carbon nanotubes may be modified with a commercially available antibody to the HER-2 receptor that is itself labeled with a fluorescent marker (from, e.g, BioLegend, San Diego Calif.; R&D Systems, Inc., Minneapolis, Minn.).

In some instances, it may be beneficial to modify the tubular nanostructures with a fluorescent marker that emits at far red and/or near infrared wavelengths to minimize interference associated with endogenous cell and tissue autofluorescence. Examples of near infrared fluorescent markers include, but are not limited to, IRDye 800CW, IRDye 800RS, and IRDye 700DX (maximum emission wavelengths equal 794 nm, 786 nm, and 687 nm, respectively; from LI-COR, Lincoln, Nebr.); Cy5, Cy5.5, and Cy7 (maximum emission wavelengths equal 670 nm, 694 nm, and 760 nm, respectively; from Amersham Biosciences, Piscataway, N.J.); VivoTag 680 (VT680; VisEn Medical, Woburn, Mass.) and/or a variety of Alexa Fluor dyes including Alexa Fluor 633, Alexa Fluor 647, Alexa Fluor 660, Alexa Fluor 680, Alexa Fluor 700, and Alexa Fluor 750 (maximum emission wavelengths equal 647 nm, 668 nm, 690 nm, 702 nm, 723 nm, and 775 nm, respectively; from Molecular Probes-Invitrogen, Carlsbad, Calif., USA; see, e.g., U.S. Pat. App. No. 2005/0171434 A1). For example, IRDye 800CW may be added to functionalized tubular nanostructures using the methods described herein. IRDye 800CW with a reactive N-hydroxysuccinimide (NHS) group may be purchased from LI-COR, Lincoln, Nebr. The tubular nanostructures are appropriately prepared to include free amines such as with PL-PEG-NH$_2$ as described above which may react with IRDye 800CW-NHS to conjugate the IRDye to the nanotube.

In vivo, non-invasive monitoring of near infrared (NIR) fluorescence, for example, may be performed using fluorescence mediated molecular tomography as described, for example, in U.S. Pat. No. 6,615,063, which is incorporated herein by reference. Additional information regarding NIR imaging in human subjects, for example, is described in Frangioni *Curr. Op. Chem. Biol.* 7:626-634, 2003, which is incorporated herein by reference. In some instances, a wireless system may be used in which light sources such as light emitting diodes (LEDs) of appropriate wavelength as well as detectors such as charge-coupled devices (CCDs) are housed along with a power supply and a wireless communication circuit to create a device that may be placed on the skin of a subject to monitor NIR signal as described by Muehlemann, et al., *Optics Express*, 16:10323, 2008, which is incorporated herein by reference.

Example 7

Tubular Nanostructure with Activatable Marker

One or more tubular nanostructures modified with one or more activatable marker may be used to selectively mark a target cell. One or more markers associated with the tubular nanostructure may be activated by a ligand reaction, anchoring in the membrane and interaction with a hydrophobic medium, and/or change in the cellular environment (e.g., changes in pH). The one or more tubular nanostructures modified with one or more marker may be selectively directed to tumor cells or other target cells through a ligand associated with the tubular nanostructures that recognizes a corresponding cognate on the target cells. Imaging of the one or more marker may be used to monitor association of the tubular nanostructures with the targeted cells.

In some instances, the marker associated with the tubular nanostructures may be activated by anchoring in the hydrophobic lipid membrane. For example, a tubular nanostructure may be labeled with one or more fluorescent markers that fluoresce in the presence of a lipid environment. Examples of lipid-sensitive fluorescent markers include, but are not limited to, nitrobenzoxadiazole (NBD), diphenylhexatriene propionic acid (DHP), pyrene-labeled sn-2 acyl chains, and various derivatives thereof. A tubular nanostructure may be modified with NBD, for example, using commercially available NBD derivatives ready for conjugation. For example, the NBD derivatives 4-fluoro-7-nitrobenz-2-oxa-1,3-diazole (NBD fluoride), succinimidyl 6-(N-(7-nitrobenz-2-oxa-1,3-diazol-4-yl)amino)hexanoate (NBD-X, SE), and 6-(N-(7-nitrobenz-2-oxa-1,3-diazol-4-yl)amino)hexanoic acid (from, e.g., Invitrogen, Carlsbad, Calif.) can be reacted with primary amines as well as thiols, cysteines and secondary amines on the tubular nanostructures to conjugate NBD to the surface. NBD-X, SE, for example, may be added to tubular nanostructures with primary amines by combining the components together in a slightly basic buffer lacking primary amines, e.g., 0.1-0.2 M sodium bicarbonate buffer at pH 8.3 and incubating for 1-2 hours, followed by size exclusion gel filtration to separate the labeled nanotubes from the free NBD.

Alternatively, the maker associated with the tubular nanostructures may be activated by binding to a specific ligand on the target cell. For example, the marker may be an aptamer based molecular beacon. In this instance, the fluorescence associated with the molecular beacon is quenched until the beacon interacts with its intended target. Tumor targeting aptamers, for example, may be generated against whole tumor cells and/or specific tumor targets using the SELEX method described here.

In some instances, an aptamer may have a fluorophore in a region of the molecule known to undergo conformational change upon binding of a target that leads to an increase in fluorescence intensity. An aptamer of this sort may be selected for using an in vitro selection process with fluorescently labeled aptamers (see, e.g., Jhaveri, et al. *Nat. Biotech.* 18:1293-1297, 2000, which is incorporated herein by reference). A pool of RNA molecules is generated in which the random sequence region (45-60 residues) is skewed such that one of the residues, uridine, for example, is disproportionately underrepresented. The three to four randomly placed uridine residues are substituted with fluorescein-12-UTP, Cascade Blue-7-UTP, Texas Red-5-UTP, and/or Rhodamine Green-5-UTP during in vitro transcription. The labeled pool of RNA molecules are screened against the target cells or a specific target associated with the cells. Those RNA molecules that bind with high affinity to the target cells or a specific target associated with the cells are further screened for their fluorescence signaling properties in response to binding the target cells or a specific target associated with the cells. For example, the baseline fluorescence intensity is measured for RNA aptamer molecules labeled with fluorescein-12-UTP (excitation maxima 494 nm, emission maxima 521 nm) or Rhodamine Green-5-UTP (excitation maxima 505 nm, emission maxima 533 nm), for example, then re-measured in response to increasing concentrations of target cells or a specific target associated with the cells. As such, fluorescent aptamers may be selected that exhibit a 100-200% increase in fluorescence intensity in response to target binding.

An aptamer may be labeled either by direct incorporation of nucleic acids modified with fluorescent dyes or quenchers or by conjugation of fluorescent dyes or quenchers to appropriately modified nucleic acids. For example, an aptamer may be labeled directly with Cy3. The fluorophores may be attached to various chemical moieties that allow for attachment at various sites within the aptamer. For example, 3'-DABCYL CPG may be used to place DABCYL at the 3 prime terminus of the aptamer whereas 5'-DABCYL phosphoramidite may be used to place DABSYL at the 5 prime terminus of the aptamer (see, e.g., product information at Glen Research; www.glenres.com/Catalog/ labelling.html. DABCYL dT may be used to place DABCYL within the sequence. Labeling aptamers with appropriate commercially available fluorophores may be achieved following instructions provided by the respective manufacturer. Alternatively, an aptamer-based molecular beacon may be special ordered from a commercial source (from, e.g., Biosearch Technologies, Inc., Novato, Calif., USA).

An aptamer may be attached to a carbon nanotube (So et al, JACS). Tween may be bound non-covalently to the carbon nanotube sidewalls through hydrophobic interactions while the carboiimidazole may be covalently attached to the 3'-amine group of an RNA or DNA based aptamer.

In some instance, the tubular nanostructures may be modified with a marker that is an antibody that emits a signal a shift in emission wavelength, for example, in response to interacting with a ligand on the target cell or organelle (see, e.g., Brennan (1999) J. Fluor. 9:295-312). An antibody that exhibits a shift in fluorescent signal in response to binding of an antigen may be generated by labeling the antibody with a solvent-sensitive fluorophore such as dansyl chloride (5-dimethylaminonaphthalene-1-sulfonyl chloride), for example (see, e.g., Brennan (1999) J. Fluor. 9:295-312). The antibody is labeled such that binding of the antigen to the antibody shields the solvent sensitive fluorescent label near the active binding site from the solvent water, resulting in a 3-5 fold increase in fluorescence intensity (see, e.g., Bright, et al. (1990) Anal. Chem. 62:1065-1069). As such, an antibody directed against a specific illicit drug and/or drug of abuse, e.g., methamphetamine is incubated with methamphetamine (0.10 mg/ml) to block or protect the antibody/antigen binding site. The antibody/antigen complex is non-selectively labeled with 0.1 uM dansyl chloride under basic conditions of pH 8.5. The methamphetamine is removed from the dansylated antibody. In this instance, for example, subsequent binding of methamphetamine will result in a measureable increase in the intensity of the dansyl fluorescence at an emission wavelength of 420 nm when excited with a wavelength of 325 nm.

The tubular nanostructures modified with one or more marker may be further modified with one or more ligand that binds to a specific cognate on tumor cells. A ligand may be an antibody. An antibody may be conjugated to tubular nanostructures such as carbon nanotubes using a sulfo-SMCC linkage as described in Example 1. Alternatively, an antibody as well as other ligands may be conjugated to tubular nanostructures via a biotin/avidin interaction. In this instance, the tubular nanostructures may be modified with a phospholipid PEG-biotin moiety and interacted with an avidin labeled antibody. Biotin may be added to carbon nanotubes by mixing the carbon nanotubes (0.1 to 1 mg) in 1 to 5 ml of 166 µM DSPE-PEG(2000)-biotin (from Avanti Polar Lipids, Inc., Alabaster, Ala.) with sonication for 10 minutes. The samples are washed twice with water by centrifugation at 90,000×g for 15 minutes at 4° C. The supernatant may be discarded and the pellet resuspended in water and further centrifuged for 10 min at 16,000×g at room temperature. The top 50% of the supernatant containing biotinylated carbon nanotubes is taken for further conjugation. To prepare the antibody other ligand for conjugation, the antibody is thiolated with 2-iminothiolane as described herein to add sulfhydryl groups to the protein. The avidin protein is activated with m-maleimidobenzoyl-N-hydroxysuccinimide ester (MBS) as described by the manufacturer (product # 22311, Pierce Biotechnology, Rockford, Ill.). The thiolated antibody and the activated avidin may be conjugated to one another by mixing the two components at a molar ratio of 1:2 for 2 hours at room temperature with gentle shaking. The resulting conjugate may be purified by gel filtration on a Sephacryl S-300 HR column using 0.1 M phosphate buffered saline, 0.05% Tween-20, at pH 7.4. Carbon nanotubes modified with antibody are generated by mixing the biotinylated carbon nanotubes with the avidin labeled antibody in a 1:2 (wt/wt) ratio and incubated for 35 minutes at room temperature with gentle rocking. The mixture is centrifuged for 5 minutes at 16,000×g at 4° C., the supernatant disgarded and the pellet used for treatment. Alternatively, the carbon nanotube may be functionalized with streptavidin by non-covalent interactions and a biotinylated antibody or other ligand attached to the carbon nanotube via the streptavidin-biotin interaction (see, e.g., Lyonnais et al, *Small* 4:442-446, 2008, which is incorporated herein by reference).

Example 8

Composite Tubular Nanostructure

Two or more tubular nanostructures may be configured to form higher order assemblies or composite tubular nanostructures. A composite tubular nanostructure may comprise two or more tubular nanostructures each including a hydrophobic surface region, each hydrophobic region flanked by two hydrophilic surface regions configured to form a pore in a lipid bilayer membrane. Composite tubular nanostructures comprised of two or more tubular nanostructures may be used to create multiple pores at one or more sites in the targeted lipid bilayer. A composite tubular nanostructure may be generated by selective oxidation, sonication, and/or solubilization of carbon nanotube aggregates to generate smaller bundles of appropriate size and number. Alternatively, a composite tubular nanostructure may be generated from ordered assembly of single carbon nanotubes using biomolecule binding interactions, for example. Biomolecular binding interaction that might be used to bind a bead to a tubular nanostructure include but are not limited to streptavidin-biotin interactions, antigen-antibody interactions, protein-protein interactions, sense-antisense DNA or RNA interactions, aptamer-target interaction, peptide-nucleic acid (PNA)-DNA or RNA interactions.

Acid oxidation and sonication may be used to generate a stable aqueous suspension of purified single or small bundles of shortened nanotubes. Acid oxidation and sonication may also be used to introduce surface carboxylates on the nanotubes for chemical derivatization. As such, carbon nanotubes grown by laser ablation, for example, are refluxed for about 36 hours in 2.5 M HNO3, subjected to sonication for 30 minutes, and then refluxed again for another 36 hours. The mixture may be filtered through a polycarbonate filter with a defined pore size ranging from 10 nm to 100 nm (see, e.g., GE PCTE filters, GE Osmonics Labstore, Minnetonka, Minn.) to isolate a defined size range of nanotubes. Optionally, centrifugation at 7000 rpm for 5 min, for example, may be used to remove larger un-reacted impurities from the solution. Atomic force microscopy may be used to assess the size and dispersion of the tubular nanostructures following acid oxidation and Zeta potential measurements may be used to confirm the existence of negatively charged acidic groups on the nanotube sidewalls. (U.S. Patent Application 2006/0275371 A1, which is incorporated herein by reference). Alternatively, scanning and/or transmission electron microscopy and/or Raman spectroscopy may be used to monitor disaggregation of carbon nanotubes.

In some instances, the composite tubular nanostructure may be built by combining individual nanotubes that have been asymmetrically functionalized with compatable binding biomolecules such as, for example, biotin and streptavidin. For example, a polymer masking technique may be used to asymmetrically modify the nanotube sidewall as described by Qu & Dai Chem. Commun. 3859-3861, 2007, which is incorporated herein by reference. In this instance, one surface of the carbon nanotubes is embedded in a polystyrene film. The exposed surface is subsequently modified. For example, carbon nanotubes previously treated with acid and sonication and containing carboxylate groups as judged by Zeta potential measurements may be embedded in polystyrene. Carbodiimide and derivatives thereof may be used to convert the carboxylate groups to primary amines. These reactive amines are subsequently available for addition of other biomolecules. Additional modifications may be made while the nanotubes are embedded. Alternatively, the masking agent may be removed from the nanotubes prior to addition of other biomolecules. A masking agent such as polystyrene, for example, may be removed by treating the nanotubes with an treated with an organic solvent such as, for example, toluene.

The tubular nanotubes which have been asymmetrically functionalized with primary amine groups may be further modified with biotin using N-hydroxysuccinimide ester (NHS). Various NHS-biotin conjugates may be used for this purpose. For example, NHS-PEG4-Biotin and NHS-PEG12-Biotin (from Pierce-Thermo Scientific, Rockford, Ill.) may be used for simple and efficient biotin labeling of primary amine groups associated with, for example, carbon nanotubes. The associated polyethylene glycol (PEG) spacer associated with these NHS derivatives may also increase the solubility of the nanotubes. In some instances, it may be beneficial to use a biotin linker group with a cleavable disulfide bound (e.g., EZ Link NHS-SS-Biotin; from Pierce-Thermo Scientific, Rockford, Ill.), allowing for the disruption of the nanotube bundle in, for example, the interior of the cell.

To modify primary amines with NHS-PEG12-Biotin, for example, 1-10 mg of primary amine containing nanotubes are solubilized at a concentration of 2-10 mg/ml in an aqueous buffer at pH 7.2-8.0. In this instance, the carbon nanotubes, for example, may be concentrated in a small volume of dimethylformamide (DMF) or dimethyl sulfoxide (DMSO) or other water miscible solvent and added with gentle vortexing to the aqueous buffer. The NHS-PEG12-Biotin is similarly dissolved in DMF or DMSO other water miscible solvent and added at 10-20 fold molar excess relative to the carbon nanotubes. The NHS-PEG12-Biotin is allowed to incubate with the carbon nanotubes for 2-3 hours on ice or for 30-45 minutes at room temperature. The unbound NHS-PEG12-Biotin may be removed by dialysis.

A second set of tubular nanostructures may be modified with avidin or streptavidin and used with the biotin modified tubular nanostructures to form higher order bundles. Avidin or streptavidin may be non-specifically and non-covalently bound to the tubular nanostructures as described above. Alternatively, avidin or streptavidin may be added to tubular nanostructures using one or more of the various cross-linking agents described herein. For example, SMCC (succinimidyl 4-(N-maleimidomethyl)cyclohexane-1-carboxylate) may be used to crosslink the primary amines associated with functionalized carbon nanotubes with sulfhydryl groups associated with cysteine residues in avidin or streptavidin.

The tubular nanostructures modified with streptavidin and biotin, for example, may be combined to form composite tubular nanostructures. In some instances, the ratio of asymmetric labeled nanotubes to symmetric labeled nanotubes may be controlled. For example, to form a heptamer composite tubular nanostructure containing seven nanotubes, the ratio of asymmetric to symmetric nanotubes may be 6:1, for example.

Example 9

Composite Tubular Nanostructure with Ligand

One or more composite tubular nanostructures may be used to selectively target and kill tumor cells in a subject with cancer. One or more composite tubular nanostructure may be generated using the methods described. The one or more composite tubular nanostructures may be selectively directed to the tumor cells through a ligand associated with the composite tubular nanostructures that recognizes a corresponding cognate on the membrane of the tumor cells. The one or more ligands may be at least a portion of an antibody, antibody-coated liposome, polynucleotide, polypeptide, receptor, viral plasmid, polymer, protein, carbohydrate, lipid, toxins, pore-forming toxins, or lectin. Methods for modifying tubular nanostructures with ligands have been described herein. The one or more cognates on a membrane of a tumor cell may be a least one of a protein, a carbohydrate, a glycoprotein, a glycolipid, a sphingolipid, a glycerolipid, or a metabolite thereof. Once at the targeted tumor cell, the one or more composite tubular nanostructures may form pores in the plasma membrane through which intracellular and extracellular components may flow. Disruption of the highly controlled barrier function of the plasma membrane ultimately results in death of the targeted tumor cell.

Example 10

Tubular Nanostructures Targeted to Bacteria

One or more tubular nanostructures may be used to selectively target and damage bacterial cells in a subject with a bacterial infection. The one or more tubular nanostructures may be selectively directed to bacteria through a ligand associated with the tubular nanostructures that recognizes a corresponding cognate on the bacteria.

An antibody may be added to a tubular nanostructure to enable targeting of the nanotube to bacteria as described, for example, by Elkin et al (ChemBioChem 6:640-643, 2005, which is incorporated herein by reference). Tubular nanostructures, e.g., carbon nanotubes are functionalized with bovine serum albumin (BSA) using a carbodiimide-activated amidation reaction. Functionalization of the nanotubes with BSA renders the nanotubes more soluble in physiological buffers. An antibody directed against one or more bacteria can be non-covalently absorbed by the nanotube-BSA conjugate. In a typical procedure, a solution of antibody (10 ug/ml) in phosphate-buffered saline (PBS) or other physiologically relevant buffer is added to the nanotube-BSA solution (20 mg/ml). The suspension is mixed by slow rotation at 40 rpm for 20-24 hours at room temperature, for example, and then subjected to centrifugation at 14000×g to remove unbound antibody. The supernatant is discarded and the pelleted nanotube-BSA-antibody conjugate is washed repeatedly with additional PBS and centrifugation. The resulting nanotube-BSA-antibody conjugate may be passed through a membrane filter (e.g., 0.2 μm) to eliminate clumped nanotubes. Other methods for adding an antibody to tubular nanostructure may be contemplated, some methods of which are described herein.

Example 11

Tubular Nanostructure Targeted to Intracellular Organelle

One or more tubular nanostructure may be modified to allow transit of the nanotubes through the plasma membrane of a cell and subsequent targeting and insertion of the nanotubes into the lipid bilayer of an internal organelle such as, for example, mitochondria. In general, mitochondrial outer membrane permeabilization is considered the "point of no return" during apoptosis of cells as it results in diffusion to the cytosol of numerous proteins that normally reside in the space between the outer and inner mitochondrial membranes and initiates a cascade of events leading to cell death (see, e.g., Chipuk, et al., *Cell Death Differ.* 13:1396-1402, 2006, which is incorporated herein by reference). As such, one or more tubular nanostructures may be targeted to the outer membrane of mitochondria for insertion into and disruption of the outer mitochondrial membrane, leading to cell death. In some instances, the one or more tubular nanostructures may be further modified to target only mitochondria in cells of interest such as, for example, tumor cells. As such, tubular nanostructures may be first targeted to tumor cells with in a subject, pass through the tumor cell membrane, and target and disrupt the tumor cell mitochondria, leading to tumor cell death.

The tubular nanostructures as described herein have a hydrophobic surface region flanked by two hydrophilic surface regions for insertion and retention in a lipid bilayer. As such, tubular nanostructures generated as described herein may be modified in such a manner as to mask the hydrophilic ends and allow transit through the plasma membrane of a target cell. In one embodiment, the hydrophilic ends of the tubular nanostructure are modified with a hydrophobic moiety using a chemical bond that may be cleaved once the nanotube has passed into the cell. Examples of biologically cleavable bonds include, but are not limited to, disulfide bonds, diols, diazo bonds, ester bonds, sulfone bonds, acetals, ketals, enol ethers, enol esters, enamines and imines (see, e.g., U.S. Pat. Nos. 7,087,770, 7,098,030 and 7,348,453, which are incorporated herein by reference). Alternatively, the cleavable bond may be a photolabile bond. Examples of hydrophobic moieties that might be added to the ends of the tubular nanostructure include, but are not limited to, non-polar hydrocarbon chains of various lengths.

In one aspect, the hydrophobic moiety is an ester that can be cleaved by an intracellular esterase to form a hydrophilic acid moiety and alcohol moiety. For example, ceramides, which are long chain sphingoid bases linked to fatty acids, may be conjugated to other compounds through an ester linkage and used to transport compounds through the lipid bilayer and to release compounds inside the cell (see, e.g., Yatvin, et al., *Cell. Mol. Biol. Lett.* 5:119-132, 2000, which is incorporated herein by reference). As such, tubular nanostructures may be modified with ceramide or another long-chain nonpolar compound through an ester linkage at one or both ends of the nanotube.

Alternatively, the masked tubular nanostructures may enter the cell by passing directly through the cell membrane and into the cytoplasm. In this instance, the tubular nanostructure may include moieties on the surface of the nanotubes that confers direct passage through the lipid bilayer, e.g., an amphiphilic striated surface on the nanotube. The deposition of a hydrophilic-hydrophobic striated pattern of molecules, e.g., the anionic ligand 11-mercapto-1-undecane-sulphonate (MUS) and the hydrophobic ligand 1-octanethiol (OT) on the surface of nanotubes may facilitate direct passage of the tubular nanostructures into the cytoplasm (see, e.g., Verma, et al., *Nature Materials* 7: 588-95, 2008, which is incorporated herein by reference). For example, the hydrophilic ends of the tubular nanostructure may be modified with an amphipathic or hydrophobic moiety using a chemical bond that may be cleaved once the nanotube has passed into the cell. Examples of biologically cleavable bonds are discussed above. Once the masked tubular nanostructures has entered the cytoplasm, it can be modified to reveal tubular nanostructures with hydrophobic surface region flanked by two hydrophilic surface regions and at least one ligand bound to the nanostructure and configured to bind one or more cognates on an organellar membrane, e.g., a mitochondrial membrane.

In one aspect, hydrophilic moieties may be masked by acetoxymethyl esters of phosphates, sulfates, or other compounds having alcohol moieties or acid moieties, which will enhance permeability of the tubular nanostructure across the lipid bilayer membrane. Because acetoxymethyl esters are rapidly cleaved intracellularly, they facilitate the delivery of tubular nanostructures into the cytoplasm of the cell without puncturing or disruption of the cell plasma membrane (see, e.g., Schultz et al., *J. Biol. Chem.* 268: 6316-6322, 1993, which are incorporated herein by reference). Once within the cytoplasm, the tubular nanostructures having a hydrophobic surface region flanked by two hydrophilic surface regions is configured to form a pore in the lipid bilayer membrane of the cellular organelle. The cellular organelle may be mitochondria. Disruption of the outer membrane of the mitrochondria by the tubular nanostructures will cause cell death.

Under certain conditions, the masked tubular nanostructures may be actively taken up by the cell through the process of endocytosis (see, e.g., Kam, et al., *Angew. Chem. Int. Ed.* 44:1-6, 2005, which is incorporated herein by reference). As such, the tubular nanostructure may be optionally modified with an element that facilitates release of the tubular nanostructure from the endosome. For example, the masked tubular nanostructures may be modified with all or part of the influenza virus hemagglutinin-2 subunit (HA-2). HA-2 is a pH-dependent fusogenic peptide that induces lysis of membranes at low pH and may be used to induce efficient release of encapsulated material from cellular endosomes (see, e.g., Yoshikawa, et al., *J. Mol. Biol.* 380:777-782, 2008, which is incorporated herein by reference). All or part of HA-2 may be generated using standard recombinant molecular biology techniques and attached to the tubular nanostructures using methods described herein.

The tubular nanostructures are further modified with one or more ligands that binds to one or more cognates on mitochondria. The one or more ligands may be an antibody, antibody-coated liposome, polynucleotide, polypeptide, receptor, viral plasmid, polymer, protein, toxin, lectin, or any combination thereof as described herein. Cognates associated with a mitochondrial membrane may include at least one of a protein, a carbohydrate, a glycoprotein, a glycolipid, a sphingolipid, a glycerolipid, or metabolites thereof. Examples of cognates associated with the mitochondrial outer membrane, for example, include, but are not limited to, carnitine palmitoyl transferase 2, translocase of outer membrane (TOM70), sorting/assembly machinery, ANT, voltage dependent anion channel (VDAC/Porin), and monoamine oxidase.

The tubular nanostructures may be modified with one or more ligands that recognize VDAC/Porin, for example, a common protein expressed on the surface of the mitochondrial outer membrane. The ligand may be an antibody. Antibodies to VDAC/Porin, for example, may be generated using standard methods. Alternatively, antibodies to VDAC/Porin may be available from one or more commercial sources (from, e.g., GeneTex, Inc., San Antonio, Tex.; Sigma Aldrich, Saint Louis, Mo.; Genway Biotech Inc., San Diego, Calif.). An antibody to an outer mitochondrial membrane cognate such as VDAC/Porin may be attached to a tubular nanostructure using methods described herein.

Alternatively, the ligand may be all or part of an endogenous protein that is binding partner of VDAC/Porin. Examples of proteins that interact with VDAC/Porin include but are not limited to hexokinse, glycerol kinase, and Bax (see, e.g., Vyssokikh & Brdiczka, *Acta Biochimica Polonica* 50:389-404, 2003, which is incorporated herein by reference). As such, all or part of hexokinase, for example, may be generated using standard recombinant molecular biology techniques and the known polynucleotide sequences of hexokinase available in GenBank as part of the National Center for Biotechnology Information (NCBI) (see, e.g., Benson, et al., *Nucleic Acids Res.* 36:D25-D30, 2008, which is incorporated herein by reference). A protein or binding partner that interacts with one or more outer membrane proteins may be attached to a tubular nanostructure through amine groups associated with the protein, for example, using the methods described herein.

The tubular nanostructures may be further modified with one or more ligands that targets the tubular nanostructures specifically to tumor cells. The one or more ligand may be an antibody, an aptamer and or a peptide, for example, and attached to the tubular nanostructures as described here in.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

Those having ordinary skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having ordinary skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having ordinary skill in the art will recognize that the subject matter described herein may be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, as used herein, the specific exemplars set forth and the accompanying description are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The various aspects and embodiments disclosed herein are for purposes of illustration and are not intended to be limiting, with the true scope and spirit being indicated by the following claims.

What is claimed is:

1. A method for providing a stable pore in a lipid bilayer membrane comprising: positioning one or more elements at one or more of an intracellular end and an extracellular end of a tubular nanostructure, positioning the tubular nanostructure across a lipid bilayer membrane, wherein the tubular nanostructure includes a hydrophobic surface region flanked by two hydrophilic surface regions configured to form a pore in the lipid bilayer membrane and including at least one ligand configured to bind one or more cognates on the membrane, and reversibly blocking the pore with the one or more elements to control transport of molecules through the tubular nanostructure.

2. The method of claim 1, wherein one or more of the hydrophilic regions of the tubular nanostructure is located at an end of a tubular nanostructure.

3. The method of claim 1, wherein both hydrophilic regions are located at opposite ends of a tubular nanostructure.

4. The method of claim 1, wherein positioning the tubular nanostructure across the lipid bilayer membrane induces cell death.

5. The method of claim 1, wherein the lipid bilayer membrane is on a neoplastic cell, an infected cell, a bacterial cell, or a parasite cell.

6. A method for providing a stable pore in a lipid bilayer membrane comprising: positioning one or more elements at one or more of an intracellular end and an extracellular end of a composite tubular nanostructure, positioning the composite tubular nanostructure across a lipid bilayer membrane wherein the composite tubular nanostructure includes two or more nanotubes wherein at least one nanotube includes a hydrophobic surface region flanked by two hydrophilic surface regions configured to form a pore in a lipid bilayer membrane, and reversibly blocking the pore with the one or more elements to control transport of molecules through the tubular nanostructure.

7. The method of claim 6, wherein the hydrophilic regions are located at opposite ends of the at least one nanotubes.

8. The method of claim 6, wherein the tubular nanostructure positioned across the lipid bilayer membrane induces cell death.

9. The method of claim 6, wherein the lipid bilayer membrane is on a neoplastic cell, an infected cell, a bacterial cell, or a parasite cell.

10. The method of claim 6, wherein the tubular nanostructure is assisted in crossing the membrane core by lipid molecules from the membrane.

11. The method of claim 10, wherein the lipid molecules assisting the tubular nanostructure in crossing the membrane undergo lipid translocation across a bilayer leaflet.

12. A method for disrupting a lipid bilayer membrane of a cell comprising:
    positioning one or more elements at one or more of a cytoplasmic end and an extracellular end of at least one tubular nanostructure to control transport of molecules through the tubular nanostructure,
    contacting the cell with the at least one tubular nanostructure including a hydrophobic surface region flanked by two hydrophilic surface regions configured to form a pore in the lipid bilayer membrane and including at least one ligand configured to bind one or more cognates on the lipid bilayer membrane of the cell, and
    reversibly blocking the pore with one or more of the one or more elements to control transport of molecules through the tubular nanostructure.

13. The method of claim 12, wherein two or more ligands are configured to bind to the one or more cognates on the lipid bilayer membrane.

14. The method of claim 12, wherein the at least one tubular nanostructure positioned across the lipid bilayer membrane induces cell death.

15. The method of claim 1, wherein the hydrophobic surface region includes a single wall carbon nanotube surface region.

16. The method of claim 1, wherein the at least one ligand is a therapeutic compound configured to affect a cell or process or to treat at least one of a disease, condition, or symptom.

17. The method of claim 1, wherein the one or more elements are on the extracellular end of the nanostructure.

18. The method of claim 1, wherein the one or more elements are on the cytoplasmic end of the nanostructure.

19. The method of claim 1, wherein the one or more elements include a hydrophilic inner liner of the tubular nanostructure.

20. The method of claim 1, wherein the one or more elements include at least one second ligand configured to reversibly bind a cognate of interest, wherein the cognate of interest passes through the pore.

21. The method of claim 1, wherein the at least one ligand includes a monospecific antibody or a bispecific antibody.

22. The method of claim 12, wherein the one or more elements is a magnetic entity.

23. The method of claim 12, wherein the one or more elements include a molecular entity including one or more of at least a portion of a carbon nanostructure, polynucleotide, polypeptide, antibody, receptor, glycoprotein, lipid, polysaccharide, or polymer.

24. The method of claim 1, wherein the one or more elements include a charged group.

25. The method of claim 1, wherein the one or more elements are passive.

26. The method of claim 1, wherein the one or more elements are active.

27. The method of claim 25, wherein the pore permits transit or translocation of at least one compound across the membrane.

28. The method of claim 1, further comprising a marker attached to the nanostructure.

29. The method of claim 28, wherein the marker is activated by anchoring in the membrane.

30. The method of claim 29, wherein the marker is activated by a ligand reaction.

31. The method of claim 29, wherein the marker is activated by interaction with a hydrophobic medium.

32. The method of claim 1, wherein the hydrophobic surface region is extended in diameter.

33. The method of claim 32, wherein the hydrophobic surface region is extended in diameter by a disk, a stub, or a graphene sheet.

34. The method of claim 6, wherein the hydrophobic surface region includes a single wall carbon nanotube surface region.

35. The method of claim 6, wherein one or both of the hydrophilic surface regions are at the end of the nanostructure.

36. The method of claim 6, wherein the at least one ligand includes a therapeutic compound configured to affect a cell or process or to treat at least one of a disease, condition, or symptom.

37. The method of claim 6, wherein the one or more elements are on the extracellular end of the nanostructure.

38. The method of claim 6, wherein the one or more elements are on the cytoplasmic end of the nanostructure.

39. The method of claim 6, wherein the one or more elements include a hydrophilic inner liner of the tubular nanostructure.

40. The method of claim 6, wherein the one or more elements include at least one second ligand configured to reversibly bind a cognate of interest, wherein the cognate of interest passes through the pore.

41. The method of claim 6, wherein the at least one ligand includes a monospecific antibody or a bispecific antibody.

42. The method of claim 6, wherein the one or more elements is a magnetic entity.

43. The method of claim 6, wherein the one or more elements is a molecular entity including one or more of at least a portion of a carbon nanostructure, polynucleotide, polypeptide, antibody, receptor, glycoprotein, lipid, polysaccharide, or polymer.

44. The method of claim 6, wherein the one or more elements include a charged group.

45. The method of claim 6, wherein the one or more elements are passive.

46. The method of claim 6, wherein the one or more elements are active.

47. The method of claim 45, wherein the pore permits transit or translocation of at least one compound across the membrane.

48. The method of claim 6, further comprising a marker attached to the nanostructure.

49. The method of claim 48, wherein the marker is activated by anchoring in the membrane.

50. The method of claim 49, wherein the marker is activated by a ligand reaction.

51. The method of claim 49, wherein the marker is activated by interaction with a hydrophobic medium.

52. The method of claim 6, wherein the hydrophobic surface region is extended in diameter.

53. The method of claim 52, wherein the hydrophobic surface region is extended in diameter by a disk, a stub, or a graphene sheet.

54. The method of claim 1, wherein the one or more elements is a magnetic entity.

55. The method of claim 1, wherein the one or more elements include a molecular entity including one or more of at least a portion of a carbon nanostructure, polynucleotide, polypeptide, antibody, receptor, glycoprotein, lipid, polysaccharide, or polymer.

56. The method of claim 6, wherein the one or more elements is a magnetic entity.

57. The method of claim 6, wherein the one or more elements include a molecular entity including one or more of at least a portion of a carbon nanostructure, polynucleotide, polypeptide, antibody, receptor, glycoprotein, lipid, polysaccharide, or polymer.

\* \* \* \* \*

UNITED STATES PATENT AND TRADEMARK OFFICE
CERTIFICATE OF CORRECTION

PATENT NO.        : 9,617,157 B2                                      Page 1 of 1
APPLICATION NO.   : 12/322367
DATED             : April 11, 2017
INVENTOR(S)       : Bangera et al.

It is certified that error appears in the above-identified patent and that said Letters Patent is hereby corrected as shown below:

In the Claims

Column 62, Line 58, Claim 7: delete "at opposite ends of the at least one nanotubes." and insert --at opposite ends of the at least one nanotube.--

Signed and Sealed this
Thirtieth Day of May, 2017

Michelle K. Lee
*Director of the United States Patent and Trademark Office*